(12) United States Patent
Stone et al.

(10) Patent No.: US 6,210,949 B1
(45) Date of Patent: Apr. 3, 2001

(54) MOUSE MTS2 GENE

(75) Inventors: Steven Stone, Midvale; Ping Jiang; Alexander Kamb, both of Salt Lake City, all of UT (US)

(73) Assignee: Myriad Genetics, Inc., Salt Lake City, UT (US)

( * ) Notice: Subject to any disclaimer, the term of this patent is extended or adjusted under 35 U.S.C. 154(b) by 0 days.

(21) Appl. No.: 09/201,139

(22) Filed: Nov. 30, 1998

Related U.S. Application Data

(60) Division of application No. 08/508,735, filed on Jul. 28, 1995, now Pat. No. 5,843,756, which is a continuation-in-part of application No. 08/487,033, filed on Jun. 7, 1995, now Pat. No. 5,739,027, which is a continuation-in-part of application No. PCT/US95/03316, filed on Mar. 17, 1995.

(51) Int. Cl.$^7$ .............................. C07H 21/04; C12N 1/20; C12N 15/85; C12N 15/63
(52) U.S. Cl. .................. 435/252.3; 435/6; 435/320.1; 435/360; 435/325; 435/455; 435/471; 536/23.5; 536/24.31
(58) Field of Search ................ 435/6, 91.2, 320.1, 435/471, 455, 325, 252.3, 360; 536/23.5, 24.31, 24.33

(56) References Cited

FOREIGN PATENT DOCUMENTS

95/28483 * 10/1995 (WO) .

OTHER PUBLICATIONS

Kamb et al. Science. 264:436–440, Apr. 1994.*

Guan et al. Genes and Development. 8:2939–2952, 1994.*

Jen et al. Cancer Research. 54:6353–6358, Dec. 1994.*

* cited by examiner

*Primary Examiner*—Carla J. Myers
(74) *Attorney, Agent, or Firm*—Rothwell, Figg, Ernst & Kurz, p.c.

(57) ABSTRACT

The present invention relates to the Multiple Tumor Suppressor (MTS) genes in mice, their expression products, and their homology to the human MTS genes. The human MTS genes are involved in human cancers. The invention is further related to the use of the MTS genes in the therapy, diagnosis and prognosis of human cancer. The invention further relates to mutations in the MTS gene and their use in the diagnosis of predisposition to melanoma, leukemia, astrocytoma, glioblastoma, lymphoma, glioma, Hodgkin's lymphoma, CLL, and cancers of the pancreas, breast, thyroid, ovary, uterus, testis, kidney, stomach and rectum. The invention also relates to the therapy of human cancers which have a mutation in the MTS gene, including gene therapy, protein replacement therapy and protein mimetics. Finally, the invention relates to the screening of drugs for cancer therapy.

5 Claims, 28 Drawing Sheets

```
MTS1   0 TCCCCCGcCCGTwTTAAwTAAACCtCATCTTTCCAGAGTcTGTTTCTTATACCAGGAAATG
         |---------|---------|---------|---------|---------|---------
         1         11        21        31        41        51

MTS1  60 TaCACGTcTGAGAAACCCTTGCCCCAGACAGTCGTTTTACACGCAGGAGGGGAAGGGGAG
         |---------|---------|---------|---------|---------|---------
         61        71        81        91        101       111

MTS1 120 GGGAAGGAGAGAGCAGTCCTTTTcTCCAAAAGGAATCCTTnGAACTAGGGTTTCTGACTT
         |---------|---------|---------|---------|---------|---------
         121       131       141       151       161       171

MTS1 180 AGTGAACCCCGCGyTCCTGAAAATCAwGGGTTGAGGGGGTAGGGGGACACTTyCcTAGTC
         |---------|---------|---------|---------|---------|---------
         181       191       201       211       221       231

MTS1 240 GyACAGsTkATTTCGmTyCTCGGTGGGGCTCTCACAmCTAGGAAAGAATwGTTTTGCTTT
         |---------|---------|---------|---------|---------|---------
         241       251       261       271       281       291

MTS1 300 TTCTTATGATTAAAAGAAGAAGCCATACTTTtCCCTATGACACCAAACACCCCGATTCAA
         |---------|---------|---------|---------|---------|---------
         301       311       321       331       341       351

MTS1 360 TTTGGCAGTTAGGAAGGTTGTATCGCGGAGGAAGGAAACGGGGCGGGGGCGGATTTCTTT
         |---------|---------|---------|---------|---------|---------
         361       371       381       391       401       411

MTS1 420 TTtAACAGAGTGAACGCACTCAAACACGCCTTTGCTGGCAGGCGGGGGgAGCGCGGCTGG
         |---------|---------|---------|---------|---------|---------
         421       431       441       451       461       471

MTS1 480 GAGCAGGGGAGGCCGGAGGGCGGTGTGGGGGGCAGGTGGGGAGGAGCCCAGTCCTCCTTC
         |---------|---------|---------|---------|---------|---------
         481       491       501       511       521       531

MTS1 540 CTTGCCAACGCTGGCTCTGGCGAGGGCTGCTTyCGGCTGGTGCCCCCGGGGGAGACCCAA
         |---------|---------|---------|---------|---------|---------
         541       551       561       571       581       591

MTS1 600 CCTGGGGCGACTTCAGGGGTGCCACATTCGCTAAGTGCTCGGAGTTAATAGCACCTCCTC
         |---------|---------|---------|---------|---------|---------
         601       611       621       631       641       651

MTS1 660 CGAGCACTCGCTCACAGCGTCCCCTTGCCTGGAAAGATACCGCGGTCCCTCCAGAGGATT
         |---------|---------|---------|---------|---------|---------
         661       671       681       691       701       711
```

FIG. 5A

```
MTS1  720 TGAGGGACAGGGTCGGAGGGGGCTCTTCCGCCAGCACCGGAGGAAGAAAGAGGAGGGGCT
          |---------|---------|---------|---------|---------|---------
          721       731       741       751       761       771

MTS1  780 GGCTGGTCACCAGAGGGTGGGGCGGACCGCGTGCGCTCGGCGGCTGCGGAGAGGGGGAGA
          |---------|---------|---------|---------|---------|---------
          781       791       801       811       821       831

MTS1  840 GCAGGCAGCGGGCGGCGGGGAGCAGCATGGAGCCGGCGGCGGGGAGCAGCATGGAGCCTT
p16     0                                AATTCGGCACGAGGCAGCATGGAGCCTT
          |---------|---------|---------|---------|---------|---------
          841       851       861       871       881       891

MTS1  900 CGGCTGACTGGCTGGCCACGGCCGCGGCCCGGGGTCGGGTAGAGGAGGTGCGGGCGCTGC
p16    28 CGGCTGACTGGCTGGCCACGGCCGCGGCCCGGGGTCGGGTAGAGGAGGTGCGGGCGCTGC
          |---------|---------|---------|---------|---------|---------
          901       911       921       931       941       951
                                                                   ↓
MTS1  960 TGGAGGCGGGGGCGCTGCCCAACGCACCGAATAGTTACGGTCGGAGGCCGATCCAGGTGG
p16    88 TGGAGGCGGTGGCGCTGCCCAACGCACCGAATAGTTACGGTCGGAGGCCGATCCAG
          |---------|---------|---------|---------|---------|---------
          961       971       981       991       1001      1011

MTS1 1020 GTAGAGGGTCTGCAGCGGGAGCAGGGGATGGCGGGCGACTCTGGAGGACGAAGTTTGCAG
          |---------|---------|---------|---------|---------|---------
          1021      1031      1041      1051      1061      1071

MTS1 1080 GGGAATTGGAATCAGGTAGCGCTTCGATTCTCCGGAAAAAGGGGAGGCTTCCTGGGGAGT
          |---------|---------|---------|---------|---------|---------
          1081      1091      1101      1111      1121      1131

MTS1 1140 TTTCAGAAC
          |---------
          1141
```

FIG. 5B

```
MTS1    0 GAATTCATTGtGTACTGAAgAATGGaTAGAGAACTCAAGAAGGAAaTTGGaAACTGGAAG
          |---------|---------|---------|---------|---------|---------
          1         11        21        31        41        51

MTS1   60 CAAATGTAGGGGTAATTAGACACCTGGGGCTTGTGTGGGGGTCTGCTTGGCGGTGAGGGG
          |---------|---------|---------|---------|---------|---------
          61        71        81        91        101       111

MTS1  120 GcTCTACACAAGCTTCCTTTCCGTCATGCCGGCCCCCACCCTGGCTCTGACCATTCTGTT
          |---------|---------|---------|---------|---------|---------
          121       131       141       151       161       171
                     ↓
MTS1  180 CTCTCTGGCAGGTCATGATGATGGGCAGCGCCCGAGTGGCGGAGCTGCTGCTGCTCCACG
p16     0             GTCATGATGATGGGCAGCGCCCGAGTGGCGGAGCTGCTGCTGCTCCACG
          |---------|---------|---------|---------|---------|---------
          181       191       201       211       221       231

MTS1  240 GCGCGGAGCCCAACTGCGCCGACCCCGCCACTCTCACCCGACCCGTGCACGACGCTGCCC
p16    49 GCGCGGAGCCCAACTGCGCCGACCCCGCCACTCTCACCCGACCCGTGCACGACGCTGCCC
          |---------|---------|---------|---------|---------|---------
          241       251       261       271       281       291

MTS1  300 GGGAGGGcTTCCTGGACACGCTGGTGGTGcTGCACCGGGCCGGGGCGCGGCTGGACGTGC
p16   109 GGGAGGGCTTCCTGGACACGCTGGTGGTGCTGCACCGGGCCGGGGCGCGGCTGGACGTGC
          |---------|---------|---------|---------|---------|---------
          301       311       321       331       341       351

MTS1  360 GCGATGCCTGGGGCCGTCTGCCCGTGGACCTGGCTGAGGAGCTGGGCCATCGCGATGTCG
p16   169 GCGATGCCTGGGGCCGTCTGCCCGTGGACCTGGCTGAGGAGCTGGGCCATCGCGATGTCG
          |---------|---------|---------|---------|---------|---------
          361       371       381       391       401       411

MTS1  420 CACGGGTACCTGCGCGCGGCTGCGGGGGGCACCAGAGGCAGTAACCATGCCCGCATAGATG
p16   229 CACGGTACCTGCGCGCGGCTGCGGGGGGCACCAGAGGCAGTAACCATGCCCGCATAGATG
          |---------|---------|---------|---------|---------|---------
          421       431       441       451       461       471
                               ↓
MTS1  480 CCGCGGAAGGTCCCTCAGGTGAGGACTGATGATCTGAGAATTTGTACyCTGAGAGCTTCC
p16   289 CCGCGGAAGGTCCCTCAG
          |---------|---------|---------|---------|---------|---------
          481       491       501       511       521       531

MTS1  540 AAAGCTCAGAGCATTCATTTTCCAGCACAGAAAGTTCAGCCCGGGAGACCAGTCTCCGGT
          |---------|---------|---------|---------|---------|---------
          541       551       561       571       581       591
```

FIG. 6A

```
MTS1   600 CTTGCGCTCAGCTCACGCGCCAATGCGGTGGGACGGCCTGAGTCTCCCTATGCGCCCTGC
           |---------|---------|---------|---------|---------|---------
           601       611       621       631       641       651

MTS1   660 CsCGCACAGCGCGGCAAATGGGAAATAATCCCGAAATGGACTTGCGCACGTGAAAGCCCA
           |---------|---------|---------|---------|---------|---------
           661       671       681       691       701       711

MTS1   720 TTTTGTACGTTATACTTCCCAAAGCATACCACCACCCAAACACCTACCCTCTGCTAGTTC
           |---------|---------|---------|---------|---------|---------
           721       731       741       751       761       771

MTS1   780 AAGGCCTAGACTGCGGAGCAATGAAGACTCAAGAGGCTAGAGGTCTAGTGCCCCCTCTTC
           |---------|---------|---------|---------|---------|---------
           781       791       801       811       821       831

MTS1   840 CTCCAAACTAGGGCCAGTTGCATCsACTTACCAGGTCTGTTTCCTCATTTGCATACCAAG
           |---------|---------|---------|---------|---------|---------
           841       851       861       871       881       891

MTS1   900 CTGGCTGGACCAACCTCaGGATTTCCAAACCCAATTGTGCGTGGCATCATCTGGAGATCT
           |---------|---------|---------|---------|---------|---------
           901       911       921       931       941       951

MTS1   960 CTCGATCTCGGCTCTTCTGCACAACTCAACTAATCTGACCCTCCTCAgCTAATCTGACCC
           |---------|---------|---------|---------|---------|---------
           961       971       981       991       1001      1011

MTS1  1020 TCCGCTTTATGCGGTAGAGTTTTCCAGAgCTgCCCCAGGGGGTTCTGGGGACATCAGGAC
           |---------|---------|---------|---------|---------|---------
           1021      1031      1041      1051      1061      1071

MTS1  1080 CAAGACTTCGCTGACCCTGgCAGTCTGTGCACCGGAGttGGCTCCTTTCCCTCTTAAAcT
           |---------|---------|---------|---------|---------|---------
           1081      1091      1101      1111      1121      1131

MTS1  1140 TGTgCAAGAGATCCCTATAGTGAGTCGTATTATnCGGCCGCGAATTC
           |---------|---------|---------|---------|---------
           1141      1151      1161      1171      1181
```

FIG. 6B

```
MTS2    0 GATCATCACTTTACCATCAACTTTCTTGTCTCTGaACGTTTAGAGAATAAAATGGCATTT
          |---------|---------|---------|---------|---------|---------
          1         11        21        31        41        51

MTS2   60 AATtGGTvCTGAGTwTAACCTGAaGGTGGGGtGGGAAaGTGGwTTGCATCAGCAAdTGAA
          |---------|---------|---------|---------|---------|---------
          61        71        81        91        101       111

MTS2  120 GAAACACCAGAcATCAGAGACCTGAACACCTCtGCACTGGGTGAAAACTtgGCAATTAGG
          |---------|---------|---------|---------|---------|---------
          121       131       141       151       161       171

MTS2  180 TGTTTCTTTAAaTGGcTCCACCTGCCTtGCCCCGGCCGGcATCTcCcATACCTGCCCCCA
          |---------|---------|---------|---------|---------|---------
          181       191       201       211       221       231
                                                  ↓
MTS2  240 CCCTGGCTCTGACCACTCTGCTCTCTCTGGCAGGTCATGATGATGGGCAGCGCCCGCGTG
p16     0                               GTCATGATGATGGGCAGCGCCCGAGTG
          |---------|---------|---------|---------|---------|---------
          241       251       261       271       281       291

MTS2  300 GCGGAGCTGCTGCTGCTCcACGGCGCGGAGCCCAACTGCGCAGACCCTGCCACTCTCACC
p16    27 GCGGAGCTGCTGCTGCTCCACGGCGCGGAGCCCAACTGCGCCGACCCCGCCACTCTCACC
          |---------|---------|---------|---------|---------|---------
          301       311       321       331       341       351

MTS2  360 CGACCGGTGCATGATGCTGCCCGGGAGGGCTTCCTGGACACGCTGGTGGTGCTGCACCGG
p16    87 CGACCCGTGCACGACGCTGCCCGGGAGGGCTTCCTGGACACGCTGGTGGTGCTGCACCGG
          |---------|---------|---------|---------|---------|---------
          361       371       381       391       401       411

MTS2  420 GCCGGGGCGCGGCTGGACGTGCGCGATGCCTGGGGTCGTCTGCCCGTGGACTTGGCCGAG
p16   147 GCCGGGGCGCGGCTGGACGTGCGCGATGCCTGGGGCCGTCTGCCCGTGGACCTGGCTGAG
          |---------|---------|---------|---------|---------|---------
          421       431       441       451       461       471
                                                            o *
MTS2  480 GAGCGGGGCCACCGCGACGTTGCAGGGTACCTGCGCACAGCCACGGGGGACTGACGCCAG
p16   207 GAGCTGGGCCATCGCGATGTCGCACGGTACCTGCGCGCGGCTGCGGGGGGCACCAGAGGC
          |---------|---------|---------|---------|---------|---------
          481       491       501       511       521       531

MTS2  540 GTTCCCCAGCCGCCCACAACGACTTTATTTTCTTACCCAATTTCCCACCCCCACCCACCT
p16   267 AGTAACCATGCCCGCATAGATGCCGCGGAAGGTCCCTCAG
          |---------|---------|---------|---------|---------|---------
          541       551       561       571       581       591
```

FIG. 7A

```
MTS2  600  AATTCGATGAAGGCTGCCAACGGGGAGCGGCGGAAAGCCTGTAAGCCTGCAAGCCTGTCT
           |---------|---------|---------|---------|---------|---------
           601       611       621       631       641       651

MTS2  660  GAGACTCACAGGAAGGAGGAGCCGACCGGGAATAACCTTCCATACATTTTTTTCTTTGTC
           |---------|---------|---------|---------|---------|---------
           661       671       681       691       701       711

MTS2  720  TTATCTGGCCCTCGACACTCACCATGAAGCGAAACACAGAGAAGCGGATTTCCAGGGATA
           |---------|---------|---------|---------|---------|---------
           721       731       741       751       761       771

MTS2  780  TTTAGGAGTGTGTGACATTCCAGGGGTCGTTTGnTTTTCAGGGTTTTCTGAGGGAAAGTG
           |---------|---------|---------|---------|---------|---------
           781       791       801       811       821       831

MTS2  840  CATATGAAATCCTTGACTGGACCTGGTGGCTACGAATCTTCCCGATGGATGAATCTCCCA
           |---------|---------|---------|---------|---------|---------
           841       851       861       871       881       891

MTS2  900  CTCCAGCGCTGAGTGGGAGAAGGCAGTGATTAGCACTTGGGTGACGGCAGTCGATGCGTT
           |---------|---------|---------|---------|---------|---------
           901       911       921       931       941       951

MTS2  960  CACTCCAATGTCTGCTGAGGAGTTATGGTGAACCCACAACTTAGGCCCTAGCGGCAGAAA
           |---------|---------|---------|---------|---------|---------
           961       971       981       991       1001      1011

MTS2 1020  GGAAAACCTGAAGACTGAGGACAAAGTGGAGGAGGGCCGAGGTGGGCTTCAGTAtGTCCC
           |---------|---------|---------|---------|---------|---------
           1021      1031      1041      1051      1061      1071

MTS2 1080  CnnCGGCGCTTTAGTTTGAGCGCATGGCAAGTCACATGCGTAAACGACACTCTCTGGAAG
           |---------|---------|---------|---------|---------|---------
           1081      1091      1101      1111      1121      1131

MTS2 1140  CCCTGGAGACCCTCGCCCAACTCCACCAGATAGCAGAGGGGTAAGAGAGGATGTGCAAGC
           |---------|---------|---------|---------|---------|---------
           1141      1151      1161      1171      1181      1191

MTS2 1200  GACGACAGATGCTAAAATCCCTGGATCACGACGCTGCAGAGCAC
           |---------|---------|---------|---------|
           1201      1211      1221      1231      1241
```

FIG. 7B

```
MTS1   0 TGTGTGGGGGTCTGCTTGGCGGTGAGGGGGCTCTACACAAGCTTCCTTTCCGTCATGCCG
MTS2   0 AATTAGGTGTTTCTTTAAATGGCTCCACCTGCCTTGCCCCGGCCGGCATCTCCCATACCT
         |---------|---------|---------|---------|---------|---------
                                              ▽
MTS1  60 GCCCCCACCCTGGCTCTGACCATTCTGTTCTCTCTGGCAGGTCATGATGATGGGCAGCGC
MTS2  60 GCCCCCACCCTGGCTCTGACCACTCTGCTCTCTCTGGCAGGTCATGATGATGGGCAGCGC
         |---------|---------|---------|---------|---------|---------

MTS1 120 CCGAGTGGCGGAGCTGCTGCTGCTCCACGGCGCGGAGCCCAACTGCGCCGACCCCGCCAC
MTS2 120 CCGCGTGGCGGAGCTGCTGCTGCTCCACGGCGCGGAGCCCAACTGCGCAGACCCTGCCAC
         |---------|---------|---------|---------|---------|---------

MTS1 180 TCTCACCCGACCCGTGCACGACGCTGCCCGGGAGGGCTTCCTGGACACGCTGGTGGTGCT
MTS2 180 TCTCACCCGACCGGTGCATGATGCTGCCCGGGAGGGCTTCCTGGACACGCTGGTGGTGCT
         |---------|---------|---------|---------|---------|---------

MTS1 240 GCACCGGGCCGGGGCGCGGCTGGACGTGCGCGATGCCTGGGGCCGTCTGCCCGTGGACCT
MTS2 240 GCACCGGGCCGGGGCGCGGCTGGACGTGCGCGATGCCTGGGGTCGTCTGCCCGTGGACTT
         |---------|---------|---------|---------|---------|---------
                                                                 ↓
MTS1 300 GGCTGAGGAGCTGGGCCATCGCGATGTCGCACGGTACCTGCGCGCGGCTGCGGGGGGCAC
MTS2 300 GGCCGAGGAGCGGGGCCACCGCGACGTTGCAGGGTACCTGCGCACAGCCACGGGGGACTG
         |---------|---------|---------|---------|---------|---------
                                                      ▽
MTS1 360 CAGAGGCAGTAACCATGCCCGCATAGATGCCGCGGAAGGTCCCTCAGGTGAGGACTGATG
MTS2 360 ACGCCAGGTTCCCCAGCCGCCCACAACGACTTTATTTTCTTACCCAATTTCCCACCCCCA
         |---------|---------|---------|---------|---------|---------

MTS1 420 ATCTGAGAATTTGTACYCTGAGAGCTTCCAAAGCTCA
MTS2 420 CCCACCTAATTCGATGAAGGCTGCCAACGGGGAGCGG
         |---------|---------|---------|---------
```

| CLASS | # LINES | 1063.7 | c18.B | c5.1 | RN3.1 | c5.3 | R2.3 | R2.7 | RN1.1 | c1.B |
|---|---|---|---|---|---|---|---|---|---|---|
| 1 | 59 | − | − | − | − | − | − | − | − | − |
| 2 | 5 | + | − | − | − | − | − | − | − | − |
| 3 | 1 | + | + | − | − | − | − | − | − | − |
| 4 | 2 | + | + | + | − | − | − | − | − | − |
| 5 | 23 | − | − | − | − | − | − | − | − | + |
| 6 | 8 | + | + | − | + | − | − | − | − | + |
| 7 | 4 | + | + | + | + | − | − | − | − | + |
| 8 | 1 | + | − | − | − | − | − | − | − | + |
| 9 | 1 | + | + | + | − | − | − | − | − | + |
| 10 | 7 | + | + | − | + | − | − | − | + | + |
| 11 | 1 | − | − | + | − | − | − | − | + | + |
| 12 | 1 | + | − | − | − | − | − | − | + | + |
| 13 | 1 | + | + | + | + | − | − | − | + | + |
| 14 | 2 | − | − | − | − | − | − | + | + | + |
| 15 | 5 | + | + | − | − | + | + | + | + | + |
| 16 | 6 | + | − | − | + | + | + | + | + | + |
| 17 | 1 | − | + | − | − | + | + | + | + | + |
| 18 | 1 | + | + | + | + | + | + | + | + | + |
| 19 | 4 | + | − | − | − | + | + | + | + | + |
| 20 | 1 | + | + | + | + | + | + | + | + | + |
| 21 | 1 | + | + | − | − | + | + | + | + | + |
| 22 | 1 | + | + | + | + | + | + | + | + | + |
| TOTAL | 135 | | | | | | | | | |
| DELETIONS | 160 | 99 | 117 | 129 | 128 | 127 | 116 | 115 | 114 | 67 |

TIME →

```
CGGGCAGTGA GGACTCCGCG ACGCGTCCGC ACCCTGCGGC CAGAGCGGCT TTGAGCTCGG   60

CTGCGTCCGC GCTAGGCGCT TTTTCCCAGA AGCAATCCAG GCGCGCCCGC TGGTTCTTGA  120

GCGCCAGGAA AAGCCCGGAG CTAACGACCG GCCGCTCGGC CACTGCACGG GGCCCCAAGC  180

CGCAGAAGGA CGACGGGAGG GTAATGAAGC TGAGCCCAGG TCTCCTAGGA AGGAGAGAGT  240

GCGCCGGAGC AGCGTGGGAA AGAAGGGAAG AGTGTCGTTA AGTTTACGGC CAACGGTGGA  300

TTATCCGGGC CGCTGCGCGT CTGGGGGCTG CGGA ATG CGC GAG GAG AAC AAG      352
                                   Met Arg Glu Glu Asn Lys
                                    1                   5
```

```
GGC ATG CCC AGT GGG GGC GGC AGC GAT GAG GGT CTG GCC AGC GCC GCG   400
Gly Met Pro Ser Gly Gly Gly Ser Asp Glu Gly Leu Ala Ser Ala Ala
         10              15                  20

GCG CGG GGA CTA GTG GAG AAG GTG CGA CAG CTC CTG GAA GCC GGC GCG   448
Ala Arg Gly Leu Val Glu Lys Val Arg Gln Leu Leu Glu Ala Gly Ala
         25              30                  35           ↓

GAT CCC AAC GGA GTC AAC CGT TTC GGG AGG CGC GCG ATC CAG GTC ATG   496
Asp Pro Asn Gly Val Asn Arg Phe Gly Arg Arg Ala Ile Gln Val Met
         40              45                  50

ATG ATG GGC AGC GCC CGC GTG GCG GAG CTG CTG CTG CTC CAC GGC GCG   544
Met Met Gly Ser Ala Arg Val Ala Glu Leu Leu Leu Leu His Gly Ala
 55              60                  65                  70

GAG CCC AAC TGC GCA GAC CCT GCC ACT CTC ACC CGA CCG GTG CAT GAT   592
Glu Pro Asn Cys Ala Asp Pro Ala Thr Leu Thr Arg Pro Val His Asp
                 75                  80                  85

GCT GCC CGG GAG GGC TTC CTG GAC ACG CTG GTG GTG CGT CAC CGG GCC   640
Ala Ala Arg Glu Gly Phe Leu Asp Thr Leu Val Val Arg His Arg Ala
                 90                  95                 100

GGG GCG CGG CTG GAC GTG CGC GAT GCC TGG GGT CGT CTG CCC GTG GAC   688
Gly Ala Arg Leu Asp Val Arg Asp Ala Trp Gly Arg Leu Pro Val Asp
            105                 110                 115

TTG GCC GAG GAG CGG GGC CAC CGC GAC GTT GCA GGG TAC CTG CGC ACA   736
Leu Ala Glu Glu Arg Gly His Arg Asp Val Ala Gly Tyr Leu Arg Thr
120                 125                 130

GCC ACG GGG GAC TGA                                                751
Ala Thr Gly Asp
135
```

FIG. 11

CGCGCCTGCG GGGCGGAGAT GGGCAGGGGG CGGTGCGTGG GTCCCAGTCT GCAGTTAAGG 60

GGGCAGGAGT GGCGCTGCTC ACCTCTGGTG CCAAAGGGCG GCGCAGCGGC TGCCGAGCTC 120

GGCCCTGGAG GCGGCGAGAA CATGGTGCGC AGGTTCATGG TGACCCTCCG GATTCGGCGC 180

GCGTGCGGAG CGCCGCGAGT GAGGGTTTTC GTGGTTCACA TCCCGCGGCT CACGGGGGAG 240

TGGGCAGCGC CAGGGGCGCC CGCCGCTGTG GCCCTCGTGC TGATGCTACT GAGGAGCCAG 300

CGTCTAGGGC AGCAGCCGCT TCCTAGAAGA CCAGGTC ATG ATG ATG GGC AGC GCC 355
                                                            Met Met Met Gly Ser Ala
                                                             1            5

CGA GTG GCG GAG CTG CTG CTG CTC CAC GGC GCG GAG CCC AAC TGC GCC 403
Arg Val Ala Glu Leu Leu Leu Leu His Gly Ala Glu Pro Asn Cys Ala
          10                   15                  20

GAC CCC GCC ACT CTC ACC CGA CCC GTG CAC GAC GCT GCC CGG GAG GGC 451
Asp Pro Ala Thr Leu Thr Arg Pro Val His Asp Ala Ala Arg Glu Gly
        25                    30                  35

TTC CTG GAC ACG CTG GTG GTG CTG CAC CGG GCC GGG GCG CGG CTG GAC 499
Phe Leu Asp Thr Leu Val Val Leu His Arg Ala Gly Ala Arg Leu Asp
   40                    45                  50

GTG CGC GAT GCC TGG GGC CGT CTG CCC GTG GAC CTG GCT GAG GAG CTG 547
Val Arg Asp Ala Trp Gly Arg Leu Pro Val Asp Leu Ala Glu Glu Leu
55                60                  65                  70

FIG. 12A

```
GGC CAT CGC GAT GTC GCA CGG TAC CTG CGC GCG GCT GCG GGG GGC ACC    595
Gly His Arg Asp Val Ala Arg Tyr Leu Arg Ala Ala Ala Gly Gly Thr
                75                  80                  85
                                                          ↓
AGA GGC AGT AAC CAT GCC CGC ATA GAT GCC GCG GAA GGT CCC TCA GAC    643
Arg Gly Ser Asn His Ala Arg Ile Asp Ala Ala Glu Gly Pro Ser Asp
            90                  95                  100

ATC CCC GAT TGAAAGAACC AGAGAGGCTC TGAGAAACCT CGGGAAACTT            692
Ile Pro Asp
        105

AGATCATCAG TCACCGAAGG TCCTACAGGG CCACAACTGC CCCCGCCACA ACCCACCCCG  752

CTTTCGTAGT TTTCATTTAG AAAATAGAGC TTTTAAAAAT GTCCTGCCTT TTAACGTAGA  812

TATAAGCCTT CCCCCACTAC CGTAAATGTC CATTTATATC ATTTTTTATA TATTCTTATA  872

AAAATGTAAA AAAGAAAAAC ACCGCTTCTG CCTTTTCACT GTGTTGGAGT TTTCTGGAGT  932

GAGCACTCAC GCCCTAAGCG CACATTCATG TGGGCATTTC TTGCGAGCCT CGCAGCCTCC  992

GGAAGCTGTC GACTTCATGA CAAGCATTTT GTGAACTAGG GAAGCTCAGG GGGGTTACTG 1052

GCTTCTCTTG AGTCACACTG CTAGCAAATG GCAGAACCAA AGCTCAAATA AAAATAAAAT 1112

TATTTTCATT CATTCACTC                                              1131
```

FIG. 12B

```
MOUSEβ        aagaGAGGGTTTTCtTGGTaaAgtTCgtGCGatcCcgGaGacccaG
HUMANβ        ccgcgagtGAGGGTTTTCgTGGTtcAcaTCccGCGgctCacGgGggagtG
              |--------|---------|---------|---------|---------|
              1        10        20        30        40        50

MOUSEβ        GaCAGCGtagctGcgctCtGgCttTCGTGaaCaTgtTGttTGAgGCTAgaG
HUMANβ        GgCAGCGccaggGgcgcCcGcCgcT-GTGgcCcTcgTGcTGAtGCTActG
              |--------|---------|---------|---------|---------|
              51       60        70        80        90        100

V
MOUSEβ        AGGAtCttGaGaagAGGGCcGCAcCgGaaTCCTgGA---CCAGGTgATGA
HUMANβ        AGGAgCcaGcGtctAGGGCaGCAgCcGctTCCTaGAAGACCAGGTcATGA
              |--------|---------|---------|---------|----------|
              101      110       120       130       140       150

MOUSEβ        TGATGGGCAaCGttCacGTaGCaGctCTtCTGCTcaaCtACGGtGCaGAt
HUMANβ        TGATGGGCAgCGccCgaGTgGCgGagCTgCTGCTgctCcACGGcGCgGAg
              |--------|---------|---------|---------|---------|
              151      160       170       180       190       200

MOUSEβ        tCgAACTGCGagGACCCCaCtACctTCtCCCGcCCgGTGCACGACGCaGC
HUMANβ        cCcAACTGCGccGACCCCgCcACtcTCaCCCGaCCcGTGCACGACGCtGC
              |--------|---------|---------|---------|---------|
              201      210       220       230       240       250

MOUSEβ        gCGcGAaGGCTTCCTGGACACGCTGGTGGTGCTGCACgGGtCaGGGGCtC
HUMANβ        cCGgGAgGGCTTCCTGGACACGCTGGTGGTGCTGCACcGGGCcGGGGCgC
              |--------|---------|---------|---------|---------|
              251      260       270       280       290       300

MOUSEβ        GGCTGGAtGTcCGCGATGCCTGGGGtCGcCTcCCgcTcGACTTcGCccAa
HUMANβ        GGCTGGAcGTgCGCGATGCCTGGGGcCGtCTgCCcgTgGACCTgGCtgAg
              |--------|---------|----------|---------|--------|
              301      310       320        330       340      350

MOUSEβ        GAGCgGGGaCATCaaGAcaTCGtgCGaTAttTGCGttCcGCTGgGtGctc
HUMANβ        GAGCtGGGcCATCgcGAtgTCGcaCGgTAccTGCGcgCgGCTGcGgGggg
              |--------|---------|---------|---------|--------|
              351      360       370       380       390      400

MOUSEβ        TT
HUMANβ        CACCAGAGGCAGTAACCATGCCCGCATAGATGCCGCGGAAGGTCCCTCAG
              |---------|---------|---------|---------|--------|
              401       410       420       430       440      450
```

FIG. 14

```
  0 ATGGAGCCGGCGGCGGGGAGCAGCATGGAGCCTTCGGCTGACTGGCTGGCCACGGCCGCG
    |---------|---------|---------|---------|---------|---------|------
    6        16        26        36        46        56

60 GCCCGGGGTCGGGTAGAGGAGGTGCGGGCGCTGCTGGAGGCGGTGGCGCTGCCCAACGCA
    |---------|---------|---------|---------|---------|---------|------
    66       76        86        96       106       116

120 CCGAATAGTTACGGTCGGAGGCCGATCCAGGTCATGATGATGGGCAGCGCCCGAGTGGCG
    |---------|---------|---------|---------|---------|---------|------
    126      136       146       156       166       176

180 GAGCTGCTGCTGCTCCACGGCGCGGAGCCCAACTGCGCCGACCCCGCCACTCTCACCCGA
    |---------|---------|---------|---------|---------|---------|------
    186      196       206       216       226       236

240 CCCGTGCACGACGCTGCCCGGGAGGGCTTCCTGGACACGCTGGTGGTGCTGCACCGGGCC
    |---------|---------|---------|---------|---------|---------|------
    246      256       266       276       286       296

300 GGGGCGCGGCTGGACGTGCGCGATGCCTGGGGCCGTCTGCCCGTGGACCTGGCTGAGGAG
    |---------|---------|---------|---------|---------|---------|------
    306      316       326       336       346       356

360 CTGGGCCATCGCGATGTCGCACGGTACCTGCGCGCGGCTGCGGGGGGCACCAGAGGCAGT
    |---------|---------|---------|---------|---------|---------|------
    366      376       386       396       406       416

420 AACCATGCCCGCATAGATGCCGCGGAAGGTCCCTCAG--ACATCCCCGATTGAAAGAACC
    |---------|---------|---------|---------|---------|---------|------
    426      436       446       456       466       476

478 AGAGAGGCTCTGAGAAACCTCGGGAAACTTAGATCATCAGTCACCGAAGGTCCTACAGGG
    |---------|---------|---------|---------|---------|---------|------
    486      496       506       516       526       536

538 CCACAACTGCCCCCGCCACAACCCACCCCGCTTTCGTAGTTTTCATTTAGAAAATAGAGC
    |---------|---------|---------|---------|---------|---------|------
    546      556       566       576       586       596

598 TTTTAAAAATGTCCTGCCTTTTAACGTAGATATAAGCCTTCCCCCACTACCGTAAATGTC
    |---------|---------|---------|---------|---------|---------|------
    606      616       626       636       646       656

658 CATTTATATCATTTTTTATATATTCTTATAAAAATGTAAAAAAGAAAAACACCGCTTCTG
    |---------|---------|---------|---------|---------|---------|------
    666      676       686       696       706       716

718 CCTTTTCACTGTGTTGGAGTTTTCTGGAGTGAGCACTCACGCCCTAAGCGCACATTCATG
    |---------|---------|---------|---------|---------|---------|------
    726      736       746       756       766       776

778 TGGGCATTTCTTGCGAGCCTCGCAGCCTCCGGAAGCTGTCGACTTCATGACAAGCATTTT
    |---------|---------|---------|---------|---------|---------|------
    786      796       806       816       826       836

838 GTGAACTAGGGAAGCTCAGGGGGGTTACTGGCTTCTCTTGAGTCACACTGCTAGCAAATG
    |---------|---------|---------|---------|---------|---------|------
    846      856       866       876       886       896

898 GCAGAACCAAAGCTCAAATAAAAATAAAATTATTTTCATTCATTCACTC
    |---------|---------|---------|---------|---------
    906      916       926       936       946
```

```
mouse p16                              M E S A A D R L A R A A
human p16      M E P A A G S S M E P S A D W L A T A A
mouse p15                  M L G G S S D A G L A T A A
human p15  M R E E N K G M P S G G G S D E G L A S A A mouse p16  A Q G R V P D V R A L L E A G V S P N A P N
human p16  A R G R V E E V R A L L E A G A L P N A P N
mouse p15  A R G Q V E T V R Q L L E A G A D P N A L N
human p15  A R G L V E K V R Q L L E A G A D P N G V N mouse p16  S F G R T P I Q V M M M G N V H V A A L L L
human p16  S Y G R R P I Q V M M M G S A R V A E L L L
mouse p15  R F G R R P I Q V M M M G S A Q V A E L L L
human p15  R F G R R A I Q V M M M G S A R V A E L L L mouse p16  N Y G A D S N C E D P T T F S R P V H D A A
human p16  L H G A E P N C A D P A T L T R P V H D A A
mouse p15  L H G A E P N C A D P A T L T R P V H D A A
human p15  L H G A E P N C A D P A T L T R P V H D A A mouse p16  R E G F L D T L V V L H G S G A R L D V R D
human p16  R E G F L D T L V V L H R A G A R L D V R D
mouse p15  R E G F L D T L V V L H R A G A R L D V C D
human p15  R E G F L D T L V V L H R A G A R L D V R D mouse p16  A W G R L P L D L A Q E R G H Q D V V R Y L
human p16  A W G R L P V D L A E E L G H R D V A R Y L
mouse p15  A W G R L P V D L A E E Q G H R D I A R Y L
human p15  A W G R L P V D L A E E R G H R D V A G Y L mouse p16  R S A G C S L C S A G W S L C T A G N V A Q
human p16  R A A A G G T R G S N H A R I D A A E G P S
mouse p15  H A A T G D *
human p15  R T A T G D * mouse p16  T D G H S F S S S T P R A L E L R G Q S Q E
human p16  D I P D * mouse p16  Q S *
```

FIG. 19

SEQUENCE LISTING (1) GENERAL INFORMATION:

(iii) NUMBER OF SEQUENCES: 47

(2) INFORMATION FOR SEQ ID NO:1:

(i) SEQUENCE CHARACTERISTICS:
        (A) LENGTH: 471 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Homo sapiens (ix) FEATURE:
        (A) NAME/KEY: CDS
        (B) LOCATION: 1..471

(ix) FEATURE:
        (A) NAME/KEY: misc_feature
        (B) LOCATION: 150..151
        (D) OTHER INFORMATION: /note= "Splice site"

(ix) FEATURE:
        (A) NAME/KEY: misc_feature
        (B) LOCATION: 457..458
        (D) OTHER INFORMATION: /note= "Splice site"

(xi) SEQUENCE DESCRIPTION: SEQ ID NO:1:

```
ATG GAG CCG GCG GCG GGG AGC AGC ATG GAG CCT TCG GCT GAC TGG CTG         48
Met Glu Pro Ala Ala Gly Ser Ser Met Glu Pro Ser Ala Asp Trp Leu
  1               5                  10                  15

GCC ACG GCC GCG GCC CGG GGT CGG GTA GAG GAG GTG CGG GCG CTG CTG         96
Ala Thr Ala Ala Ala Arg Gly Arg Val Glu Glu Val Arg Ala Leu Leu
                 20                  25                  30

GAG GCG GGG GCG CTG CCC AAC GCA CCG AAT AGT TAC GGT CGG AGG CCG        144
Glu Ala Gly Ala Leu Pro Asn Ala Pro Asn Ser Tyr Gly Arg Arg Pro
             35                  40                  45

ATC CAG GTC ATG ATG ATG GGC AGC GCC CGA GTG GCG GAG CTG CTG CTG        192
Ile Gln Val Met Met Met Gly Ser Ala Arg Val Ala Glu Leu Leu Leu
 50                  55                  60

CTC CAC GGC GCG GAG CCC AAC TGC GCC GAC CCC GCC ACT CTC ACC CGA        240
Leu His Gly Ala Glu Pro Asn Cys Ala Asp Pro Ala Thr Leu Thr Arg
 65                  70                  75                  80

CCC GTG CAC GAC GCT GCC CGG GAG GGC TTC CTG GAC ACG CTG GTG GTG        288
Pro Val His Asp Ala Ala Arg Glu Gly Phe Leu Asp Thr Leu Val Val
                 85                  90                  95

CTG CAC CGG GCC GGG GCG CGG CTG GAC GTG CGC GAT GCC TGG GGC CGT        336
Leu His Arg Ala Gly Ala Arg Leu Asp Val Arg Asp Ala Trp Gly Arg
            100                 105                 110

CTG CCC GTG GAC CTG GCT GAG GAG CTG GGC CAT CGC GAT GTC GCA CGG        384
Leu Pro Val Asp Leu Ala Glu Glu Leu Gly His Arg Asp Val Ala Arg
            115                 120                 125

TAC CTG CGC GCG GCT GCG GGG GGC ACC AGA GGC AGT AAC CAT GCC CGC        432
Tyr Leu Arg Ala Ala Ala Gly Gly Thr Arg Gly Ser Asn His Ala Arg
130                 135                 140

ATA GAT GCC GCG GAA GGT CCC TCA GAC ATC CCC GAT TGA                    471
Ile Asp Ala Ala Glu Gly Pro Ser Asp Ile Pro Asp *
145                 150                 155
```

(2) INFORMATION FOR SEQ ID NO:2:

(i) SEQUENCE CHARACTERISTICS:
        (A) LENGTH: 156 amino acids
        (B) TYPE: amino acid
        (D) TOPOLOGY: linear (ii) MOLECULE TYPE: protein (xi) SEQUENCE DESCRIPTION: SEQ ID NO:2:

```
Met Glu Pro Ala Ala Gly Ser Ser Met Glu Pro Ser Ala Asp Trp Leu
  1               5                  10                  15

Ala Thr Ala Ala Ala Arg Gly Arg Val Glu Glu Val Arg Ala Leu Leu
                 20                  25                  30

Glu Ala Gly Ala Leu Pro Asn Ala Pro Asn Ser Tyr Gly Arg Arg Pro
             35                  40                  45

Ile Gln Val Met Met Met Gly Ser Ala Arg Val Ala Glu Leu Leu Leu
 50                  55                  60

Leu His Gly Ala Glu Pro Asn Cys Ala Asp Pro Ala Thr Leu Thr Arg
 65                  70                  75                  80

Pro Val His Asp Ala Ala Arg Glu Gly Phe Leu Asp Thr Leu Val Val
                 85                  90                  95

Leu His Arg Ala Gly Ala Arg Leu Asp Val Arg Asp Ala Trp Gly Arg
            100                 105                 110

Leu Pro Val Asp Leu Ala Glu Glu Leu Gly His Arg Asp Val Ala Arg
            115                 120                 125

Tyr Leu Arg Ala Ala Ala Gly Gly Thr Arg Gly Ser Asn His Ala Arg
130                 135                 140
```

Ile Asp Ala Ala Glu Gly Pro Ser Asp Ile Pro Asp
145                 150                 155

(2) INFORMATION FOR SEQ ID NO:3:

(i) SEQUENCE CHARACTERISTICS:
        (A) LENGTH: 1149 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Homo sapiens (ix) FEATURE:
        (A) NAME/KEY: 5'UTR
        (B) LOCATION: 1..866

(ix) FEATURE:
        (A) NAME/KEY: CDS
        (B) LOCATION: 867..1016

(ix) FEATURE:
        (A) NAME/KEY: intron
        (B) LOCATION: 1017..1149

(xi) SEQUENCE DESCRIPTION: SEQ ID NO:3:

```
TCCCCCGCCC GTWTTAAWTA AACCTCATCT TTCCAGAGTC TGTTCTTATA CCAGGAAATG      60

TACACGTCTG AGAAACCCTT GCCCCAGACA GTCGTTTTAC ACGCAGGAGG GGAAGGGGAG     120

GGGAAGGAGA GAGCAGTCCT TTTCTCCAAA AGGAATCCTT NGAACTAGGG TTTCTGACTT     180

AGTGAACCCC GCGYTCCTGA AAATCAWGGG TTGAGGGGGT AGGGGACAC TTYCCTAGTC      240

GYACAGSTKA TTTCGMTYCT CGGTGGGGCT CTCACAMCTA GGAAAGAATW GTTTTGCTTT     300

TTCTTATGAT TAAAAGAAGA AGCCATACTT TTCCCTATGA CACCAAACAC CCCGATTCAA     360

TTTGGCAGTT AGGAAGGTTG TATCGCGGAG GAAGGAAACG GGGCGGGGGC GGATTTCTTT     420

TTTAACAGAG TGAACGCACT CAAACACGCC TTTGCTGGCA GGCGGGGGA GCGCGGCTGG      480

GAGCAGGGGA GGCCGGAGGG CGGTGTGGGG GGCAGGTGGG GAGGAGCCCA GTCCTCCTTC    540

CTTGCCAACG CTGGCTCTGG CGAGGGCTGC TTYCGGCTGG TGCCCCCGGG GGAGACCCAA    600

CCTGGGGCGA CTTCAGGGGT GCCACATTCG CTAAGTGCTC GGAGTTAATA GCACCTCCTC    660

CGAGCACTCG CTCACAGCGT CCCCTTGCCT GGAAAGATAC CGCGGTCCCT CCAGAGGATT    720

TGAGGGACAG GGTCGGAGGG GGCTCTTCCG CCAGCACCGG AGGAAGAAAG AGGAGGGGCT    780

GGCTGGTCAC CAGAGGGTGG GGCGGACCGC GTGCGCTCGG CGGCTGCGGA GAGGGGGAGA    840

GCAGGCAGCG GGCGGCGGGG AGCAGCATGG AGCCGGCGGC GGGGAGCAGC ATGGAGCCTT    900

CGGCTGACTG GCTGGCCACG GCCGCGGCCC GGGGTCGGGT AGAGGAGGTG CGGGCGCTGC    960

TGGAGGCGGG GGCGCTGCCC AACGCACCGA ATAGTTACGG TCGGAGGCCG ATCCAGGTGG   1020

GTAGAGGGTC TGCAGCGGGA GCAGGGGATG GCGGGCGACT CTGGAGGACG AAGTTTGCAG   1080

GGGAATTGGA ATCAGGTAGC GCTTCGATTC TCCGGAAAAA GGGGAGGCTT CCTGGGGAGT   1140

TTTCAGAAC                                                           1149
```

(2) INFORMATION FOR SEQ ID NO:4:

(i) SEQUENCE CHARACTERISTICS:
        (A) LENGTH: 1187 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Homo sapiens (ix) FEATURE:
        (A) NAME/KEY: intron
        (B) LOCATION: 1..191

(ix) FEATURE:
        (A) NAME/KEY: exon
        (B) LOCATION: 192..498

(ix) FEATURE:
        (A) NAME/KEY: intron
        (B) LOCATION: 499..1187

(xi) SEQUENCE DESCRIPTION: SEQ ID NO:4:

| | | | |
|---|---|---|---|
| GAATTCATTG TGTACTGAAG AATGGATAGA GAACTCAAGA AGGAAATTGG AAACTGGAAG | 60 |
| CAAATGTAGG GGTAATTAGA CACCTGGGGC TTGTGTGGGG GTCTGCTTGG CGGTGAGGGG | 120 |
| GCTCTACACA AGCTTCCTTT CCGTCATGCC GGCCCCCACC CTGGCTCTGA CCATTCTGTT | 180 |
| CTCTCTGGCA GGTCATGATG ATGGGCAGCG CCCGAGTGGC GGAGCTGCTG CTGCTCCACG | 240 |
| GCGCGGAGCC CAACTGCGCC GACCCCGCCA CTCTCACCCG ACCCGTGCAC GACGCTGCCC | 300 |
| GGGAGGGCTT CCTGGACACG CTGGTGGTGC TGCACCGGGC CGGGGCGCGG CTGGACGTGC | 360 |
| GCGATGCCTG GGGCCGTCTG CCCGTGGACC TGGCTGAGGA GCTGGGCCAT CGCGATGTCG | 420 |
| CACGGTACCT GCGCGCGGCT GCGGGGGGCA CCAGAGGCAG TAACCATGCC CGCATAGATG | 480 |
| CCGCGGAAGG TCCCTCAGGT GAGGACTGAT GATCTGAGAA TTTGTACYCT GAGAGCTTCC | 540 |
| AAAGCTCAGA GCATTCATTT TCCAGCACAG AAAGTTCAGC CCGGGAGACC AGTCTCCGGT | 600 |
| CTTGCGCTCA GCTCACGCGC CAATGCGGTG GGACGGCCTG AGTCTCCCTA TGCGCCCTGC | 660 |
| CSCGCACAGC GCGGCAAATG GGAAATAATC CCGAAATGGA CTTGCGCACG TGAAAGCCCA | 720 |
| TTTTGTACGT TATACTTCCC AAAGCATACC ACCACCCAAA CACCTACCCT CTGCTAGTTC | 780 |
| AAGGCCTAGA CTGCGGAGCA ATGAAGACTC AAGAGGCTAG AGGTCTAGTG CCCCCTCTTC | 840 |
| CTCCAAACTA GGGCCAGTTG CATCSACTTA CCAGGTCTGT TTCCTCATTT GCATACCAAG | 900 |
| CTGGCTGGAC CAACCTCAGG ATTTCCAAAC CCAATTGTGC GTGGCATCAT CTGGAGATCT | 960 |
| CTCGATCTCG GCTCTTCTGC ACAACTCAAC TAATCTGACC CTCCTCAGCT AATCTGACCC | 1020 |
| TCCGCTTTAT GCGGTAGAGT TTTCCAGAGC TGCCCCAGGG GGTTCTGGGG ACATCAGGAC | 1080 |
| CAAGACTTCG CTGACCCTGG CAGTCTGTGC ACCGGAGTTG GCTCCTTTCC CTCTTAAACT | 1140 |
| TGTGCAAGAG ATCCCTATAG TGAGTCGTAT TATNCGGCCG CGAATTC | 1187 |

(2) INFORMATION FOR SEQ ID NO:5:

(i) SEQUENCE CHARACTERISTICS:
        (A) LENGTH: 1244 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
    (A) ORGANISM: Homo sapiens (ix) FEATURE:
    (A) NAME/KEY: intron
    (B) LOCATION: 1..273

(ix) FEATURE:
    (A) NAME/KEY: misc_RNA
    (B) LOCATION: 274..529
    (D) OTHER INFORMATION: /note= "Corresponds to exon of SEQ ID NO:4"

(xi) SEQUENCE DESCRIPTION: SEQ ID NO:5:

```
GATCATCACT TTACCATCAA CTTTCTTGTC TCTGAACGTT TAGAGAATAA AATGGCATTT    60
AATTGGTVCT GAGTWTAACC TGAAGGTGGG GTGGGAAAGT GGWTTGCATC AGCAADTGAA   120
GAAACACCAG ACATCAGAGA CCTGAACACC TCTGCACTGG GTGAAAACTT GGCAATTAGG   180
TGTTTCTTTA AATGGCTCCA CCTGCCTTGC CCCGGCCGGC ATCTCCCATA CCTGCCCCCA   240
CCCTGGCTCT GACCACTCTG CTCTCTCTGG CAGGTCATGA TGATGGGCAG CGCCCGCGTG   300
GCGGAGCTGC TGCTGCTCCA CGGCGCGGAG CCCAACTGCG CAGACCCTGC CACTCTCACC   360
CGACCGGTGC ATGATGCTGC CCGGGAGGGC TTCCTGGACA CGCTGGTGGT GCTGCACCGG   420
GCCGGGGCGC GGCTGGACGT GCGCGATGCC TGGGGTCGTC TGCCCGTGGA CTTGGCCGAG   480
GAGCGGGGCC ACCGCGACGT TGCAGGGTAC CTGCGCACAG CCACGGGGGA CTGACGCCAG   540
GTTCCCCAGC CGCCCACAAC GACTTTATTT TCTTACCCAA TTTCCCACCC CCACCCACCT   600
AATTCGATGA AGGCTGCCAA CGGGGAGCGG CGGAAAGCCT GTAAGCCTGC AAGCCTGTCT   660
GAGACTCACA GGAAGGAGGA GCCGACCGGG AATAACCTTC CATACATTTT TTTCTTTGTC   720
TTATCTGGCC CTCGACACTC ACCATGAAGC GAAACACAGA GAAGCGGATT CCAGGGATA   780
TTTAGGAGTG TGTGACATTC CAGGGGTCGT TTGNTTTTCA GGGTTTTCTG AGGGAAAGTG   840
CATATGAAAT CCTTGACTGG ACCTGGTGGC TACGAATCTT CCCGATGGAT GAATCTCCCA   900
CTCCAGCGCT GAGTGGGAGA AGGCAGTGAT TAGCACTTGG GTGACGGCAG TCGATGCGTT   960
CACTCCAATG TCTGCTGAGG AGTTATGGTG AACCCACAAC TTAGGCCCTA GCGGCAGAAA  1020
GGAAAACCTG AAGACTGAGG ACAAAGTGGA GGAGGGCCGA GGTGGGCTTC AGTATGTCCC  1080
CNNCGGCGCT TTAGTTTGAG CGCATGGCAA GTCACATGCG TAAACGACAC TCTCTGGAAG  1140
CCCTGGAGAC CCTCGCCCAA CTCCACCAGA TAGCAGAGGG GTAAGAGAGG ATGTGCAAGC  1200
GACGACAGAT GCTAAAATCC CTGGATCACG ACGCTGCAGA GCAC                  1244
```

(2) INFORMATION FOR SEQ ID NO:6:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Homo sapiens (xi) SEQUENCE DESCRIPTION: SEQ ID NO:6:

CAGCACCGGA GGAAGAAAG                                                          19

(2) INFORMATION FOR SEQ ID NO:7:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: YES (vi) ORIGINAL SOURCE:
            (A) ORGANISM: Homo sapiens (xi) SEQUENCE DESCRIPTION: SEQ ID NO:7:

GCGCTACCTG ATTCCAATTC                                                         20

(2) INFORMATION FOR SEQ ID NO:8:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
            (A) ORGANISM: Homo sapiens (xi) SEQUENCE DESCRIPTION: SEQ ID NO:8:

GGAAATTGGA AACTGGAAGC                                                         20

(2) INFORMATION FOR SEQ ID NO:9:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: YES (vi) ORIGINAL SOURCE:
            (A) ORGANISM: Homo sapiens (xi) SEQUENCE DESCRIPTION: SEQ ID NO:9:

TCTGAGCTTT GGAAGCTCT                                                          19

(2) INFORMATION FOR SEQ ID NO:10:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
             (A) ORGANISM: Homo sapiens (xi) SEQUENCE DESCRIPTION: SEQ ID NO:10:

GATCATCACT TTACCATCAA C                                                       21

(2) INFORMATION FOR SEQ ID NO:11:

(i) SEQUENCE CHARACTERISTICS:
             (A) LENGTH: 19 base pairs
             (B) TYPE: nucleic acid
             (C) STRANDEDNESS: single
             (D) TOPOLOGY: linear (ii) MOLECULE TYPE: DNA (genomic)

(iii) HYPOTHETICAL: NO (iv) ANTI-SENSE: YES (vi) ORIGINAL SOURCE:
             (A) ORGANISM: Homo sapiens (xi) SEQUENCE DESCRIPTION: SEQ ID NO:11:

GGGTGGGAAA TTGGGTAAG                                                          19

(2) INFORMATION FOR SEQ ID NO:12:

(i) SEQUENCE CHARACTERISTICS:
             (A) LENGTH: 20 base pairs
             (B) TYPE: nucleic acid
             (C) STRANDEDNESS: single
             (D) TOPOLOGY: linear (ii) MOLECULE TYPE: DNA (genomic)

(iii) HYPOTHETICAL: NO (iv) ANTI-SENSE: NO (vi) ORIGINAL SOURCE:
             (A) ORGANISM: Homo sapiens (xi) SEQUENCE DESCRIPTION: SEQ ID NO:12:

TGAGTTTAAC CTGAAGGTGG                                                         20

(2) INFORMATION FOR SEQ ID NO:13:

(i) SEQUENCE CHARACTERISTICS:
             (A) LENGTH: 1131 base pairs
             (B) TYPE: nucleic acid
             (C) STRANDEDNESS: double
             (D) TOPOLOGY: linear (ii) MOLECULE TYPE: cDNA (iii) HYPOTHETICAL: NO (iv) ANTI-SENSE: NO (vi) ORIGINAL SOURCE:
             (A) ORGANISM: Homo sapiens (ix) FEATURE:
             (A) NAME/KEY: CDS
             (B) LOCATION: 338..655

(xi) SEQUENCE DESCRIPTION: SEQ ID NO:13:

```
CGCGCCTGCG GGGCGGAGAT GGGCAGGGGG CGGTGCGTGG GTCCCAGTCT GCAGTTAAGG      60

GGGCAGGAGT GGCGCTGCTC ACCTCTGGTG CCAAAGGGCG GCGCAGCGGC TGCCGAGCTC     120

GGCCCTGGAG GCGGCGAGAA CATGGTGCGC AGGTTCATGG TGACCCTCCG GATTCGGCGC     180

GCGTGCGGAC CGCCGCGAGT GAGGGTTTTC GTGGTTCACA TCCCGCGGCT CACGGGGGAG     240

TGGGCAGCGC CAGGGGCGCC CGCCGCTGTG GCCCTCGTGC TGATGCTACT GAGGAGCCAG     300

CGTCTAGGGC AGCAGCCGCT TCCTAGAAGA CCAGGTC ATG ATG ATG GGC AGC GCC      355
                                         Met Met Met Gly Ser Ala
                                                         160
```

```
CGA GTG GCG GAG CTG CTG CTG CTC CAC GGC GCG GAG CCC AAC TGC GCC      403
Arg Val Ala Glu Leu Leu Leu Leu His Gly Ala Glu Pro Asn Cys Ala
165                 170                 175

GAC CCC GCC ACT CTC ACC CGA CCC GTG CAC GAC GCT GCC CGG GAG GGC      451
Asp Pro Ala Thr Leu Thr Arg Pro Val His Asp Ala Ala Arg Glu Gly
180                 185                 190                 195

TTC CTG GAC ACG CTG GTG GTG CTG CAC CGG GCC GGG GCG CGG CTG GAC      499
Phe Leu Asp Thr Leu Val Val Leu His Arg Ala Gly Ala Arg Leu Asp
                200                 205                 210

GTG CGC GAT GCC TGG GGC CGT CTG CCC GTG GAC CTG GCT GAG GAG CTG      547
Val Arg Asp Ala Trp Gly Arg Leu Pro Val Asp Leu Ala Glu Glu Leu
            215                 220                 225

GGC CAT CGC GAT GTC GCA CGG TAC CTG CGC GCG GCT GCG GGG GGC ACC      595
Gly His Arg Asp Val Ala Arg Tyr Leu Arg Ala Ala Ala Gly Gly Thr
        230                 235                 240

AGA GGC AGT AAC CAT GCC CGC ATA GAT GCC GCG GAA GGT CCC TCA GAC      643
Arg Gly Ser Asn His Ala Arg Ile Asp Ala Ala Glu Gly Pro Ser Asp
    245                 250                 255

ATC CCC GAT TGA AAGAACCAGA GAGGCTCTGA GAAACCTCGG GAAACTTAGA          695
Ile Pro Asp *
260
```

```
TCATCAGTCA CCGAAGGTCC TACAGGGCCA CAACTGCCCC CGCCACAACC CACCCCGCTT     755

TCGTAGTTTT CATTTAGAAA ATAGAGCTTT TAAAAATGTC CTGCCTTTTA ACGTAGATAT     815

AAGCCTTCCC CCACTACCGT AAATGTCCAT TTATATCATT TTTTATATAT TCTTATAAAA     875

ATGTAAAAAA GAAAACACCC GCTTCTGCCT TTTCACTGTG TTGGAGTTTT CTGGAGTGAG     935

CACTCACGCC CTAAGCGCAC ATTCATGTGG GCATTTCTTG CGAGCCTCGC AGCCTCCGGA     995

AGCTGTCGAC TTCATGACAA GCATTTTGTG AACTAGGGAA GCTCAGGGGG GTTACTGGCT    1055

TCTCTTGAGT CACACTGCTA GCAAATGGCA GAACCAAAGC TCAAATAAAA ATAAAATTAT    1115

TTTCATTCAT TCACTC                                                    1131
```

(2) INFORMATION FOR SEQ ID NO:14:

(i) SEQUENCE CHARACTERISTICS:
        (A) LENGTH: 105 amino acids
        (B) TYPE: amino acid
        (D) TOPOLOGY: linear (ii) MOLECULE TYPE: protein (xi) SEQUENCE DESCRIPTION: SEQ ID NO:14:

```
Met Met Met Gly Ser Ala Arg Val Ala Glu Leu Leu Leu Leu His Gly
  1               5                  10                  15

Ala Glu Pro Asn Cys Ala Asp Pro Ala Thr Leu Thr Arg Pro Val His
                20                  25                  30
```

```
Asp Ala Ala Arg Glu Gly Phe Leu Asp Thr Leu Val Val Leu His Arg
         35                  40                  45

Ala Gly Ala Arg Leu Asp Val Arg Asp Ala Trp Gly Arg Leu Pro Val
 50                  55                  60

Asp Leu Ala Glu Glu Leu Gly His Arg Asp Val Ala Arg Tyr Leu Arg
65                  70                  75                  80

Ala Ala Ala Gly Gly Thr Arg Gly Ser Asn His Ala Arg Ile Asp Ala
                 85                  90                  95

Ala Glu Gly Pro Ser Asp Ile Pro Asp
            100                 105

(2) INFORMATION FOR SEQ ID NO:15:

(i) SEQUENCE CHARACTERISTICS:
        (A) LENGTH: 751 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Homo sapiens (ix) FEATURE:
        (A) NAME/KEY: CDS
        (B) LOCATION: 335..751

(ix) FEATURE:
        (A) NAME/KEY: misc_feature
        (B) LOCATION: 490..491
        (D) OTHER INFORMATION: /note= "Splice site"

(xi) SEQUENCE DESCRIPTION: SEQ ID NO:15:
```

```
CGGGCAGTGA GGACTCCGCG ACGCGTCCGC ACCCTGCGGC CAGAGCGGCT TTGAGCTCGG      60

CTGCGTCCGC GCTAGGCGCT TTTTCCCAGA AGCAATCCAG GCGCGCCCGC TGGTTCTTGA     120

GCGCCAGGAA AAGCCCGGAG CTAACGACCG GCCGCTCGGC CACTGCACGG GGCCCCAAGC     180

CGCAGAAGGA CGACGGGAGG GTAATGAAGC TGAGCCCAGG TCTCCTAGGA AGGAGAGAGT     240

GCGCCGGAGC AGCGTGGGAA AGAAGGGAAG AGTGTCGTTA AGTTTACGGC CAACGGTGGA     300

TTATCCGGGC CGCTGCGCGT CTGGGGGCTG CGGA ATG CGC GAG GAG AAC AAG         352
                                      Met Arg Glu Glu Asn Lys
                                                            110

GGC ATG CCC AGT GGG GGC GGC AGC GAT GAG GGT CTG GCC AGC GCC GCG       400
Gly Met Pro Ser Gly Gly Gly Ser Asp Glu Gly Leu Ala Ser Ala Ala
           115                 120                 125

GCG CGG GGA CTA GTG GAG AAG GTG CGA CAG CTC CTG GAA GCC GGC GCG       448
Ala Arg Gly Leu Val Glu Lys Val Arg Gln Leu Leu Glu Ala Gly Ala
130                 135                 140

GAT CCC AAC GGA GTC AAC CGT TTC GGG AGG CGC GCG ATC CAG GTC ATG       496
Asp Pro Asn Gly Val Asn Arg Phe Gly Arg Arg Ala Ile Gln Val Met
145                 150                 155                 160

ATG ATG GGC AGC GCC CGC GTG GCG GAG CTG CTG CTG CTC CAC GGC GCG       544
Met Met Gly Ser Ala Arg Val Ala Glu Leu Leu Leu Leu His Gly Ala
                165                 170                 175

GAG CCC AAC TGC GCA GAC CCT GCC ACT CTC ACC CGA CCG GTG CAT GAT       592
Glu Pro Asn Cys Ala Asp Pro Ala Thr Leu Thr Arg Pro Val His Asp
            180                 185                 190

GCT GCC CGG GAG GGC TTC CTG GAC ACG CTG GTG GTG CTG CAC CGG GCC       640
```

```
Ala Ala Arg Glu Gly Phe Leu Asp Thr Leu Val Val Leu His Arg Ala
            195                 200                 205

GGG GCG CGG CTG GAC GTG CGC GAT GCC TGG GGT CGT CTG CCC GTG GAC      688
Gly Ala Arg Leu Asp Val Arg Asp Ala Trp Gly Arg Leu Pro Val Asp
210                 215                 220

TTG GCC GAG GAG CGG GGC CAC CGC GAC GTT GCA GGG TAC CTG CGC ACA      736
Leu Ala Glu Glu Arg Gly His Arg Asp Val Ala Gly Tyr Leu Arg Thr
225                 230                 235                 240

GCC ACG GGG GAC TGA                                                  751
Ala Thr Gly Asp  *
                245
```

(2) INFORMATION FOR SEQ ID NO:16:

(i) SEQUENCE CHARACTERISTICS:
        (A) LENGTH: 138 amino acids
        (B) TYPE: amino acid
        (D) TOPOLOGY: linear (ii) MOLECULE TYPE: protein (xi) SEQUENCE DESCRIPTION: SEQ ID NO:16:

```
Met Arg Glu Glu Asn Lys Gly Met Pro Ser Gly Gly Ser Asp Glu
 1               5                  10                  15

Gly Leu Ala Ser Ala Ala Ala Arg Gly Leu Val Glu Lys Val Arg Gln
                20                  25                  30

Leu Leu Glu Ala Gly Ala Asp Pro Asn Gly Val Asn Arg Phe Gly Arg
                35                  40                  45

Arg Ala Ile Gln Val Met Met Met Gly Ser Ala Arg Val Ala Glu Leu
            50                  55                  60

Leu Leu Leu His Gly Ala Glu Pro Asn Cys Ala Asp Pro Ala Thr Leu
65                  70                  75                  80

Thr Arg Pro Val His Asp Ala Ala Arg Glu Gly Phe Leu Asp Thr Leu
                85                  90                  95

Val Val Leu His Arg Ala Gly Ala Arg Leu Asp Val Arg Asp Ala Trp
                100                 105                 110

Gly Arg Leu Pro Val Asp Leu Ala Glu Glu Arg Gly His Arg Asp Val
            115                 120                 125

Ala Gly Tyr Leu Arg Thr Ala Thr Gly Asp
        130                 135
```

(2) INFORMATION FOR SEQ ID NO:17:

(i) SEQUENCE CHARACTERISTICS:
        (A) LENGTH: 57 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Homo sapiens (xi) SEQUENCE DESCRIPTION: SEQ ID NO:17:

```
AAAGGATCCA TTGCCACCAT GGAGCCGGCG GCGGGGAGCA GCATGGAGCC TTCGGCT      57
```

(2) INFORMATION FOR SEQ ID NO:18:

```
    (i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (vi) ORIGINAL SOURCE:
        (A) ORGANISM: Homo sapiens (xi) SEQUENCE DESCRIPTION: SEQ ID NO:18:

TTTGAATTCA ATCGGGGATG TCTG                                              24

(2) INFORMATION FOR SEQ ID NO:19:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Homo sapiens (xi) SEQUENCE DESCRIPTION: SEQ ID NO:19:

AGGGAAGAGT GTCGTTAAG                                                    19

(2) INFORMATION FOR SEQ ID NO:20:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (vi) ORIGINAL SOURCE:
        (A) ORGANISM: Homo sapiens (xi) SEQUENCE DESCRIPTION: SEQ ID NO:20:

AGACTCCTGT ACAAATCTAC                                                   20

(2) INFORMATION FOR SEQ ID NO:21:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
```

(A) ORGANISM: Homo sapiens (xi) SEQUENCE DESCRIPTION: SEQ ID NO:21:

TGAGGGTCTG GCCAGC                                                        16

(2) INFORMATION FOR SEQ ID NO:22:

(i) SEQUENCE CHARACTERISTICS:
         (A) LENGTH: 17 base pairs
         (B) TYPE: nucleic acid
         (C) STRANDEDNESS: single
         (D) TOPOLOGY: linear (ii) MOLECULE TYPE: DNA (genomic)

(iii) HYPOTHETICAL: NO (iv) ANTI-SENSE: YES (vi) ORIGINAL SOURCE:
         (A) ORGANISM: Homo sapiens (xi) SEQUENCE DESCRIPTION: SEQ ID NO:22:

AGCACCACCA GCGTGTC                                                       17

(2) INFORMATION FOR SEQ ID NO:23:

(i) SEQUENCE CHARACTERISTICS:
         (A) LENGTH: 16 base pairs
         (B) TYPE: nucleic acid
         (C) STRANDEDNESS: single
         (D) TOPOLOGY: linear (ii) MOLECULE TYPE: DNA (genomic)

(iii) HYPOTHETICAL: NO (iv) ANTI-SENSE: YES (vi) ORIGINAL SOURCE:
         (A) ORGANISM: Homo sapiens (xi) SEQUENCE DESCRIPTION: SEQ ID NO:23:

CGTGTCCAGG AAGCCC                                                        16

(2) INFORMATION FOR SEQ ID NO:24:

(i) SEQUENCE CHARACTERISTICS:
         (A) LENGTH: 144 base pairs
         (B) TYPE: nucleic acid
         (C) STRANDEDNESS: double
         (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:24:

AATTCGGCAC GAGGCAGCAT GGAGCCTTCG GCTGACTGGC TGGCCACGGC CGCGGCCCGG         60

GGTCGGGTAG AGGAGGTGCG GGCGCTGCTG GAGGCGGTGG CGCTGCCCAA CGCACCGAAT        120

AGTTACGGTC GGAGGCCGAT CCAG                                              144

(2) INFORMATION FOR SEQ ID NO:25:

(i) SEQUENCE CHARACTERISTICS:
         (A) LENGTH: 395 base pairs
         (B) TYPE: nucleic acid (C) STRANDEDNESS: double
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:25:

AAGAGAGGGT TTTCTTGGTA AAGTTCGTGC GATCCCGGAG ACCCAGGACA GCGTAGCTGC    60

GCTCTGGCTT TCGTGAACAT GTTGTTGAGG CTAGAGAGGA TCTTGAGAAG AGGGCCGCAC   120

CGGAATCCTG GACCAGGTGA TGATGATGGG CAACGTTCAC GTAGCAGCTC TTCTGCTCAA   180

CTACGGTGCA GATTCGAACT GCGAGGACCC CACTACCTTC TCCCGCCCGG TGCACGACGC   240

AGCGCGCGAA GGCTTCCTGG ACACGCTGGT GGTGCTGCAC GGGTCAGGGG CTCGGCTGGA   300

TGTCCGCGAT GCCTGGGGTC GCCTCCCGCT CGACTTCGCC CAAGAGCGGG GACATCAAGA   360

CATCGTGCGA TATTTGCGTT CCGCTGGGTG CTCTT                              395

(2) INFORMATION FOR SEQ ID NO:26:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (xi) SEQUENCE DESCRIPTION: SEQ ID NO:26:

CAACGCACCG AATAGTTACG                                                20

(2) INFORMATION FOR SEQ ID NO:27:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (xi) SEQUENCE DESCRIPTION: SEQ ID NO:27:

TACTGAGGAG CCAGCGTCTA                                                20

(2) INFORMATION FOR SEQ ID NO:28:

(i) SEQUENCE CHARACTERISTICS:
        (A) LENGTH: 30 base pairs
        (B) TYPE: nucleic acid
        (C) STRANDEDNESS: double
        (D) TOPOLOGY: linear (ii) MOLECULE TYPE: other nucleic acid (xi) SEQUENCE DESCRIPTION: SEQ ID NO:28:

TGAGTAGAAT TCTAACGGCC GTCATTGTTC                                     30

(2) INFORMATION FOR SEQ ID NO:29:

(i) SEQUENCE CHARACTERISTICS:
        (A) LENGTH: 20 base pairs (B) TYPE: nucleic acid
      (C) STRANDEDNESS: single
      (D) TOPOLOGY: linear (ii) MOLECULE TYPE: cDNA (iii) HYPOTHETICAL: NO (xi) SEQUENCE DESCRIPTION: SEQ ID NO:29:

AGCGTGTCCA GGAAGCCTTC                                              20

(2) INFORMATION FOR SEQ ID NO:30:

(i) SEQUENCE CHARACTERISTICS:
      (A) LENGTH: 27 base pairs
      (B) TYPE: nucleic acid
      (C) STRANDEDNESS: single
      (D) TOPOLOGY: linear (ii) MOLECULE TYPE: other nucleic acid (xi) SEQUENCE DESCRIPTION: SEQ ID NO:30:

TGAGTAGAAT TCTAACGGCC GTCATTG                                      27

(2) INFORMATION FOR SEQ ID NO:31:

(i) SEQUENCE CHARACTERISTICS:
      (A) LENGTH: 26 base pairs
      (B) TYPE: nucleic acid
      (C) STRANDEDNESS: single
      (D) TOPOLOGY: linear (ii) MOLECULE TYPE: cDNA (iii) HYPOTHETICAL: NO (xi) SEQUENCE DESCRIPTION: SEQ ID NO:31:

ACTGCGAGGA CCCCACTACC TTCTCC                                       26

(2) INFORMATION FOR SEQ ID NO:32:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ii) MOLECULE TYPE: cDNA (iii) HYPOTHETICAL: NO (xi) SEQUENCE DESCRIPTION: SEQ ID NO:32:

GAACGTTGCC CATCATCATC                                              20

(2) INFORMATION FOR SEQ ID NO:33:

(i) SEQUENCE CHARACTERISTICS:
      (A) LENGTH: 15 base pairs
      (B) TYPE: nucleic acid
      (C) STRANDEDNESS: single
      (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:33:

AGTCTGCAGT TAAGG                                                   15

(2) INFORMATION FOR SEQ ID NO:34:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO:34:

```
GGCTAGAGGC GAATTATCTG T                                          21
```

(2) INFORMATION FOR SEQ ID NO:35:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO:35:

```
CACCAAACAA AACAAGTGCC G                                          21
```

(2) INFORMATION FOR SEQ ID NO:36:

(i) SEQUENCE CHARACTERISTICS:
        (A) LENGTH: 947 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Homo sapiens (ix) FEATURE:
        (A) NAME/KEY: misc_feature
        (B) LOCATION: 151
        (D) OTHER INFORMATION: /note= "Splice site acceptor."

(ix) FEATURE:
        (A) NAME/KEY: misc_feature
        (B) LOCATION: 458
        (D) OTHER INFORMATION: /note= "Splice site acceptor."

(xi) SEQUENCE DESCRIPTION: SEQ ID NO:36:

```
ATGGAGCCGG CGGCGGGGAG CAGCATGGAG CCTTCGGCTG ACTGGCTGGC CACGGCCGCG    60

GCCCGGGGTC GGGTAGAGGA GGTGCGGGCG CTGCTGGAGG CGGGGGCGCT GCCCAACGCA   120

CCGAATAGTT ACGGTCGGAG GCCGATCCAG GTCATGATGA TGGGCAGCGC CCGAGTGGCG   180

GAGCTGCTGC TGCTCCACGG CGCGGAGCCC AACTGCGCCG ACCCCGCCAC TCTCACCCGA   240

CCCGTGCACG ACGCTGCCCG GGAGGGCTTC CTGGACACGC TGGTGGTGCT GCACCGGGCC   300
```

```
GGGGCGCGGC TGGACGTGCG CGATGCCTGG GGCCGTCTGC CCGTGGACCT GGCTGAGGAG       360

CTGGGCCATC GCGATGTCGC ACGGTACCTG CGCGCGGCTG CGGGGGGCAC CAGAGGCAGT       420

AACCATGCCC GCATAGATGC CGCGGAAGGT CCCTCAGACA TCCCCGATTG AAAGAACCAG       480

AGAGGCTCTG AGAAACCTCG GGAAACTTAG ATCATCAGTC ACCGAAGGTC CTACAGGGCC       540

ACAACTGCCC CCGCCACAAC CCACCCCGCT TTCGTAGTTT TCATTTAGAA AATAGAGCTT       600

TTAAAAATGT CCTGCCTTTT AACGTAGATA TAAGCCTTCC CCCACTACCG TAAATGTCCA       660

TTTATATCAT TTTTTATATA TTCTTATAAA AATGTAAAAA AGAAAAACAC CGCTTCTGCC       720

TTTTCACTGT GTTGGAGTTT TCTGGAGTGA GCACTCACGC CCTAAGCGCA CATTCATGTG       780

GGCATTTCTT GCGAGCCTCG CAGCCTCCGG AAGCTGTCGA CTTCATGACA AGCATTTTGT       840

GAACTAGGGA AGCTCAGGGG GGTTACTGGC TTCTCTTGAG TCACACTGCT AGCAAATGGC       900

AGAACCAAAG CTCAAATAAA AATAAAATTA TTTTCATTCA TTCACTC                    947
```

(2) INFORMATION FOR SEQ ID NO:37:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Degenerate PCR primer"

(iii) HYPOTHETICAL: NO (xi) SEQUENCE DESCRIPTION: SEQ ID NO:37:

```
CCCGGGAATT CGARCCNAAY GCNGAYCC                                          28
```

(2) INFORMATION FOR SEQ ID NO:38:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Degenerate PCR primer"

(iii) HYPOTHETICAL: NO (xi) SEQUENCE DESCRIPTION: SEQ ID NO:38:

```
CTGCAGGATC CCCANGCRTC NCKNACRTC                                         29
```

(2) INFORMATION FOR SEQ ID NO:39:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic biotinylated
            oligomer"

(iii) HYPOTHETICAL: NO (xi) SEQUENCE DESCRIPTION: SEQ ID NO:39:

```
AACTGCGCCG ACCCTGCCAC CCTTACC                                           27
```

(2) INFORMATION FOR SEQ ID NO:40:

(i) SEQUENCE CHARACTERISTICS:
              (A) LENGTH: 20 base pairs
              (B) TYPE: nucleic acid
              (C) STRANDEDNESS: single
              (D) TOPOLOGY: linear (ii) MOLECULE TYPE: other nucleic acid
              (A) DESCRIPTION: /desc = "Synthetic oligomer"

(iii) HYPOTHETICAL: NO (xi) SEQUENCE DESCRIPTION: SEQ ID NO:40:

TGGGCGCTGC CCATCATCAT                                                      20

(2) INFORMATION FOR SEQ ID NO:41:

(i) SEQUENCE CHARACTERISTICS:
              (A) LENGTH: 20 base pairs
              (B) TYPE: nucleic acid
              (C) STRANDEDNESS: single
              (D) TOPOLOGY: linear (ii) MOLECULE TYPE: other nucleic acid
              (A) DESCRIPTION: /desc = "Synthetic oligomer"

(xi) SEQUENCE DESCRIPTION: SEQ ID NO:41:

GTAGTGCAAG GCTCGAGAAC                                                      20

(2) INFORMATION FOR SEQ ID NO:42:

(i) SEQUENCE CHARACTERISTICS:
              (A) LENGTH: 18 base pairs
              (B) TYPE: nucleic acid
              (C) STRANDEDNESS: single
              (D) TOPOLOGY: linear (ii) MOLECULE TYPE: other nucleic acid
              (A) DESCRIPTION: /desc = "Synthetic oligomer"

(xi) SEQUENCE DESCRIPTION: SEQ ID NO:42:

GGGCTCGGCT GGATGTCC                                                        18

(2) INFORMATION FOR SEQ ID NO:43:

(i) SEQUENCE CHARACTERISTICS:
              (A) LENGTH: 18 base pairs
              (B) TYPE: nucleic acid
              (C) STRANDEDNESS: single
              (D) TOPOLOGY: linear (ii) MOLECULE TYPE: other nucleic acid
              (A) DESCRIPTION: /desc = "Synthetic oligomer"

(iii) HYPOTHETICAL: NO (xi) SEQUENCE DESCRIPTION: SEQ ID NO:43:

CAAGAGCGGG GACATCAA                                                        18

(2) INFORMATION FOR SEQ ID NO:44:

(i) SEQUENCE CHARACTERISTICS:
              (A) LENGTH: 507 base pairs
              (B) TYPE: nucleic acid
              (C) STRANDEDNESS: double
              (D) TOPOLOGY: linear (ii) MOLECULE TYPE: cDNA (iii) HYPOTHETICAL: NO (iv) ANTI-SENSE: NO (vi) ORIGINAL SOURCE:
            (A) ORGANISM: Mus musculus (ix) FEATURE:
            (A) NAME/KEY: misc_feature
            (B) LOCATION: 126..127
            (D) OTHER INFORMATION: /note= "Splice site"

(ix) FEATURE:
            (A) NAME/KEY: misc_feature
            (B) LOCATION: 467..468
            (D) OTHER INFORMATION: /note= "Splice site"

(xi) SEQUENCE DESCRIPTION: SEQ ID NO:44:

```
ATGGAGTCCG CTGCAGACAG ACTGGCCAGG GCGGCGGCCC AGGGCCGTGT GCCTGACGTG      60

AGGGCACTGC TGGAAGCCGG GGTTTCGCCC AACGCCCCGA ACTCTTTCGG TCGTACCCCG     120

ATTCAGGTGA TGATGATGGG CAACGTTCAC GTAGCAGCTC TTCTGCTCAA CTACGGTGCA     180

GATTCGAACT GCGAGGACCC CACTACCTTC TCCCGCCCGG TGCACGACGC AGCGCGCGAA     240

GGCTTCCTGG ACACGCTGGT GGTGCTGCAC GGGTCAGGGG CTCGGCTGGA TGTGCGCGAT     300

GCCTGGGGTC GCCTCCCGCT CGACTTGGCC CAAGAGCGGG GACATCAAGA CATCGTGCGA     360

TATTTGCGTT CCGCTGGGTG CTCTTTGTGT TCCGCTGGGT GGTCTTTGTG TACCGCTGGG     420

AACGTCGCCC AGACCGACGG GCATAGCTTC AGCTCAAGCA CGCCCAGGGC CCTGGAACTT     480

CGCGGCCAAT CCCAAGAGCA GAGCTAA                                        507
```

(2) INFORMATION FOR SEQ ID NO:45:

(i) SEQUENCE CHARACTERISTICS:
            (A) LENGTH: 393 base pairs
            (B) TYPE: nucleic acid
            (C) STRANDEDNESS: double
            (D) TOPOLOGY: linear (ii) MOLECULE TYPE: cDNA (iii) HYPOTHETICAL: NO (iv) ANTI-SENSE: NO (vi) ORIGINAL SOURCE:
            (A) ORGANISM: Mus musculus (ix) FEATURE:
            (A) NAME/KEY: misc_feature
            (B) LOCATION: 132..133
            (D) OTHER INFORMATION: /note= "Splice site"

(xi) SEQUENCE DESCRIPTION: SEQ ID NO:45:

```
ATGTTGGGCG GCAGCAGTGA CGCGGGCCTG GCCACCGCCG CGGCGCGGGG GCAAGTGGAG      60

ACGGTGCGGC AACTCCTGGA AGCCGGCGCA GATCCCAACG CCCTGAACCG CTTCGGGAGG     120

CGCCCAATCC AGGTCATGAT GATGGGCAGC GCCCAGGTGG CAGAGCTGCT GCTGCTCCAC     180

GGAGCAGAAC CCAACTGCGC CGACCCTGCC ACCCTTACCA GACCTGTGCA CGACGCAGCT     240

CGGGAAGGCT TCCTGGACAC GCTTGTCGTG CTGCACCGGG CAGGGCGCG GCTGGATGTG     300

TGTGACGCCT GGGGCCGCCT GCCGGTAGAC TTGGCTGAAG AGCAGGGCCA CCGTGACATT     360

GCGAGGTATC TGCACGCTGC CACTGGAGAT TGA                                  393
```

(2) INFORMATION FOR SEQ ID NO:46:

(i) SEQUENCE CHARACTERISTICS:
            (A) LENGTH: 168 amino acids

```
        (B) TYPE: amino acid
        (C) STRANDEDNESS: single
        (D) TOPOLOGY: linear (ii) MOLECULE TYPE: protein (iii) HYPOTHETICAL: NO (vi) ORIGINAL SOURCE:
        (A) ORGANISM: Mus musculus (xi) SEQUENCE DESCRIPTION: SEQ ID NO:46:

Met Glu Ser Ala Ala Asp Arg Leu Ala Arg Ala Ala Gln Gly Arg
1               5                  10                  15

Val Pro Asp Val Arg Ala Leu Leu Glu Ala Gly Val Ser Pro Asn Ala
            20                  25                  30

Pro Asn Ser Phe Gly Arg Thr Pro Ile Gln Val Met Met Met Gly Asn
            35                  40                  45

Val His Val Ala Ala Leu Leu Asn Tyr Gly Ala Asp Ser Asn Cys
        50                  55                  60

Glu Asp Pro Thr Thr Phe Ser Arg Pro Val His Asp Ala Ala Arg Glu
65                  70                  75                  80

Gly Phe Leu Asp Thr Leu Val Val Leu His Gly Ser Gly Ala Arg Leu
                85                  90                  95

Asp Val Arg Asp Ala Trp Gly Arg Leu Pro Leu Asp Leu Ala Gln Glu
                100                 105                 110

Arg Gly His Gln Asp Ile Val Arg Tyr Leu Arg Ser Ala Gly Cys Ser
            115                 120                 125

Leu Cys Ser Ala Gly Trp Ser Leu Cys Thr Ala Gly Asn Val Ala Gln
        130                 135                 140

Thr Asp Gly His Ser Phe Ser Ser Thr Pro Arg Ala Leu Glu Leu
145                 150                 155                 160

Arg Gly Gln Ser Gln Glu Gln Ser
                165

(2) INFORMATION FOR SEQ ID NO:47:

(i) SEQUENCE CHARACTERISTICS:
        (A) LENGTH: 130 amino acids
        (B) TYPE: amino acid
        (C) STRANDEDNESS: single
        (D) TOPOLOGY: linear (ii) MOLECULE TYPE: protein (iii) HYPOTHETICAL: NO (vi) ORIGINAL SOURCE:
        (A) ORGANISM: Mus musculus (xi) SEQUENCE DESCRIPTION: SEQ ID NO:47:

Met Leu Gly Gly Ser Ser Asp Ala Gly Leu Ala Thr Ala Ala Arg
1               5                   10                  15

Gly Gln Val Glu Thr Val Arg Gln Leu Leu Glu Ala Gly Ala Asp Pro
            20                  25                  30

Asn Ala Leu Asn Arg Phe Gly Arg Arg Pro Ile Gln Val Met Met Met
            35                  40                  45

Gly Ser Ala Gln Val Ala Glu Leu Leu Leu His Gly Ala Glu Pro
        50                  55                  60

Asn Cys Ala Asp Pro Ala Thr Leu Thr Arg Pro Val His Asp Ala Ala
65                  70                  75                  80
```

-continued

```
Arg Glu Gly Phe Leu Asp Thr Leu Val Val Leu His Arg Ala Gly Ala
                85                  90                  95

Arg Leu Asp Val Cys Asp Ala Trp Gly Arg Leu Pro Val Asp Leu Ala
            100                 105                 110

Glu Glu Gln Gly His Arg Asp Ile Ala Arg Tyr Leu His Ala Ala Thr
        115                 120                 125

Gly Asp
    130
```

MOUSE MTS2 GENE

CROSS REFERENCE TO RELATED APPLICATIONS

The present invention is a divisional of application Ser. No. 08/508,735, filed Jul. 28, 1995, now U.S. Pat. No. 5,843,756 which is a continuation-in-part of application Ser. No. 08/487,033, filed Jun. 7, 1995, now U.S. Pat. No. 5,739,027, which is a continuation-in-part of application Ser. No. PCT/US95/03316, filed Mar. 7, 1995 which are incorporated herein by reference.

BACKGROUND OF THE INVENTION

The present invention relates to the Multiple Tumor Suppressor (MTS) genes in mice and to somatic mutations in the Multiple Tumor Suppressor gene in human cancers and their use in the diagnosis and prognosis of human cancer. The invention further relates to germline mutations in the MTS gene and their use in the diagnosis of predisposition to cancer, such as melanoma, ocular melanoma, leukemia, astrocytoma, glioblastoma, lymphoma, glioma, Hodgkin's lymphoma, multiple myeloma, sarcoma, myosarcoma, cholangiocarcinoma, squamous cell carcinoma, CLL, and cancers of the pancreas, breast, brain, prostate, bladder, thyroid, ovary, uterus, testis, kidney, stomach, colon and rectum. The invention also relates to the therapy of human cancers which have a mutation in the MTS gene, including gene therapy, protein replacement therapy and protein mimetics. The invention also relates to the screening of drugs for cancer therapy. Finally, the invention relates to mouse MTS genes corresponding the human MTS genes.

The publications and other materials used herein to illuminate the background of the invention, and in particular, cases to provide additional details respecting the practice, are incorporated herein by reference, and for convenience are referenced in the following text and respectively grouped in the appended List of References.

The genetics of cancer is complicated, involving multiple dominant, positive regulators of the transformed state (oncogenes) as well as multiple recessive, negative regulators (tumor suppressor genes). Over one hundred oncogenes have been characterized. Fewer than a dozen tumor suppressor genes have been identified, but the number is expected to increase beyond fifty (Knudson, 1993).

The involvement of so many genes underscores the complexity of the growth control mechanisms that operate in cells to maintain the integrity of normal tissue. This complexity is manifested in another way. So far, no single gene has been shown to participate in the development of all, or even the majority of human cancers. The most common oncogenic mutations are in the H-ras gene, found in 10–15% of all solid tumors (Anderson et al., 1992). The most frequently mutated tumor suppressor gene is the p53 gene, mutated in roughly 50% of all tumors. Without a target that is common to all transformed cells, the dream of a "magic bullet" that can destroy or revert cancer cells while leaving normal tissue unharmed is improbable. The hope for a new generation of specifically targeted antitumor drugs may rest on the ability to identify tumor suppressor genes or oncogenes that play general roles in control of cell division.

The tumor suppressor genes, which have been cloned and characterized, influence susceptibility to: 1) retinoblastoma (RB1); 2) Wilms' tumor (WT1); 3) Li-Fraumeni (TP53); 4) Familial adenomatous polyposis (APC); 5) Neurofibromatosis type 1 (NF1); 6) Neurofibromatosis type 2 (NF2); 7) von Hippel-Lindau syndrome (VHL); and 8) Multiple endocrine neoplasia type 2A (MEN2A).

Tumor suppressor loci that have been mapped genetically but not yet isolated include genes for: Multiple endocrine neoplasia type 1 (MEN1); Lynch cancer family syndrome 2 (LCFS2); Familial breast cancer (BRCA1); Neuroblastoma (NB); Basal cell nevus syndrome (BCNS); Beckwith-Wiedemann syndrome (BWS); Renal cell carcinoma (RCC); Tuberous sclerosis 1 (TSC1); and Tuberous sclerosis 2 (TSC2). The tumor suppressor genes that have been characterized to date encode products with similarities to a variety of protein types, including DNA binding proteins (WT1), ancillary transcription regulators (RB1), GTPase activating proteins or GAPs (NF1), cytoskeletal components (NF2), membrane bound receptor kinases (MEN2A), and others with no obvious similarity to known proteins (APC and VHL).

In many cases, the tumor suppressor gene originally identified through genetic studies has been shown in some sporadic tumors to be lost or mutated. This result suggests that regions of chromosomal aberration may signify the position of important tumor suppressor genes involved both in genetic predisposition to cancer and in sporadic cancer.

One of the hallmarks of several tumor suppressor genes characterized to date is that they are deleted at high frequency in certain tumor types. The deletions often involve loss of a single allele, a so-called loss of heterozygosity (LOH), but may also involve homozygous deletion of both alleles. For LOH, the remaining allele is presumed to be nonfunctional, either because of a preexisting inherited mutation, or because of a secondary sporadic mutation.

Melanoma is a common cancer afflicting one in every hundred Americans (American Cancer Society, 1992). Environmental influences, such as exposure to ultraviolet light, play a large role in melanoma incidence, but heredity is also a contributing factor. A gene for familial melanoma, MLM, has been mapped to chromosome 9p21 (Cannon-Albright et al., 1992; Nancarrow et al., 1993; Gruis et al., 1993; Goldstein et al., 1994). Possession of a single predisposing allele at the MLM locus increases the probability that an individual will develop melanoma by up to approximately 50-fold. MLM belongs to the growing family of suspected tumor suppressor genes. Predisposition to melanoma is inherited as a dominant Mendelian trait, yet predisposing mutations in MLM are thought to act as somatic recessive alleles in the manner originally proposed by Knudson (1971). In a predisposed individual who carries one wild-type and one mutant MLM allele, dividing cells undergo secondary mutational events that involve loss or inactivation of the wild-type copy of MLM, thereby uncovering the inherited mutant MLM allele. Conversely, a single wild-type copy of the gene prevents the onset of malignancy.

Chromosomal aberrations in the vicinity of MLM at 9p21 have been extensively characterized in several different tumor types, including glioma cell lines, non-small cell lung lines and acute lymphoblastic leukemia lines (Olopade et al., 1992; Olopade et al., 1993; Lukeis et al., 1990; Diaz et al., 1988; Middleton et al., 1991; Fountain et al., 1992; Cheng et al., 1993; James et al., 1993). Thus, based on the frequency of 9p21 chromosomal abnormalities in non-melanoma tumor cells, it is probable the MLM region contains a gene (or genes) that participates at least in the progression of several different tumor types. These events involve LOH as well as a high frequency of homozygous deletion.

Cells in tissues have only three serious options in life—they can grow and divide, not grow but stay alive, or die by apoptosis. Tumors may arise either by inappropriate growth and division or by cells failing to die when they should. One of the mechanisms for controlling tumor growth might involve direct regulation of the cell cycle. For example, genes that control the decision to initiate DNA replication are attractive candidates for oncogenes or tumor suppressor genes, depending on whether they have a stimulatory or inhibitory role in the process. Progression of eukaryotic cells through the cell cycle ($G_1$, S, $G_2$ and M phases) is governed by the sequential formation, activation and subsequent inactivation of a series of cyclin/cyclin-dependent kinase (Cdk) complexes. Cyclin D's/Cdk2,4,5, Cyclin E/Cdk2, Cyclin A/Cdk2 and Cyclin B/A/Cdk2 have been shown to be involved in this process. Cyclin D's and Cdk2, Cdk4 and Cdk5 have been implicated in the transition from $G_1$ to S; that is, when cells grow and decide whether to begin DNA replication. Additional cell cycle control elements have recently been discovered. These elements are inhibitors of Cdks (Cdk inhibitors, CkI), and include Far1, p21, p40, p20 and p16. (Marx, 1994; Nasmyth & Hunt, 1993).

Recently, several oncogenes and tumor suppressor genes have been found to participate directly in the cell cycle. For example, one of the cyclins (proteins that promote DNA replication) has been implicated as an oncogene (Motokura et al., 1991; Lammie et al., 1991; Withers et al., 1991; Rosenberg et al., 1991), and tumor suppressor Rb interacts with the primary cyclin-binding partners, the Cdks (Ewen et al., 1993). Identification of a melanoma susceptibility locus would open the way for genetic screening of individuals to assess, for example, the increased risk of cancer due to sunlight exposure. The MTS may also predispose to a large number of other cancer sites, including but not limited to, leukemia, astrocytoma, glioblastoma, lymphoma, glioma, Hodgkin's lymphoma, multiple myeloma, sarcoma, myosarcoma, cholangiocarcinoma, squamous cell carcinoma, CLL, and cancers of the pancreas, breast, brain, prostate, bladder, thyroid, ovary, uterus, testis, kidney, stomach, colon and rectum. In addition, since MTS influences progression of several different tumor types, it should be useful for determining prognosis in cancer patients. Thus, MTS may serve as the basis for development of very important diagnostic tests, one capable of predicting the predisposition to cancer, such as melanoma, ocular melanoma, leukemia, astrocytoma, glioblastoma, lymphoma, glioma, Hodgkin's lymphoma, multiple myeloma, sarcoma, myosarcoma, cholangiocarcinoma, squamous cell carcinoma, CLL, and cancers of the pancreas, breast, brain, prostate, bladder, thyroid, ovary, uterus, testis, kidney, stomach, colon and rectum, and one capable of predicting the prognosis of cancer. Furthermore, since MTS is involved in the progression of multiple tumor types, MTS may provide the means, either directly or indirectly, for a general anti-cancer therapy by virtue of its ability to suppress tumor growth. For example, restoration of the normal MTS function to a tumor cell may transmute the cell into non-malignancy.

SUMMARY OF THE INVENTION

The present invention relates to mouse Multiple Tumor Suppressor (MTS) genes. These genes are homologous to corresponding human MTS genes. Somatic mutations in MTS genes result in human cancers. MTS genes can be used in the diagnosis and prognosis of cancer. The invention further relates to germline mutations in the MTS gene and their use in the diagnosis of predisposition to many cancers, such as melanoma, ocular melanoma, leukemia, astrocytoma, glioblastoma, lymphoma, glioma, Hodgkin's lymphoma, multiple myeloma, sarcoma, myosarcoma, cholangiocarcinoma, squamous cell carcinoma, CLL, and cancers of the pancreas, breast, brain, prostate, bladder, thyroid, ovary, uterus, testis, kidney, stomach, colon and rectum. The invention also relates to the therapy of human cancers which have a mutation in the MTS gene, including gene therapy, protein replacement therapy and protein mimetics. Finally, the invention relates to the screening of drugs for cancer therapy.

BRIEF DESCRIPTION OF THE DRAWINGS

FIGS. 5A and 5B show a comparison of the genomic sequence containing a 5' untranslated region, exon 1, and part of intron 1 for human MTS1 with the published sequence for p16 (Serrano et al., 1993). The start codon (underlined) is located at position 867 and a splice site (arrow) at position 1016. The MTS1 sequence shown in FIGS. 5A–B is SEQ ID NO:3. The p16 sequence shown in FIG. 5B is SEQ ID NO:24.

FIGS. 6A and 6B show a comparison of the genomic sequence containing part of intron 1, exon 2 and part of intron 2 for human MTS1, with the published sequence for p16 (Serrano et al., 1993). Splice sites (arrows) are located before position 192 and after position 498. The human MTS1 sequence shown in FIGS. 6A–B is SEQ ID NO:4. The p16 sequence shown in FIG. 6A is identical to nucleotides 192–498 of SEQ ID NO:4.

FIGS. 7A and 7B show a comparison of the genomic sequence containing part of intron 1, "exon 2," and follow-through sequences for human MTS2 with the published p16 sequence. The "Exon 2" sequence is similar to exon 2 of human MTS1 from nucleotides 273 to 580. The splice site in MTS2, and those in p16, are shown by arrows. The point where divergence begins is indicated by °. The termination codon for MTS2 is present in exon 2 at position 532 and is indicated by an "*". The MTS2 sequence shown in FIGS. 7A–B is SEQ ID NO:5. The p16 sequence shown in FIG. 7A is identical to nucleotides 192–498 of SEQ ID NO:4.

FIG. 8 shows a comparison of the human MTS1 and MTS2 DNA sequences including exon 2 and part of each surrounding intron. The positions of the 3' splice junction of intron 1 and the 5' splice junction of intron 2 for MTS1 are shown by triangles. The divergence point near the 3' end of coding exon 2 is indicated by an arrow. The MTS1 sequence shown corresponds to nucleotides 92–548 of SEQ ID NO:4. The MTS2 sequence shown corresponds to nucleotides 174–630 of SEQ ID NO:5.

FIG. 9 shows deletions in tumor cell lines of various STSs. Positive controls and negative controls were included in every PCR experiment and cell lines in which only one or two of the STSs were deleted (e.g., class 21) were retested at least twice.

FIG. 10A shows the relative level of MTS2 transcript in RNA (Clonetech) derived from various human tissues: lane 1—brain; lane 2—breast; lane 3—kidney; lane 4—lung; lane 5—lymphocyte; lane 6—ovary; lane 7—pancreas; lane 8—prostate; lane 9—spleen; lane 10—stomach; lane 11—thymus. The origins of products with different than expected molecular weights (see lane 1) are unknown. FIG. 10B shows the relative human MTS2 transcript level in human lymphocytes as a function of time after mitogenic induction: lane 1—0 hours; lane 2—1 hour; lane 3—2 hours; lane 4—4 hours; lane 5—8 hours; lane 6—16 hours; lane 7—24 hours; lane 8—32 hours; lane 9—40 hours; lane 10—48 hors; lane 11—56 hours; lane 12— 64 hours. A majority of the cells were in S phase 40–50 hours after induction. FIG. 10C shows MTS2 transcript level as a function of Rb status. The Rb$^-$ cell lines are: Lane 1—WERI; lane 2—CaSki; lane 3—SiHa; lane 4—C33A; lane 5—5637; lane 6—MDA MB 468. The Rb$^+$ cell lines are: lane 7—T24; lane 8—HaCaT; lane 9—ZR75; lane 10—Bristol 8; lane 11—UMSCC2; lane 12—diploid human fibroblast MRC5, passage 28; lane 13—KIT (Hori et al., 1987).

FIG. 11 shows the cDNA sequence (and the encoded polypeptide) for human MTS2 including 5'-untranslated region. The beginning of exon 2 is located at position 491 and is indicated by an arrow. The cDNA sequence is shown as SEQ ID NO:15 and the amino acid sequence is shown as SEQ ID NO:16.

FIGS. 12A and 12B show the cDNA sequence (and the encoded polypeptide) of human MTS1E1β. Splice sites are indicated by arrows. Exon 2 begins at position 335 and exon 3 begins at position 642. The cDNA sequence is shown as SEQ ID NO:13 and the amino acid sequence is shown by SEQ ID NO:14.

FIG. 14 shows the alignment between mouse and human P16 β transcript sequences. Capital letters indicate identical nucleotides. The stop codons in the p16 reading frame are underlined. The splice junction between E1β and E2 is indicated with a caret (v). The mouse β sequence is shown as SEQ ID NO:25. The human β sequence is identical to nucleotides 193–461 of SEQ ID NO: 13.

In FIGS. 16A and 16D the α and β reactions from a common sample were mixed prior to electrophoresis. FIG. 16A shows the relative levels of P16 transcripts in RNA derived from various human tissues: lane 1, brain; lane 2, breast; lane 3, kidney; lane 4, lung; lane 5, lymphocyte; lane 6, ovary; lane 7, pancreas; lane 8, prostate; lane 9, spleen; lane 10, stomach; lane 11, thymus. FIG. 16B shows the relative amount of the β transcript in human lymphocytes as a function of time after mitogenic induction: lane 1, 0 hours;

lane 2, 1 hour; lane 3, 2 hours; lane 4, 4 hours; lane 5, 8 hours; lane 6, 16 hours; lane 7, 24 hours; lane 8, 32 hours; lane 9, 40 hours; lane 10, 48 hours; lane 11, 56 hours; lane 12, 64 hours. FIG. 16C shows the relative amount of the α transcript in human lymphocytes as a function of time after mitogenic induction: Lanes, same as in FIG. 16B, but the 1 hour time point was omitted. The expression of other molecules that are either suspected to influence cell-cycle progression or that are regulated at the transcriptional level during the cell-cycle was also analyzed. In agreement with previous results, levels of CDK4 and GoS 2 (a molecule of unknown function, but whose transcription is induced when quiescent T cells enter the cell cycle) increased upon T cell induction (Russell and Forsdyke, 1991; Matsushime et al., 1992; Geng and Weinberg, 1993). In contrast, the RNA levels of p27 appeared unchanged during the course of the experiment (Toyoshima and Hunter, 1994; Kato et al., 1994). FIG. 16D shows P16 transcripts as a function of Rb status. Rb⁻ cell lines: lane 1, WERI; lane 2, CaSki; lane 3, SiHa; lane 4, C33A; lane 5, 5637; lane 6, MDA MB 468. Rb⁺ cell lines: lane 7, T24; lane 8, HaCaT; lane 9, Zr75; lane 10, Bristol 8; lane 11, UMSCC2; lane 12, diploid human fibroblast MRC5, passage 28; lane 13, KIT (Hori et al., 1987).

FIG. 17 shows the cDNA sequence for human MTS1 including noncoding portions of the cDNA. The triangles indicate splice junctions. The dashes in the sequence at the second splice junction only emphasize this splice junction, they do not indicate missing bases. This sequence is SEQ ID NO:36.

Figure 18A:
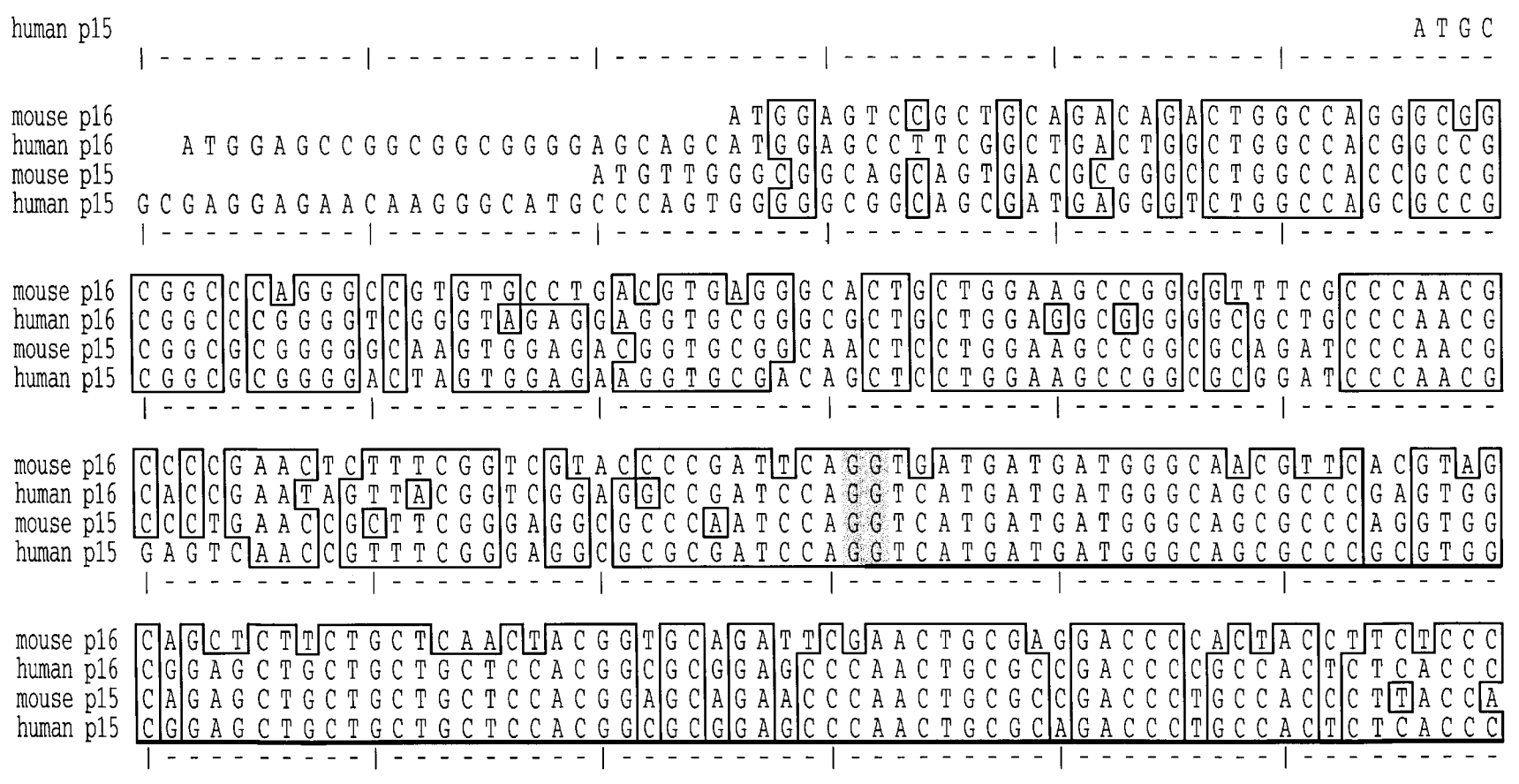
Figure 18B:
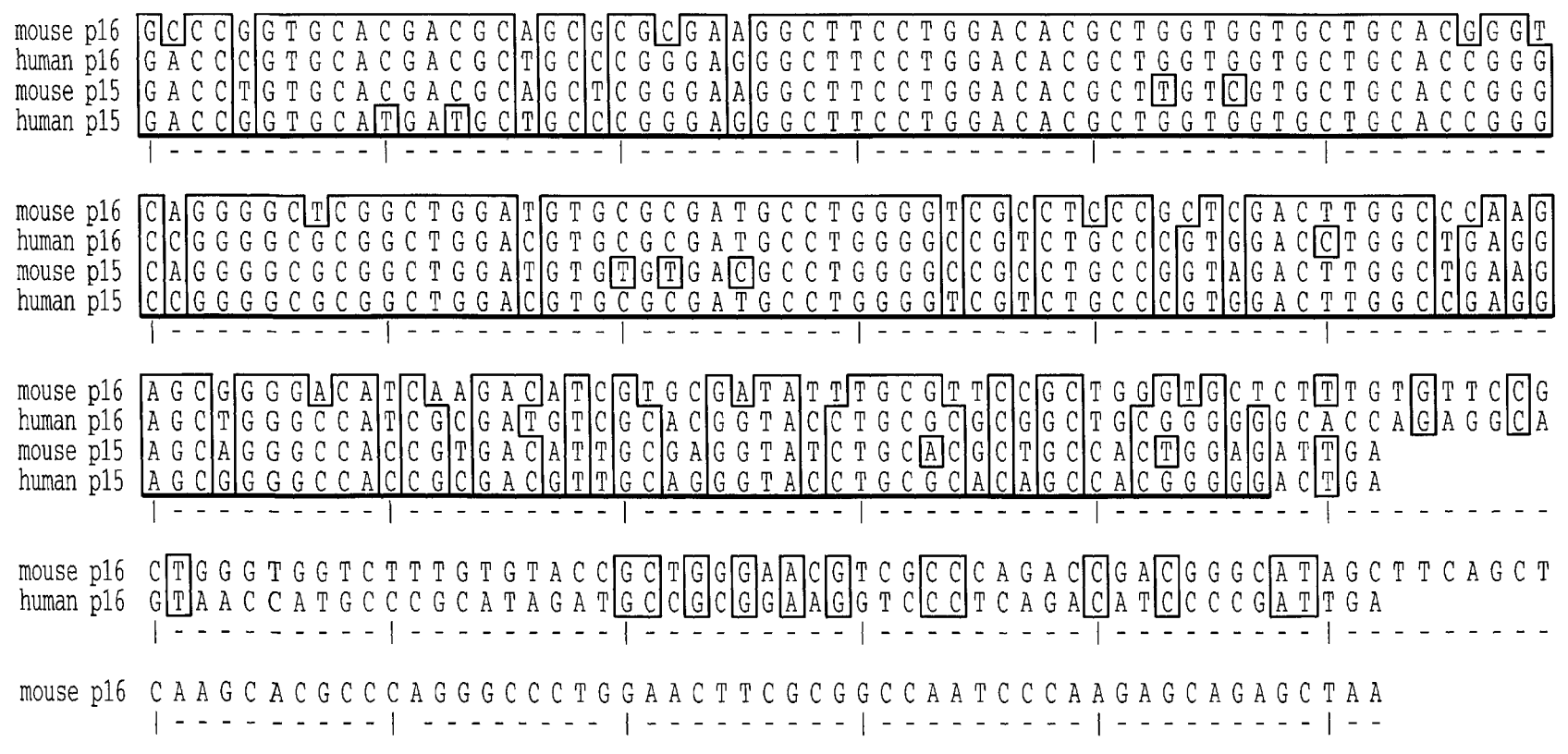

FIGS. 18A and 18B show the alignments of primary sequences of *M. musculus* and human MTS2 (p15) and MTS1 (p16) coding sequences beginning with their predicted initiation codons. Splice sites are indicated by shading of the 2 nucleotides that flank the junction. The boxes indicate residue identities. The mouse p16 is SEQ ID NO:44, the human p16 is SEQ ID NO:1, the mouse p15 is SEQ ID NO:45, and the human p15 is bases 335–751 of SEQ ID NO:15.

FIG. 19 shows the alignments of predicted peptide sequences of *M. musculus* and human MTS2 (p15) and MTS1 (p16). The asterisks (*) indicate termination codons. Shading defines the 4 segments of ankyrin homology. The mouse p16 is SEQ ID NO:46, human p16 is SEQ ID NO:2, mouse p15 is SEQ ID NO:47, and human p15 is SEQ ID NO:16.

DETAILED DESCRIPTION OF THE INVENTION

Figure 1A:
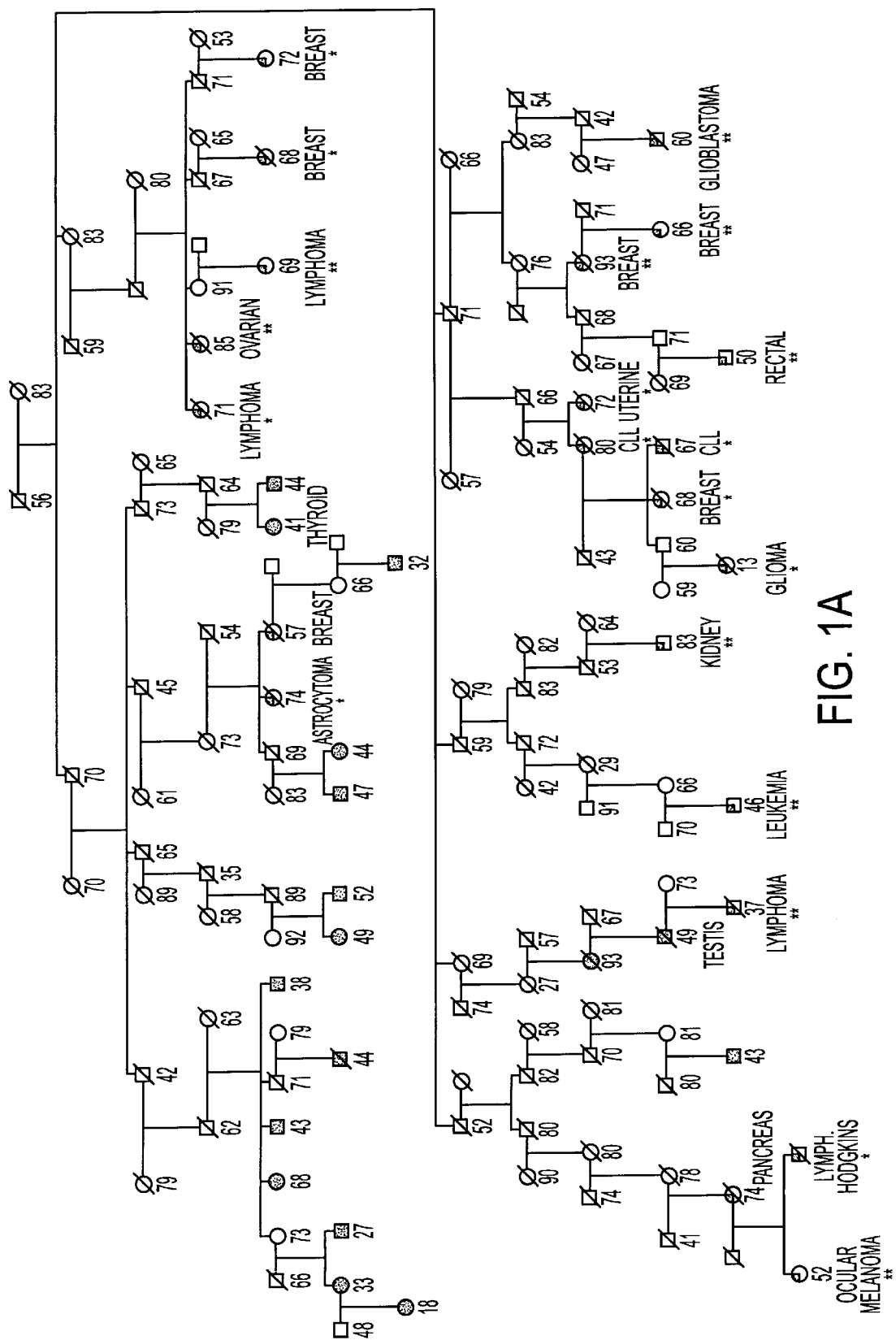
FIG. 1A shows Kindred 3137. All melanoma cases carry the susceptible haplotype. Other cancers in individuals carrying the susceptible haplotypes are also shown. The legends are as follows: filled circle or square indicates melanoma; partially filled circle or square indicates other cancer; "/" indicates deceased; "*" indicates that individual is unknown with regard to susceptible haplotype; "**" indicates that individual appears to carry susceptible haplotype; and "35" indicates age of exam or diagnosis if affected.
Figure 1B:
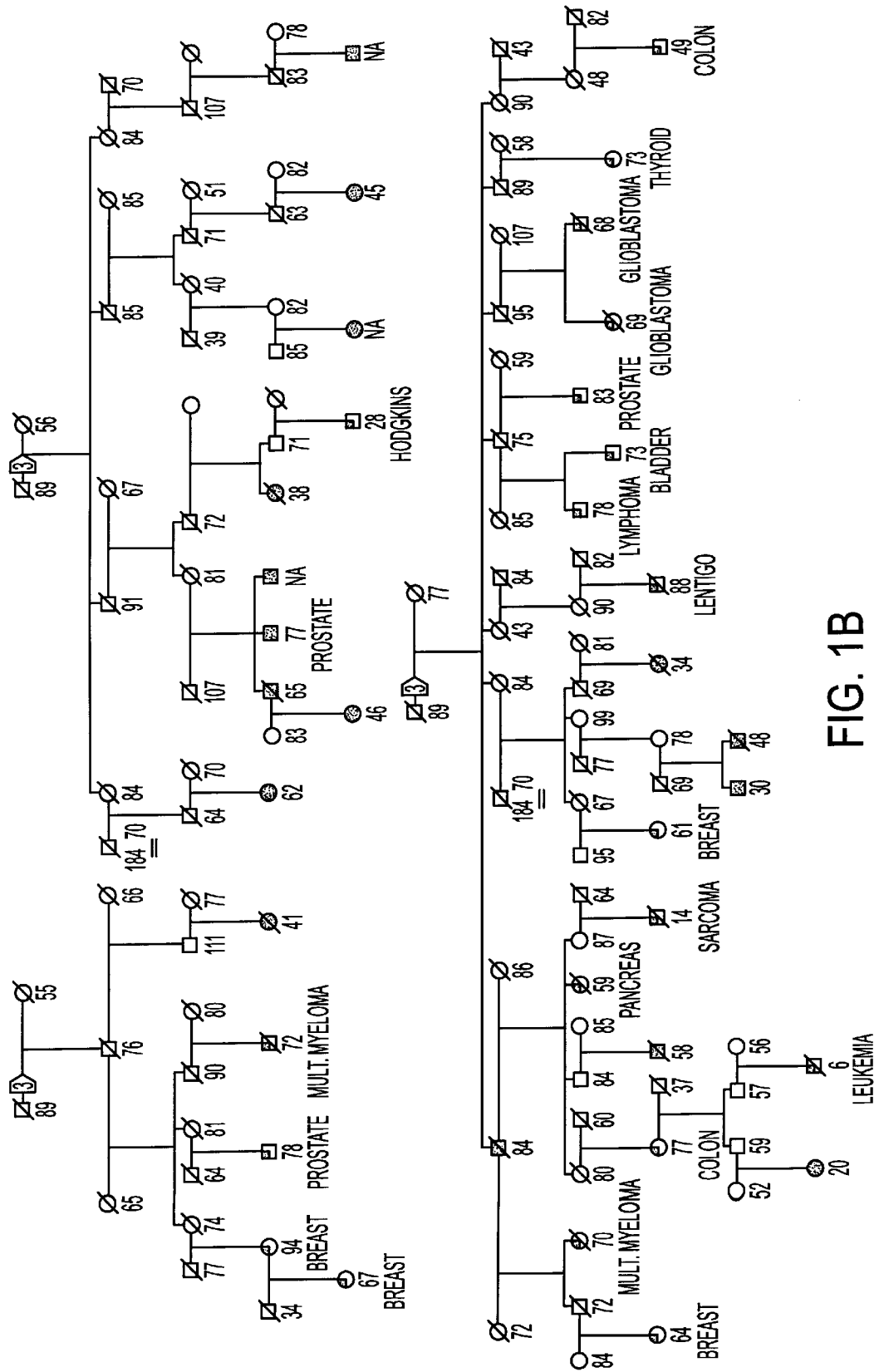
FIG. 1B shows Kindred 3161. All melanoma cases carry the susceptible haplotype. Other cancers have not been haplotyped. The legends are as follows: filled circle or square indicates melanoma; partially filled circle or square indicates other cancer; "/" indicates deceased; "=" indicates appears elsewhere in kindred; "3" in pentagon indicates multiple marriage; and "35" indicates age of exam or diagnosis if affected.
Figure 1C:
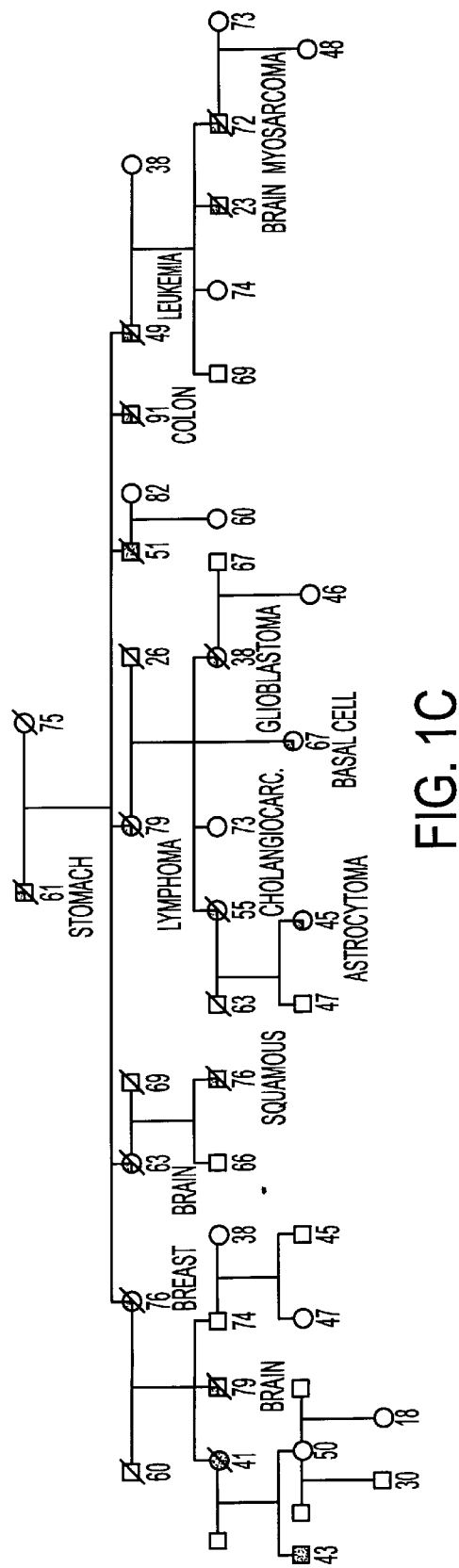
FIG. 1C shows Kindred 3355. All melanoma cases carry the susceptible haplotype. Other cancers have not been haplotyped. The legends are as follows: filled circle or square indicates melanoma; partially filled circle or square indicates other cancer; "/" indicates deceased; and "35" indicates age of exam or diagnosis if affected.
Figure 1D:
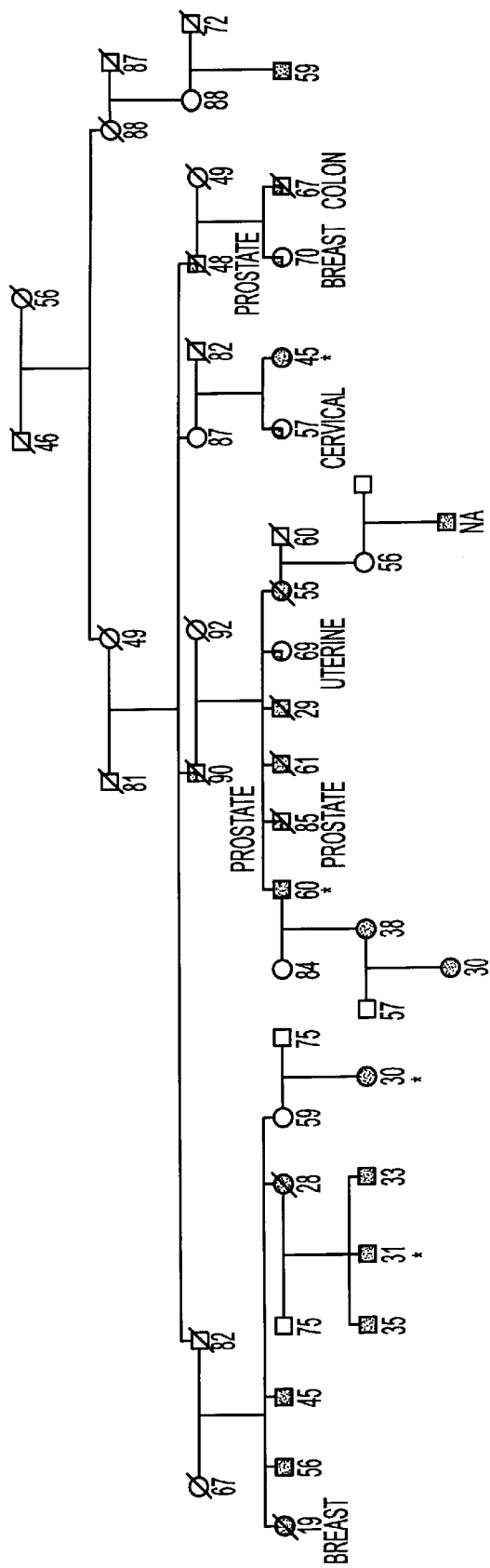
FIG. 1D shows Kindred 1771 and the occurrence of melanoma and other cancers. A mutation was identified in MTS in this kindred. The legends are as follows: an "*" indicates a confirmed mutation carrier; filled circle or square indicates melanoma; partially filled circle or square indicates other cancer (colon in this kindred); "/" indicates deceased; and "35" indicates age of exam or diagnosis if affected.

The present invention relates to the Multiple Tumor Suppressor (MTS) genes in mice. This knowledge of the mouse genes allows for further understanding of and research into the corresponding human genes. Knowledge of the mouse genes allows one to perform "knockout" studies or other mutational studies whereby the mouse genes are inactivated. This allows one to determine what effect the MTS genes have in normal mice. Furthermore, by combining knockout or other gene inactivation studies and transfer of the corresponding human MTS genes into mice it is possible to use such genetically altered mice to screen drugs which affect the human MTS genes or gene products. The human MTS genes are involved in human cancers. This invention relates to MTS genes and their use in the diagnosis and prognosis of human cancer. The invention further relates to germ line mutations in the MTS gene and their use in the diagnosis of predisposition to various cancers, such as melanoma, ocular melanoma, leukemia, astrocytoma, glioblastoma, lymphoma, glioma, Hodgkin's lymphoma, multiple myeloma, sarcoma, myosarcoma, cholangiocarcinoma, squamous cell carcinoma, CLL, and cancers of the pancreas, breast, brain, prostate, bladder, thyroid, ovary, uterus, testis, kidney, stomach, colon and rectum. The invention also relates to the therapy of human cancers which have a mutation in the MTS gene, including gene therapy, protein replacement therapy and protein mimetics. Finally, the invention relates to the screening of drugs for cancer therapy.

The present invention provides an isolated polynucleotide comprising all, or a portion of the MTS locus or of a mutated MTS locus, preferably at least eight bases and not more than about 100 Kb in length. Such polynucleotides may be antisense polynucleotides. The present invention also provides a recombinant construct comprising such an isolated polynucleotide, for example, a recombinant construct suitable for expression in a transformed host cell.

Also provided by the present invention are methods of detecting a polynucleotide comprising a portion of the MTS locus or its expression product in an analyte. Such method may further comprise the step of amplifying the portion of the MTS locus, and may further include a step of providing a set of polynucleotides which are primers for amplification of said portion of the MTS locus. The method is useful for either diagnosis of the predisposition to cancer or the diagnosis or prognosis of cancer.

The present invention also provides isolated antibodies, preferably monoclonal antibodies, which specifically bind to an isolated polypeptide comprised of at least five amino acid residues encoded by the MTS locus.

The present invention also provides kits for detecting in an analyte a polynucleotide comprising a portion of the MTS locus, the kits comprising a polynucleotide complementary to the portion of the MTS locus packaged in a suitable container, and instructions for its use.

The present invention further provides methods of preparing a polynucleotide comprising polymerizing nucleotides to yield a sequence comprised of at least eight consecutive nucleotides of the MTS locus; and methods of preparing a polypeptide comprising polymerizing amino acids to yield a sequence comprising at least five amino acids encoded within the MTS locus.

In addition, the present invention provides methods of screening drugs for cancer therapy to identify suitable drugs for restoring MTS gene product function.

Finally, the present invention provides the means necessary for production of gene-based therapies directed at cancer cells. These therapeutic agents may take the form of polynucleotides comprising all or a portion of the MTS locus placed in appropriate vectors or delivered to target cells in more direct ways such that the function of the MTS protein is reconstituted. Therapeutic agents may also take the form of polypeptides based on either a portion of, or the entire protein sequence of MTS. These may functionally replace the activity of MTS in vivo.

It is a discovery of the present invention that the MTS locus (referred to in the prior art as Melanoma (MLM) locus), which predisposes individuals to melanoma and other cancers, is a gene encoding MTS 1, which has been found to be an inhibitor of Cdks, particularly Cdk4. This gene is termed MTS1 herein. It is also a discovery of the present invention that the MTS locus contains a second coding sequence, termed MTS2, which is very similar to MTS1 over part of its sequence. It is also a discovery of the present invention that the MTS1 gene has two separate promoters—α and β. When the α promoter is used the resulting mRNA is composed of exon 1α, exon 2 and exon 3. This is referred to as MTS1. When the β promoter is used the resulting mRNA is composed of exon 1β, exon 2 and exon 3. This is referred to as MTS1E1β. It is a discovery of the present invention that mutations in the MTS locus in the germline are indicative of a predisposition to melanoma and to other cancers. Finally, it is a discovery of the present invention that somatic mutations in the MTS locus are associated with most, if not all tumor types, and thus represent a general indicator of cancer or of prognosis of cancer. The mutational events of the MTS locus can involve deletions, insertions and point mutations within the coding sequence and the non-coding sequence.

The MLM locus was first located genetically by showing dramatic linkage in several Utah kindreds and one Texas kindred between genetic markers and melanoma predisposition (Cannon-Albright, 1992). The region defined by recombinants in the kindreds is flanked by D9S736 and D9S171. Subsequently, these and other genetic markers were used to localize the gene by analysis of homozygous deletions in both melanoma and non-melanoma tumor cell lines containing deletions. The minimum area of overlap of the deletions was flanked by IFNA-s and D9S171. YAC libraries were screened to identify genomic clones surrounding these markers. P1 clones were isolated as part of a chromosomal walk and were contiguous from IFNA-s to D9S171 except for two gaps. Specific sequence-tagged sites ("STS") were prepared to construct a more detailed molecular map. Using these markers and a deletion analysis, a region of deletion overlap centered around markers c5.1 and c5.3, markers found on cosmid 5 (c5). The most frequently deleted marker was c5.3, which thus was very close to MTS.

An analysis of c5 for the presence of "CpG" islands showed that it contained at least one candidate gene for MTS. DNA sequences of EcoRI fragments of c5 were determined and compared against sequences from GenBank. Two distinct regions of c5 were identified that were similar to a region of a previously identified gene encoding human Cdk4 inhibitor, or p16 (Serrano et al., 1993). These two candidate genes are called MTS1 and MTS2. Screening cDNA libraries of lymphocyte, fetal brain and normal breast with a probe from Exon 2 of MTS1 identified an additional candidate called MTS1E1β.

A detailed comparison of the genomic sequence from c5 with the p16 mRNA sequence revealed that MTS1 contained a stretch of 307 bp that was identical to a portion of the p16 coding sequence. This stretch of nucleotides in MTS1 was flanked by recognizable splice junction sequences. Further characterization of MTS1 showed that it included the entire coding sequence of p16 plus two introns. Intron 1 was located 126 bp downstream from the translational start site; Intron 2 was located 11 bp upstream from the translational stop site. The two introns divided the coding sequence of p16 into three regions, a 5' region of 126 bp (coding Exon 1), a middle region of 307 bp (coding Exon 2), and a 3' region of 11 bp (coding Exon 3).

MTS2 contained a region of DNA sequences nearly identical to p16 that extended from the 5' end of coding Exon 2 roughly 200 bp toward intron 2. However, the sequence similarity decreased to a point 51 bp upstream of Intron 2 in MTS1, where the two sequences diverged completely. This corresponds to the location of the final codon of MTS2. Comparison of sequences from MTS1 and MTS2 showed that the sequence similarity between these two genes also extended nearly 50 nucleotides upstream from the 3' splice junction of intron 1. Thus, portions of noncoding DNA were more conserved than some areas of presumptive coding DNA. To exclude the possibility that the sequence divergence in coding DNA might be a cloning artifact, PCR primers were designed to amplify specifically across the sequence divergence point of MTS2. These primers amplified a fragment of the predicted size from cosmid P1 and genomic DNA. Therefore, the divergent sequence located near the 3' end of Exon 2 in MTS2 is a bona fide genomic sequence.

MTS1E1β contains an Exon 1, called Exon 1β or E1β, which has a different sequence than found in Exon 1 of MTS1 and MTS2. MTS1E1β also contains Exon 2 (E2) and Exon 3 (E3) which are identical to Exons 2 and 3 of MTS1. Exon 1β is located upstream of Exon 1 of MTS1 and does not contain any coding sequence. As a result MTS1E1β encodes a p10 which has a translation start site at the first ATG of Exon 2.

MTS1 and MTS2 were tested for correspondence with the genetic susceptibility locus MTS by analyzing genomic DNA, using Exon 2, from individuals presumed to carry MLM predisposing alleles. DNA polymorphisms were identified in Exon 2 of MTS1 in one of eight individuals. The mutation was a single nucleotide substitution, resulting in an amino acid change. This polymorphism segregated with the MLM predisposing allele.

The preponderance of lesions in MTS1 (deletions and nucleotide substitutions) indicates that MTS1 or a closely linked locus contributes to the tumor phenotype. Cells that suffer these lesions enjoy a selective advantage over cells that do not. The alternative explanation, that the lesions are random events having nothing to do with cell growth, is unlikely for several reasons. First, the high correlation between tumor phenotype and mutation at MTS1 implies a causal relation between MTS1 mutations and tumor formation. Second, MTS1 influences susceptibility to melanoma, and thus is implicated independently as a tumor suppressor gene. Third, the biochemical function of p16 as a potent inhibitor of a Cdk neatly fits a model where MTS1 acts in vivo as a general inhibitor of the onset of DNA replication.

The human MTS gene sequence was used to isolate corresponding genomic and cDNA clones from mice. Genes corresponding to MTS1, both the α and β forms, as well as to MTS2 were isolated from mice. The mouse and human genes are roughly 70–80% identical over portions of the coding regions. Analysis of the gene structures of the MTS genes in mice and humans indicates that the MTS1 and MTS2 genes likely arose from a single common ancestor by gene duplication and divergence. The time when the ancestral gene arose is unknown. MTS1-like sequences are found in mammals but maybe are not in Drosophila, Schizosaccharomyces, or Saccharomyces, as multiple species blots with DNA of these organisms revealed only weak hybridization to MTS1 probes. This finding must still be confirmed by analysis of the weakly hybridizing fragments. The data also suggest that there was a gene conversion event between MTS1 and MTS2 in humans which occurred between 19–33 million years ago. Mice and humans are estimated to have diverged 65 million years ago.

According to the diagnostic and prognostic method of the present invention, alteration of the wild-type MTS locus is detected. In addition, the method can be performed by detecting the wild-type MTS locus and confirming the lack of a predisposition or neoplasia. "Alteration of a wild-type gene" encompasses all forms of mutations including deletions, insertions and point mutations in the coding and noncoding regions. Deletions may be of the entire gene or only a portion of the gene. Point mutations may result in stop codons, frameshift mutations or amino acid substitutions. Somatic mutations are those which occur only in certain tissues, e.g., in the tumor tissue, and are not inherited in the germline. Germline mutations can be found in any of a body's tissues and are inherited. If only a single allele is somatically mutated, an early neoplastic state is indicated. However, if both alleles are mutated, then a late neoplastic state is indicated. The finding of MTS mutations thus provides both diagnostic and prognostic information. An MTS allele which is not deleted (e.g., that found on the sister chromosome to a chromosome carrying an MTS deletion) can be screened for other mutations, such as insertions, small deletions, and point mutations. It is believed that many mutations found in tumor tissues will be those leading to decreased expression of the MTS gene product. However, mutations leading to non-functional gene products would also lead to a cancerous state. Point mutational events may occur in regulatory regions, such as in the promoter of the gene, leading to loss or diminution of expression of the mRNA. Point mutations may also abolish proper RNA processing, leading to loss of expression of the MTS gene product, or a decrease in mRNA stability or translation efficiency.

Useful diagnostic techniques include, but are not limited to fluorescent in situ hybridization (FISH), direct DNA sequencing, PFGE analysis, Southern blot analysis, single stranded conformation analysis (SSCA), RNase protection assay, allele-specific oligonucleotide (ASO), dot blot analysis and PCR-SSCP, as discussed in detail further below.

Predisposition to cancers, such as melanoma and the other cancers identified herein, can be ascertained by testing any tissue of a human for mutations of the MTS gene. For example, a person who has inherited a germline MTS mutation would be prone to develop cancers. This can be determined by testing DNA from any tissue of the person's body. Most simply, blood can be drawn and DNA extracted from the cells of the blood. In addition, prenatal diagnosis can be accomplished by testing fetal cells, placental cells or amniotic fluid for mutations of the MTS gene. Alteration of a wild-type MTS allele, whether, for example, by point mutation or by deletion, can be detected by any of the means discussed herein.

In order to detect the alteration of the wild-type MTS gene in a tissue, it is helpful to isolate the tissue free from surrounding normal tissues. Means for enriching a tissue preparation for tumor cells are known in the art. For example, the tissue may be isolated from paraffin or cryostat sections. Cancer cells may also be separated from normal cells by flow cytometry. These techniques, as well as other techniques for separating tumor cells from normal cells, are well known in the art. If the tumor tissue is highly contaminated with normal cells, detection of mutations is more difficult.

A rapid preliminary analysis to detect polymorphisms in DNA sequences can be performed by looking at a series of Southern blots of DNA cut with one or more restriction enzymes, preferably a large number of restriction enzymes. Each blot contains a series of normal individuals and a series of cancer cases, tumors, or both. Southern blots displaying hybridizing fragments (differing in length from control DNA when probed with sequences near or including the MTS locus) indicate a possible mutation. If restriction enzymes which produce very large restriction fragments are used, then pulsed field gel electrophoresis ("PFGE") is employed.

Detection of point mutations may be accomplished by molecular cloning of the MTS allele(s) and sequencing that allele(s) using techniques well known in the art. Alternatively, the gene sequences can be amplified, using known techniques, directly from a genomic DNA preparation from the tumor tissue. The DNA sequence of the amplified sequences can then be determined.

There are six well known methods for a more complete, yet still indirect, test for confirming the presence of a susceptibility allele: 1) single stranded conformation analysis ("SSCA") (Orita et al., 1989); 2) denaturing gradient gel electrophoresis ("DGGE") (Wartell et al., 1990; Sheffield et al., 1989); 3) RNase protection assays (Finkelstein et al., 1990; Kinszler et al., 1991); 4) allele-specific oligonucleotides ("ASOs") (Conner et al., 1983); 5) the use of proteins which recognize nucleotide mismatches, such as the *E. coli* mutS protein (Modrich, 1991); and, 6) allele-specific PCR (Rano & Kidd, 1989). For allele-specific PCR, primers are used which hybridize at their 3' ends to a particular MTS mutation. If the particular MTS mutation is not present, an amplification product is not observed. Amplification Refractory Mutation System (ARMS) can also be used, as disclosed in European Patent Application Publication No. 0332435 and in Newton et al., 1989. Insertions and deletions of genes can also be detected by cloning, sequencing and amplification. In addition, restriction fragment length polymorphism (RFLP) probes for the gene or surrounding marker genes can be used to score alteration of an allele or an insertion in a polymorphic fragment. Such a method is particularly useful for screening relatives of an affected individual for the presence of the MTS mutation found in that individual. Other techniques for detecting insertions and deletions as known in the art can be used.

In the first three methods (i.e., SSCA, DGGE and RNase protection assay), a new electrophoretic band appears. SSCA detects a band which migrates differentially because the sequence change causes a difference in single-strand, intramolecular base pairing. RNase protection involves cleavage of the mutant polynucleotide into two or more smaller fragments. DGGE detects differences in migration rates of mutant sequences compared to wild-type sequences, using a denaturing gradient gel. In an allele-specific oligonucleotide assay, an oligonucleotide is designed which detects a specific sequence, and the assay is performed by detecting the presence or absence of a hybridization signal. In the mutS assay, the protein binds only to sequences that contain a nucleotide mismatch in a heteroduplex between mutant and wild-type sequences.

Mismatches, according to the present invention, are hybridized nucleic acid duplexes in which the two strands are not 100% complementary. Lack of total homology may be due to deletions, insertions, inversions or substitutions. Mismatch detection can be used to detect point mutations in the gene or its mRNA product. While these techniques are less sensitive than sequencing, they are simpler to perform on a large number of tumor samples. An example of a mismatch cleavage technique is the RNase protection method. In the practice of the present invention, the method involves the use of a labeled riboprobe which is complementary to the human wild-type MTS gene coding sequence. The riboprobe and either mRNA or DNA isolated from the tumor tissue are annealed (hybridized) together and subsequently digested with the enzyme RNase A which is able to detect some mismatches in a duplex RNA structure. If a mismatch is detected by RNase A, it cleaves at the site of the mismatch. Thus, when the annealed RNA preparation is separated on an electrophoretic gel matrix, if a mismatch has been detected and cleaved by RNase A, an RNA product will be seen which is smaller than the full length duplex RNA for the riboprobe and the mRNA or DNA. The riboprobe need not be the full length of the MTS mRNA or gene but can be a segment of either. If the riboprobe comprises only a segment of the MTS mRNA or gene, it will be desirable to use a number of these probes to screen the whole mRNA sequence for mismatches.

In similar fashion, DNA probes can be used to detect mismatches, through enzymatic or chemical cleavage. See, e.g., Cotton et al., 1988; Shenk et al., 1975; Novack et al., 1986. Alternatively, mismatches can be detected by shifts in the electrophoretic mobility of mismatched duplexes relative to matched duplexes. See, e.g., Cariello, 1988. With either riboprobes or DNA probes, the cellular mRNA or DNA which might contain a mutation can be amplified using PCR (see below) before hybridization. Changes in DNA of the MTS gene can also be detected using Southern hybridization, especially if the changes are gross rearrangements, such as deletions and insertions.

DNA sequences of the MTS gene which have been amplified by use of PCR may also be screened using allele-specific probes. These probes are nucleic acid oligomers, each of which contains a region of the MTS gene sequence harboring a known mutation. For example, one oligomer may be about 30 nucleotides in length, corresponding to a portion of the MTS gene sequence. By use of a battery of such allele-specific probes, PCR amplification products can be screened to identify the presence of a previously identified mutation in the MTS gene. Hybridization of allele-specific probes with amplified MTS sequences can be performed, for example, on a nylon filter. Hybridization to a particular probe under stringent hybridization conditions indicates the presence of the same mutation in the tumor tissue as in the allele-specific probe.

The most definitive test for mutations in a candidate locus is to directly compare genomic MTS sequences from cancer patients with those from a control population. Alternatively, one could sequence messenger RNA after amplification, e.g., by PCR, thereby eliminating the necessity of determining the exon structure of the candidate gene.

Mutations from cancer patients falling outside the coding region of MTS can be detected by examining the non-coding regions, such as introns and regulatory sequences near or within the MTS gene. An early indication that mutations in noncoding regions are important may come from Northern blot experiments that reveal messenger RNA molecules of abnormal size or abundance in cancer patients as compared to control individuals.

Alteration of MTS mRNA expression can be detected by any techniques known in the art. These include Northern blot analysis, PCR amplification and RNase protection. Diminished mRNA expression indicates an alteration of the wild-type MTS gene. Alteration of wild-type MTS genes can also be detected by screening for alteration of wild-type MTS protein. For example, monoclonal antibodies immunoreactive with MTS can be used to screen a tissue. Lack of cognate antigen would indicate an MTS mutation. Antibodies specific for products of mutant alleles could also be used to detect mutant MTS gene product. Such immunological assays can be done in any convenient formats known in the art. These include Western blots, immunohistochemical assays and ELISA assays. Any means for detecting an altered MTS protein can be used to detect alteration of wild-type MTS genes. Functional assays, such as protein binding determinations, can be used. For example, it is known that MTS protein binds to Cdks, especially Cdk4. Thus, an assay for the ability to bind to wild-type MTS protein or Cdk4 can be employed. In addition, assays can be used which detect MTS biochemical function, the inhibition of Cdks, such as Cdk4, and regulation of the cell cycle. Finding a mutant MTS gene product indicates alteration of a wild-type MTS gene.

Mutant MTS genes or gene products can also be detected in other human body samples, such as serum, stool, urine and sputum. The same techniques discussed above for detection of mutant MTS genes or gene products in tissues can be applied to other body samples. Cancer cells are sloughed off from tumors and appear in such body samples. In addition, the MTS gene product itself may be secreted into the extracellular space and found in these body samples even in the absence of cancer cells. By screening such body samples, a simple early diagnosis can be achieved for many types of cancers. In addition, the progress of chemotherapy or radiotherapy can be monitored more easily by testing such body samples for mutant MTS genes or gene products.

The methods of diagnosis of the present invention are applicable to any tumor in which MTS has a role in tumorigenesis. Deletions of chromosome arm 9p or somatic mutations within the MTS region have been observed in almost all tumors examined. The diagnostic method of the present invention is useful for clinicians, so they can decide upon an appropriate course of treatment.

The primer pairs of the present invention are useful for determination of the nucleotide sequence of a particular MTS allele using the PCR. The pairs of single-stranded DNA primers can be annealed to sequences within or surrounding the MTS gene on chromosome 9p in order to prime amplifying DNA synthesis of the MTS gene itself. A complete set of these primers allows synthesis of all of the nucleotides of the MTS gene coding sequences, i.e., the exons. The set of primers preferably allows synthesis of both intron and exon sequences. Allele-specific primers can also be used. Such primers anneal only to particular MTS mutant alleles, and thus will only amplify a product in the presence of the mutant allele as a template.

In order to facilitate subsequent cloning of amplified sequences, primers may have restriction enzyme site sequences appended to their 5' ends. Thus, all nucleotides of the primers are derived from MTS sequences or sequences adjacent to MTS, except for the few nucleotides necessary to form a restriction enzyme site. Such enzymes and sites are well known in the art. The primers themselves can be synthesized using techniques which are well known in the art. Generally, the primers can be made using oligonucleotide synthesizing machines which are commercially available. Given the sequence of the MTS open reading frames shown in SEQ ID NO:1, SEQ ID NO:3, SEQ ID NO:4, SEQ ID NO:5, SEQ ID NO:13, SEQ ID NO:15, SEQ ID NO:25, SEQ ID NO:36, SEQ ID NO:44 and SEQ ID NO:45, design of particular primers is well within the skill of the art.

The nucleic acid probes provided by the present invention are useful for a number of purposes. They can be used in Southern hybridization to genomic DNA and in the RNase protection method for detecting point mutations already discussed above. The probes can be used to detect PCR amplification products. They may also be used to detect mismatches with the MTS gene or mRNA using other techniques.

Definitions

The present invention employs the following definitions:

"Amplification of Polynucleotides" utilizes methods such as the polymerase chain reaction (PCR), ligation amplification (or ligase chain reaction, LCR) and amplification methods based on the use of Q-beta replicase. These methods are well known and widely practiced in the art. See, e.g., U.S. Pat. Nos. 4,683,195 and 4,683,202 and Innis et al., 1990 (for PCR); and Wu et al., 1989a (for LCR). Reagents and hardware for conducting PCR are commercially available. Primers useful to amplify sequences from the MTS region are preferably complementary to, and hybridize specifically to sequences in the MTS region or in regions that flank a target region therein. MTS sequences generated by amplification may be sequenced directly. Alternatively, but less desirably, the amplified sequence(s) may be cloned prior to sequence analysis. A method for the direct cloning and sequence analysis of enzymatically amplified genomic segments has been described by Scharf, 1986.

"Analyte polynucleotide" and "analyte strand" refer to a single- or double-stranded polynucleotide which is suspected of containing a target sequence, and which may be present in a variety of types of samples, including biological samples.

"Antibodies." The present invention also provides polyclonal and/or monoclonal antibodies and fragments thereof, and immunologic binding equivalents thereof, which are capable of specifically binding to the MTS polypeptides and fragments thereof or to polynucleotide sequences from the MTS region, particularly from the MTS locus or a portion thereof. The term "antibody" is used both to refer to a homogeneous molecular entity, or a mixture such as a serum product made up of a plurality of different molecular entities. Polypeptides may be prepared synthetically in a peptide synthesizer and coupled to a carrier molecule (e.g., keyhole limpet hemocyanin) and injected over several months into rabbits. Rabbit sera is tested for immunoreactivity to the MTS polypeptide or fragment. Monoclonal antibodies may be made by injecting mice with the protein polypeptides, fusion proteins or fragments thereof. Monoclonal antibodies will be screened by ELISA and tested for specific immunoreactivity with MTS polypeptide or fragments thereof. See, Harlow & Lane, 1988. These antibodies will be useful in assays as well as pharmaceuticals.

Once a sufficient quantity of desired polypeptide has been obtained, it may be used for various purposes. A typical use is the production of antibodies specific for binding. These antibodies may be either polyclonal or monoclonal, and may be produced by in vitro or in vivo techniques well known in the art.

For production of polyclonal antibodies, an appropriate target immune system, typically mouse or rabbit, is selected. Substantially purified antigen is presented to the immune system in a fashion determined by methods appropriate for the animal and by other parameters well known to immunologists. Typical sites for injection are in footpads, intramuscularly, intraperitoneally, or intradermally. Of course, other species may be substituted for mouse or rabbit. Polyclonal antibodies are then purified using techniques known in the art, adjusted for the desired specificity.

An immunological response is usually assayed with an immunoassay. Normally, such immunoassays involve some purification of a source of antigen, for example, that produced by the same cells and in the same fashion as the antigen. A variety of immunoassay methods are well known in the art. See, e.g., Harlow & Lane, 1988, or Goding, 1986.

Monoclonal antibodies with affinities of $10^{-8}$ $M^{-1}$ or preferably $10^{-9}$ to $10^{-10}$ $M^{-1}$ or stronger will typically be made by standard procedures as described, e.g., in Harlow & Lane, 1988 or Goding, 1986. Briefly, appropriate animals will be selected and the desired immunization protocol followed. After the appropriate period of time, the spleens of such animals are excised and individual spleen cells fused, typically, to immortalized myeloma cells under appropriate selection conditions. Thereafter, the cells are clonally separated and the supernatants of each clone tested for their production of an appropriate antibody specific for the desired region of the antigen.

Other suitable techniques involve in vitro exposure of lymphocytes to the antigenic polypeptides, or alternatively, to selection of libraries of antibodies in phage or similar vectors. See Huse et al., 1989. The polypeptides and antibodies of the present invention may be used with or without modification. Frequently, polypeptides and antibodies will be labeled by joining, either covalently or non-covalently, a substance which provides for a detectable signal. A wide variety of labels and conjugation techniques are known and are reported extensively in both the scientific and patent literature. Suitable labels include radionuclides, enzymes, substrates, cofactors, inhibitors, fluorescent agents, chemiluminescent agents, magnetic particles and the like. Patents teaching the use of such labels include U.S. Pat. Nos. 3,817,837; 3,850,752; 3,939,350; 3,996,345; 4,277,437; 4,275,149; and 4,366,241. Also, recombinant immunoglobulins may be produced (see U.S. Pat. No. 4,816,567).

"Binding partner" refers to a molecule capable of binding a ligand molecule with high specificity, as for example, an antigen and an antigen-specific antibody or an enzyme and its inhibitor. In general, the specific binding partners must bind with sufficient affinity to immobilize the analyte copy/complementary strand duplex (in the case of polynucleotide hybridization) under the isolation conditions. Specific binding partners are known in the art and include, for example, biotin and avidin or streptavidin, IgG and protein A, the numerous, known receptor-ligand couples, and complementary polynucleotide strands. In the case of complementary polynucleotide binding partners, the partners are normally at least about 15 bases in length, and may be at least 40 bases in length. The polynucleotides may be composed of DNA, RNA, or synthetic nucleotide analogs.

A "biological sample" refers to a sample of tissue or fluid suspected of containing an analyte polynucleotide or polypeptide from an individual including, but not limited to, e.g., plasma, serum, spinal fluid, lymph fluid, the external sections of the skin, respiratory, intestinal, and genitourinary tracts, tears, saliva, blood cells, tumors, organs, tissue and samples of in vitro cell culture constituents.

As used herein, the terms "diagnosing" or "prognosing," as used in the context of neoplasia, are used to indicate 1) the classification of lesions as neoplasia, 2) the determination of the severity of the neoplasia, or 3) the monitoring of the disease progression, prior to, during and after treatment.

"Encode". A polynucleotide is said to "encode" a polypeptide if, in its native state or when manipulated by methods well known to those skilled in the art, it can be transcribed and/or translated to produce the mRNA for and/or the polypeptide or a fragment thereof. The anti-sense strand is the complement of such a nucleic acid, and the encoding sequence can be deduced therefrom.

"Isolated" or "substantially pure". An "isolated" or "substantially pure" nucleic acid (e.g., an RNA, DNA or a mixed polymer) is one which is substantially separated from other cellular components which naturally accompany a native human sequence or protein, e.g., ribosomes, polymerases, many other human genome sequences and proteins. The term embraces a nucleic acid sequence or protein which has been removed from its naturally occurring environment, and includes recombinant or cloned DNA isolates and chemically synthesized analogs or analogs biologically synthesized by heterologous systems.

"MTS Allele" refers to normal alleles of the MTS locus as well as alleles carrying variations that predispose individuals to develop cancer of many sites including, for example, melanoma, ocular melanoma, leukemia, astrocytoma, glioblastoma, lymphoma, glioma, Hodgkin's lymphoma, multiple myeloma, sarcoma, myosarcoma, cholangiocarcinoma, squamous cell carcinoma, CLL, and cancers of the pancreas, breast, brain, prostate, bladder, thyroid, ovary, uterus, testis, kidney, stomach, colon and rectum. Such predisposing alleles are also called "MTS susceptibility alleles".

"MTS Locus," "MTS gene," "MTS Nucleic Acids" or "MTS Polynucleotide" refer to polynucleotides, all of which are in the MTS region, that are likely to be expressed in normal tissue, certain alleles of which predispose an individual to develop melanoma and other cancers, such as ocular melanoma, leukemia, astrocytoma, glioblastoma, lymphoma, glioma, Hodgkin's lymphoma, multiple myeloma, sarcoma, myosarcoma, cholangiocarcinoma, squamous cell carcinoma, CLL, and cancers of the pancreas, breast, brain, prostate, bladder, thyroid, ovary, uterus, testis, kidney, stomach, colon and rectum. The MTS locus is used interchangeably herein with the prior art designation MLM locus, and the use of "MTS" is intended to include "MLM" as used with reference to locus, gene, region, and the like. Mutations at the MTS locus may be involved in the initiation and/or progression of other types of tumors. The locus is indicated in part by mutations that predispose individuals to develop cancer. These mutations fall within the MTS region described infra. The MTS locus is intended to include coding sequences, intervening sequences and regulatory elements controlling transcription and/or translation. The MTS locus is intended to include all allelic variations of the DNA sequence.

These terms, when applied to a nucleic acid, refer to a nucleic acid which encodes a MTS polypeptide (including p16), fragment, homolog or variant, including, e.g., protein fusions or deletions. The nucleic acids of the present invention will possess a sequence which is either derived from, or substantially similar to a natural MTS-encoding gene or one having substantial homology with a natural MTS-encoding gene or a portion thereof. The coding sequence for a human MTS polypeptide (MTS1) is shown in SEQ ID NO:1, and the amino acid sequence of a human MTS polypeptide (MTS1) is shown in SEQ ID NO:2. The coding sequence for a second human MTS polypeptide (MTS1E1β) is shown in SEQ ID NO:13, and the corresponding amino acid sequence is shown in SEQ ID NO:14. The coding sequence for a third human MTS polypeptide (MTS2) is shown in SEQ ID NO:15, and the corresponding amino acid sequence is shown in SEQ ID NO:16. The mouse MTS1E1β cDNA is shown as SEQ ID NO:25, mouse MTS1 cDNA is shown as SEQ ID NO:44 with the corresponding polypeptide shown as SEQ ID NO:46, and mouse MTS2 cDNA is shown as SEQ ID NO:45 with the corresponding polypeptide shown as SEQ ID NO:47. The term P16 is used interchangeably with MTS1 and MTS1E1β and is used to mean both MTS1 which encodes a p16 and MTS1E1β which encodes a p10. MTS1 and MTS1E1β are two forms of one gene, the two forms being dependent upon which of two promoters is used for transcription. MTS2 is a separate portion of the MTS region and it encodes a p15.

The polynucleotide compositions of this invention include RNA, cDNA, genomic DNA, synthetic forms, and mixed polymers, both sense and antisense strands, and may be chemically or biochemically modified or may contain non-natural or derivatized nucleotide bases, as will be readily appreciated by those skilled in the art. Such modifications include, for example, labels, methylation, substitution of one or more of the naturally occurring nucleotides with an analog, internucleotide modifications such as uncharged linkages (e.g., methyl phosphonates, phosphotriesters, phosphoamidates, carbamates, etc.), charged linkages (e.g., phosphorothioates, phosphorodithioates, etc.), pendent moieties (e.g., polypeptides), intercalators (e.g., acridine, psoralen, etc.), chelators, alkylators, and modified linkages (e.g., alpha anomeric nucleic acids, etc.). Also included are synthetic molecules that mimic polynucleotides in their ability to bind to a designated sequence via hydrogen bonding and other chemical interactions. Such molecules are known in the art and include, for example, those in which peptide linkages substitute for phosphate linkages in the backbone of the molecule.

The present invention provides recombinant nucleic acids comprising all or part of the MTS region. The recombinant construct may be capable of replicating autonomously in a host cell. Alternatively, the recombinant construct may become integrated into the chromosomal DNA of the host cell. Such a recombinant polynucleotide comprises a polynucleotide of genomic, cDNA, semi-synthetic, or synthetic origin which, by virtue of its origin or manipulation, 1) is not associated with all or a portion of a polynucleotide with which it is associated in nature; 2) is linked to a polynucleotide other than that to which it is linked in nature; or 3) does not occur in nature.

Therefore, recombinant nucleic acids comprising sequences otherwise not naturally occurring are provided by this invention. Although the wild-type sequence may be employed, it will often be altered, e.g., by deletion, substitution or insertion.

cDNA or genomic libraries of various types may be screened as natural sources of the nucleic acids of the present invention, or such nucleic acids may be provided by amplification of sequences resident in genomic DNA or other natural sources, e.g., by PCR. The choice of cDNA libraries normally corresponds to a tissue source which is abundant in mRNA for the desired proteins. Phage libraries are normally preferred, but other types of libraries may be used. Clones of a library are spread onto plates, transferred to a substrate for screening, denatured and probed for the presence of desired sequences.

The DNA sequences used in this invention will usually comprise at least about five codons (15 nucleotides), more usually at least about 7–15 codons, and most preferably, at least about 35 codons. One or more introns may also be present. This number of nucleotides is usually about the minimal length required for a successful probe that would hybridize specifically with a MTS-encoding sequence.

Techniques for nucleic acid manipulation are described generally, for example, in Sambrook et al., 1989 or Ausubel et al., 1992. Reagents useful in applying such techniques, such as restriction enzymes and the like, are widely known in the art and commercially available from such vendors as New England BioLabs, Boehringer Mannheim, Amersham, Promega Biotec, U.S. Biochemicals, New England Nuclear, and a number of other sources. The recombinant nucleic acid sequences used to produce fusion proteins of the present invention may be derived from natural or synthetic sequences. Many natural gene sequences are obtainable from various cDNA or from genomic libraries using appropriate probes. See, GenBank, National Institutes of Health.

"MTS Region" refers to a portion of human chromosome 9 found in the P1 clones P1-1062 and P1-1063. These P1 clones, in *E. coli* NS3529, were deposited with the American Type Culture Collection, Rockville, Md. USA on Mar. 16, 1994 and assigned ATCC Nos. 69589 and 69590, respectively. This region contains the MTS locus, including the MTS1, MTS2 and MTS1E1β genes. In mice, the MTS genes are located on chromosome 4 within an 80 kilobase region.

As used herein, the terms "MTS locus," "MTS allele" and "MTS region" all refer to the double-stranded DNA comprising the locus, allele, or region, as well as either of the single-stranded DNAs comprising the locus, allele or region.

As used herein, a "portion" of the MTS locus or region or allele is defined as having a minimal size of at least about eight nucleotides, or preferably about 15 nucleotides, or more preferably at least about 25 nucleotides, and may have a minimal size of at least about 40 nucleotides.

"MTS protein" or "MTS polypeptide" refer to a protein or polypeptide encoded by the MTS locus (including MTS1 polypeptide, MTS2 polypeptide and MTS1E1β polypeptide), variants or fragments thereof The term "polypeptide" refers to a polymer of amino acids and its equivalent and does not refer to a specific length of the product; thus, peptides, oligopeptides and proteins are included within the definition of a polypeptide. This term also does not refer to, or exclude modifications of the polypeptide, for example, glycosylations, acetylations, phosphorylations, and the like. Included within the definition are, for example, polypeptides containing one or more analogs of an amino acid (including, for example, unnatural amino acids, etc.), polypeptides with substituted linkages as well as other modifications known in the art, both naturally and non-naturally occurring. Ordinarily, such polypeptides will be at least about 50% homologous to the native MTS sequence, preferably in excess of about 90%, and more preferably at least about 95% homologous. Also included are proteins encoded by DNA which hybridize under high or low stringency conditions, to MTS-encoding nucleic acids and closely related polypeptides or proteins retrieved by antisera to the MTS protein(s).

The length of polypeptide sequences compared for homology will generally be at least about 16 amino acids, usually at least about 20 residues, more usually at least about 24 residues, typically at least about 28 residues, and preferably more than about 35 residues.

"Operably linked" refers to a juxtaposition wherein the components so described are in a relationship permitting them to function in their intended manner. For instance, a promoter is operably linked to a coding sequence if the promoter affects its transcription or expression.

"Probes". Polynucleotide polymorphisms associated with MTS alleles which predispose to certain cancers or are associated with most cancers are detected by hybridization with a polynucleotide probe which forms a stable hybrid with that of the target sequence, under stringent to moderately stringent hybridization and wash conditions. If it is expected that the probes will be perfectly complementary to the target sequence, stringent conditions will be used. Hybridization stringency may be lessened if some mismatching is expected, for example, if variants are expected with the result that the probe will not be completely complementary. Conditions are chosen which rule out nonspecific/ adventitious bindings, that is, which minimize noise. Since such indications identify neutral DNA polymorphisms as well as mutations, these indications need further analysis to demonstrate detection of a MTS susceptibility allele.

Probes for MTS alleles may be derived from the sequences of the MTS region or its cDNAs. The probes may be of any suitable length, which span all or a portion of the MTS region, and which allow specific hybridization to the MTS region. If the target sequence contains a sequence identical to that of the probe, the probes may be short, e.g., in the range of about 8–30 base pairs, since the hybrid will be relatively stable under even stringent conditions. If some degree of mismatch is expected with the probe, i.e., if it is suspected that the probe will hybridize to a variant region, a longer probe may be employed which hybridizes to the target sequence with the requisite specificity.

The probes will include an isolated polynucleotide attached to a label or reporter molecule and may be used to isolate other polynucleotide sequences, having sequence similarity by standard methods. For techniques for preparing and labeling probes see, e.g., Sambrook et al., 1989 or Ausubel et al., 1992. Other similar polynucleotides may be selected by using homologous polynucleotides. Alternatively, polynucleotides encoding these or similar polypeptides may be synthesized or selected by use of the redundancy in the genetic code. Various codon substitutions may be introduced, e.g., by silent changes (thereby producing various restriction sites) or to optimize expression for a particular system. Mutations may be introduced to modify the properties of the polypeptide, perhaps to change ligand-binding affinities, interchain affinities, or the polypeptide degradation or turnover rate.

Probes comprising synthetic oligonucleotides or other polynucleotides of the present invention may be derived from naturally occurring or recombinant single- or double-stranded polynucleotides, or be chemically synthesized. Probes may also be labeled by nick translation, Klenow fill-in reaction, or other methods known in the art.

Portions of the polynucleotide sequence having at least about eight nucleotides, usually at least about 15 nucleotides, and fewer than about 6 Kb, usually fewer than about 1.0 Kb, from a polynucleotide sequence encoding MTS are preferred as probes. The probes may also be used to determine whether mRNA encoding MTS is present in a cell or tissue.

"Protein modifications or fragments" are provided by the present invention for MTS polypeptides or fragments thereof which are substantially homologous to primary structural sequence but which include, e.g., in vivo or in vitro chemical and biochemical modifications or which incorporate unusual amino acids. Such modifications include, for example, acetylation, carboxylation, phosphorylation, glycosylation, ubiquitination, labeling, e.g., with radionuclides, and various enzymatic modifications, as will be readily appreciated by those well skilled in the art. A variety of methods for labeling polypeptides and of substituents or labels useful for such purposes are well known in the art, and include radioactive isotopes such as $^{32}P$, ligands, which bind to labeled antiligands (e.g., antibodies), fluorophores, chemiluminescent agents, enzymes, and antiligands which can serve as specific binding pair members for a labeled ligand. The choice of label depends on the sensitivity required, ease of conjugation with the primer, stability requirements, and available instrumentation. Methods of labeling polypeptides are well known in the art. See, e.g., Sambrook et al., 1989 or Ausubel et al., 1992.

Besides substantially full-length polypeptides, the present invention provides for biologically active fragments of the polypeptides. Significant biological activities include ligand-binding, immunological activity and other biological activities characteristic of MTS polypeptides. Immunological activities include both immunogenic function in a target immune system, as well as sharing of immunological epitopes for binding, serving as either a competitor or substitute antigen for an epitope of the MTS protein. As used herein, "epitope" refers to an antigenic determinant of a polypeptide. An epitope could comprise three amino acids in a spatial conformation which is unique to the epitope. Generally, an epitope consists of at least five such amino acids, and more usually consists of at least 8–10 such amino acids. Methods of determining the spatial conformation of such amino acids are known in the art.

For immunological purposes, tandem-repeat polypeptide segments may be used as immunogens, thereby producing highly antigenic proteins. Alternatively, such polypeptides will serve as highly efficient competitors for specific binding. Production of antibodies specific for MTS polypeptides or fragments thereof is described below.

The present invention also provides for fusion polypeptides, comprising MTS polypeptides and fragments. Homologous polypeptides may be fusions between two or more MTS polypeptide sequences or between the sequences of MTS and a related protein. Likewise, heterologous fusions may be constructed which would exhibit a combination of properties or activities of the derivative proteins For example, ligand-binding or other domains may be "swapped" between different new fusion polypeptides or fragments. Such homologous or heterologous fusion polypeptides may display, for example, altered strength or specificity of binding. Fusion partners include immunoglobulins, bacterial β-galactosidase, trpE, protein A, β-lactamase, alpha amylase, alcohol dehydrogenase and yeast alpha mating factor. See, e.g., Godowski et al., 1988.

Fusion proteins will typically be made by either recombinant nucleic acid methods, as described below, or may be chemically synthesized. Techniques for the synthesis of polypeptides are described, for example, in Merrifield, 1963.

"Protein purification" refers to various methods for the isolation of the MTS polypeptides from other biological material, such as from cells transformed with recombinant nucleic acids encoding MTS, and are well known in the art. For example, such polypeptides may be purified by immunoaffinity chromatography employing, e.g., the antibodies provided by the present invention. Various methods of protein purification are well known in the art, and include those described in Deutscher, 1990 and Scopes, 1982.

The terms "isolated", "substantially pure", and "substantially homogeneous" are used interchangeably to describe a protein or polypeptide which has been separated from components which accompany it in its natural state. A monomeric protein is substantially pure when at least about 60 to 75% of a sample exhibits a single polypeptide sequence. A substantially pure protein will typically comprise about 60 to 90% W/W of a protein sample, more usually about 95%, and preferably will be over about 99% pure. Protein purity or homogeneity may be indicated by a number of means well known in the art, such as polyacrylamide gel electrophoresis or a protein sample, followed by visualizing a single polypeptide band upon staining the gel. For certain purposes, higher resolution may be provided by using HPLC or other means well known in the art for purification utilized.

A MTS protein is substantially free of naturally associated components when it is separated from the native contaminants which accompany it in its natural state. Thus, a polypeptide which is chemically synthesized or synthesized in a cellular system different from the cell from which it naturally originates will be substantially free from its naturally associated components. A protein may also be rendered substantially free of naturally associated components by isolation, using protein purification techniques well known in the art.

A polypeptide produced as an expression product of an isolated and manipulated genetic sequence is an "isolated polypeptide," as used herein, even if expressed in a homologous cell type. Synthetically made forms or molecules expressed by heterologous cells are inherently isolated molecules.

"Recombinant nucleic acid" is a nucleic acid which is not naturally occurring, or which is made by the artificial combination of two otherwise separated segments of sequence. This artificial combination is often accomplished by either chemical synthesis means, or by the artificial manipulation of isolated segments of nucleic acids, e.g., by genetic engineering techniques. Such is usually done to replace a codon with a redundant codon encoding the same or a conservative amino acid, while typically introducing or removing a sequence recognition site. Alternatively, it is performed to join together nucleic acid segments of desired functions to generate a desired combination of functions.

"Regulatory sequences" refers to those sequences normally within 10 Kb of the coding region of a locus which affect the expression of the gene (including transcription of the gene, and translation, splicing, stability or the like of the messenger RNA).

"Substantial homology or similarity". A nucleic acid or fragment thereof is "substantially homologous" ("or substantially similar") to another if, when optimally aligned (with appropriate nucleotide insertions or deletions) with the other nucleic acid (or its complementary strand), there is nucleotide sequence identity in at least about 60% of the nucleotide bases, usually at least about 70%, more usually at least about 80%, preferably at least about 90%, and more preferably at least about 95–98% of the nucleotide bases.

Alternatively, substantial homology or (similarity) exists when a nucleic acid or fragment thereof will hybridize to another nucleic acid (or a complementary strand thereof) under selective hybridization conditions, to a strand, or to its complement. Selectivity of hybridization exists when hybridization which is substantially more selective than total lack of specificity occurs. Typically, selective hybridization will occur when there is at least about 55% homology over a stretch of at least about 14 nucleotides, preferably at least about 65%, more preferably at least about 75%, and most preferably at least about 90%. See, Kanehisa, 1984. The length of homology comparison, as described, may be over longer stretches, and in certain embodiments will often be over a stretch of at least about nine nucleotides, usually at least about 20 nucleotides, more usually at least about 24 nucleotides, typically at least about 28 nucleotides, more typically at least about 32 nucleotides, and preferably at least about 36 or more nucleotides.

Nucleic acid hybridization will be affected by such conditions as salt concentration, temperature, or organic solvents, in addition to the base composition, length of the complementary strands, and the number of nucleotide base mismatches between the hybridizing nucleic acids, as will be readily appreciated by those skilled in the art. Stringent temperature conditions will generally include temperatures in excess of 30° C., typically in excess of 37° C., and preferably in excess of 45° C. Stringent salt conditions will ordinarily be less than 1000 mM, typically less than 500 mM, and preferably less than 200 mM. However, the combination of parameters is much more important than the measure of any single parameter. See, e.g., Wetmur & Davidson, 1968.

Probe sequences may also hybridize specifically to duplex DNA under certain conditions to form triplex or other higher order DNA complexes. The preparation of such probes and suitable hybridization conditions are well known in the art.

The terms "substantial homology" or "substantial identity", when referring to polypeptides, indicate that the polypeptide or protein in question exhibits at least about 30% identity with an entire naturally-occurring protein or a portion thereof, usually at least about 70% identity, and preferably at least about 95% identity.

"Substantially similar function" refers to the function of a modified nucleic acid or a modified protein, with reference to the wild-type MTS nucleic acid or wild-type MTS polypeptide. The modified polypeptide will be substantially homologous to the wild-type MTS polypeptide and will have substantially the same function, i.e., the inhibition of Cdks, especially Cdk4. The modified polypeptide may have an altered amino acid sequence and/or may contain modified amino acids. In addition to the function of inhibiting Cdks, the modified polypeptide may have other useful properties, such as a longer half-life. The Cdk-inhibitory activity of the modified polypeptide may be substantially the same as the activity of the wild-type MTS polypeptide. Alternatively, the Cdk-inhibitory activity of the modified polypeptide may be higher than the activity of the wild-type MTS polypeptide. The modified polypeptide is synthesized using conventional techniques, or is encoded by a modified nucleic acid and produced using conventional techniques. The modified nucleic acid is prepared by conventional techniques. A nucleic acid with a function substantially similar to the wild-type MTS gene function produces the modified protein described above.

Homology, for polypeptides, is typically measured using sequence analysis software. See, e.g., the Sequence Analysis Software Package of the Genetics Computer Group, University of Wisconsin Biotechnology Center, 910 University Avenue, Madison, Wis. 53705. Protein analysis software matches similar sequences using measure of homology assigned to various substitutions, deletions, substitutions, and other modifications. Conservative substitutions typically include substitutions within the following groups: glycine, alanine; valine, isoleucine, leucine; aspartic acid, glutamic acid; asparagine, glutamine; serine, threonine; lysine, arginine; and phenylalanine, tyrosine.

A polypeptide "fragment," "portion" or "segment" is a stretch of amino acid residues of at least about five to seven contiguous amino acids, often at least about seven to nine contiguous amino acids, typically at least about nine to 13 contiguous amino acids and, most preferably, at least about 20 to 30 or more contiguous amino acids.

The polypeptides of the present invention, if soluble, may be coupled to a solid-phase support, e.g., nitrocellulose, nylon, column packing materials (e.g., Sepharose beads), magnetic beads, glass wool, plastic, metal, polymer gels, cells, or other substrates. Such supports may take the form, for example, of beads, wells, dipsticks, or membranes.

"Target region" refers to a region of the nucleic acid which is amplified and/or detected. The term "target sequence" refers to a sequence with which a probe or primer will form a stable hybrid under desired conditions.

The practice of the present invention employs, unless otherwise indicated, conventional techniques of chemistry, molecular biology, microbiology, recombinant DNA, genetics, and immunology. See, e.g., Maniatis et al., 1982; Sambrook et al., 1989; Ausubel et al., 1992; Glover, 1985; Anand, 1992; Guthrie & Fink, 1991. A general discussion of techniques and materials for human gene mapping, including mapping of human chromosome 9p, is provided, e.g., in White & Lalouel, 1988.

Preparation of recombinant or chemically synthesized nucleic acids; vectors, transformation, host cells Large amounts of the polynucleotides of the present invention may be produced by replication in a suitable host cell. Natural or synthetic polynucleotide fragments coding for a desired fragment will be incorporated into recombinant polynucleotide constructs, usually DNA constructs, capable of introduction into and replication in a prokaryotic or eukaryotic cell. Usually the polynucleotide constructs will be suitable for replication in a unicellular host, such as yeast or bacteria, but may also be intended for introduction to (with and without integration within the genome) cultured mammalian or plant or other eukaryotic cell lines. The purification of nucleic acids produced by the methods of the present invention are described, e.g., in Sambrook et al., 1989 or Ausubel et al., 1992.

The polynucleotides of the present invention may also be produced by chemical synthesis, e.g., by the phosphoramidite method described by Beaucage & Carruthers, 1981 or the triester method according to Matteucci et al., 1981, and may be performed on commercial, automated oligonucleotide synthesizers. A double-stranded fragment may be obtained from the single-stranded product of chemical synthesis either by synthesizing the complementary strand and annealing the strands together under appropriate conditions or by adding the complementary strand using DNA polymerase with an appropriate primer sequence.

Polynucleotide constructs prepared for introduction into a prokaryotic or eukaryotic host may comprise a replication system recognized by the host, including the intended polynucleotide fragment encoding the desired polypeptide, and will preferably also include transcription and translational initiation regulatory sequences operably linked to the polypeptide encoding segment. Expression vectors may include, for example, an origin of replication or autonomously replicating sequence (ARS) and expression control sequences, a promoter, an enhancer and necessary processing information sites, such as ribosome-binding sites, RNA splice sites, polyadenylation sites, transcriptional terminator sequences, and mRNA stabilizing sequences. Secretion signals may also be included where appropriate, whether from a native MTS protein or from other receptors or from secreted polypeptides of the same or related species, which allow the protein to cross and/or lodge in cell membranes, and thus attain its functional topology, or be secreted from the cell. Such vectors may be prepared by means of standard recombinant techniques well known in the art and discussed, for example, in Sambrook et al., 1989 or Ausubel et al. 1992.

The selection of an appropriate promoter and other necessary vector sequences will be selected so as to be functional in the host, and may include, when appropriate, those naturally associated with MTS genes. Examples of workable combinations of cell lines and expression vectors are described in Sambrook et al., 1989 or Ausubel et al., 1992; see also, e.g., Metzger et al., 1988. Many useful vectors are known in the art and may be obtained from such vendors as Stratagene, New England Biolabs, Promega Biotech, and others. Promoters such as the trp, lac and phage promoters, tRNA promoters and glycolytic enzyme promoters may be used in prokaryotic hosts. Useful yeast promoters include promoter regions for metallothionein, 3-phosphoglycerate kinase or other glycolytic enzymes such as enolase or glyceraldehyde-3-phosphate dehydrogenase, enzymes responsible for maltose and galactose utilization, and others. Vectors and promoters suitable for use in yeast expression are further described in Hitzeman et al., EP 73,675A. Appropriate non-native mammalian promoters might include the early and late promoters from SV40 (Fiers et al., 1978) or promoters derived from murine molony leukemia virus, mouse tumor virus, avian sarcoma viruses, adenovirus II, bovine papilloma virus or polyoma. In addition, the construct may be joined to an amplifiable gene (e.g., DHFR) so that multiple copies of the gene may be made. For appropriate enhancer and other expression control sequences, see also *Enhancers and Eukaryotic Gene Expression,* Cold Spring Harbor Press, Cold Spring Harbor, N.Y. (1983).

While such expression vectors may replicate autonomously, they may also replicate by being inserted into the genome of the host cell, by methods well known in the art.

Expression and cloning vectors will likely contain a selectable marker, a gene encoding a protein necessary for survival or growth of a host cell transformed with the vector. The presence of this gene ensures growth of only those host cells which express the inserts. Typical selection genes encode proteins that a) confer resistance to antibiotics or other toxic substances, e.g. ampicillin, neomycin, methotrexate, etc., b) complement auxotrophic deficiencies, or c) supply critical nutrients not available from complex media, e.g., the gene encoding D-alanine racemase for Bacilli. The choice of the proper selectable marker will depend on the host cell, and appropriate markers for different hosts are well known in the art.

The vectors containing the nucleic acids of interest can be transcribed in vitro, and the resulting RNA introduced into the host cell by well-known methods, e.g., by injection (see, T. Kubo et al., 1988), or the vectors can be introduced directly into host cells by methods well known in the art, which vary depending on the type of cellular host, including electroporation; transfection employing calcium chloride, rubidium chloride, calcium phosphate, DEAE-dextran, or other substances; microprojectile bombardment; lipofection; infection (where the vector is an infectious agent, such as a retroviral genome); and other methods. See generally, Sambrook et al., 1989 and Ausubel et al., 1992. The introduction of the polynucleotides into the host cell by any method known in the art, including, inter alia, those described above, will be referred to herein as "transformation." The cells into which have been introduced nucleic acids described above are meant to also include the progeny of such cells.

Large quantities of the nucleic acids and polypeptides of the present invention may be prepared by expressing the MTS nucleic acids or portions thereof in vectors or other expression vehicles in compatible prokaryotic or eukaryotic host cells. The most commonly used prokaryotic hosts are strains of *Escherichia coli,* although other prokaryotes, such as *Bacillus subtilis* or Pseudomonas may also be used.

Mammalian or other eukaryotic host cells, such as those of yeast, filamentous fungi, plant, insect, or amphibian or avian species, may also be useful for production of the proteins of the present invention. Propagation of mammalian cells in culture is per se well known. See, Jakoby and Pastan (eds.), 1979. Examples of commonly used mammalian host cell lines are VERO and HeLa cells, Chinese hamster ovary (CHO) cells, and WI38, BHK, and COS cell lines, although it will be appreciated by the skilled practitioner that other cell lines may be appropriate, e.g., to provide higher expression, desirable glycosylation patterns, or other features.

Clones are selected by using markers depending on the mode of the vector construction. The marker may be on the same or a different DNA molecule, preferably the same DNA molecule. In prokaryotic hosts, the transformant may be selected, e.g., by resistance to ampicillin, tetracycline or other antibiotics. Production of a particular product based on temperature sensitivity may also serve as an appropriate marker.

Prokaryotic or eukaryotic cells transformed with the polynucleotides of the present invention will be useful not only for the production of the nucleic acids and polypeptides of the present invention, but also, for example, in studying the characteristics of MTS polypeptides.

Antisense polynucleotide sequences are useful in preventing or diminishing the expression of the MTS locus, as will be appreciated by those skilled in the art. For example, polynucleotide vectors containing all or a portion of the MTS locus or other sequences from the MTS region (particularly those flanking the MTS locus) may be placed under the control of a promoter in an antisense orientation and introduced into a cell. Expression of such an antisense construct within a cell will interfere with MTS transcription and/or translation and/or replication.

Cycline and Cdks are ubiquitous cell-cycle control elements in eukaryotes. Such proteins were initially discovered in yeast, and have been found in marine invertebrates, amphibians and mammals, including mouse, rabbit and humans. Homologous cell-cycle control genes are identified in other species by using probes and/or primers based on the gene sequence in one species. Thus, probes and primers based on the MTS gene sequences disclosed herein are used to identify homologous MTS gene sequences and proteins in other species. These MTS gene sequences and proteins are used in the diagnostic/prognostic, therapeutic and drug screening methods described herein for the species from which they have been isolated.

Methods of Use: Nucleic Acid Diagnosis and Diagnostic Kits

In order to detect the presence of a MTS allele predisposing an individual to cancer, a biological sample such as blood is prepared and analyzed for the presence or absence of susceptibility alleles of MTS. In order to detect the presence of neoplasia, the progression toward malignancy of a precursor lesion, or as a prognostic indicator, a biological sample of the lesion is prepared and analyzed for the presence or absence of neoplastic alleles of MTS. Results of these tests and interpretive information are returned to the health care provider for communication to the tested individual. Such diagnoses may be performed by diagnostic laboratories, or, alternatively, diagnostic kits are manufactured and sold to health care providers or to private individuals for self-diagnosis.

Initially, the screening method involves amplification of the relevant MTS sequences, e.g., by PCR, followed by DNA sequence analysis. In another preferred embodiment of the invention, the screening method involves a non-PCR based strategy. Such screening methods include two-step label amplification methodologies that are well known in the art. Both PCR and non-PCR based screening strategies can detect target sequences with a high level of sensitivity.

The most popular method used today is target amplification. Here, the target nucleic acid sequence is amplified with polymerases. One particularly preferred method using polymerase-driven amplification is the polymerase chain reaction (PCR). A preferred PCR based strategy contemplated within the scope of this invention is provided in Example 1. The polymerase chain reaction and other polymerase-driven amplification assays can achieve over a million-fold increase in copy number through the use of polymerase-driven amplification cycles. Once amplified, the resulting nucleic acid can be sequenced or used as a substrate for DNA probes.

When the probes are used to detect the presence of the target sequences (for example, in screening for cancer susceptibility), the biological sample to be analyzed, such as blood or serum, may be treated, if desired, to extract the nucleic acids. The sample nucleic acid may be prepared in various ways to facilitate detection of the target sequence; e.g. denaturation, restriction digestion, electrophoresis or dot blotting. The targeted region of the analyte nucleic acid usually must be at least partially single-stranded to form hybrids with the targeting sequence of the probe. If the sequence is naturally single-stranded, denaturation will not be required. However, if the sequence is double-stranded, the sequence will probably need to be denatured. Denaturation can be carried out by various techniques known in the art.

Analyte nucleic acid and probe are incubated under conditions which promote stable hybrid formation of the target sequence in the probe with the putative targeted sequence in the analyte. The region of the probes which is used to bind to the analyte can be made completely complementary to the targeted region of human chromosome 9p. Therefore, high stringency conditions are desirable in order to prevent false positives. However, conditions of high stringency are used only if the probes are complementary to regions of the chromosome which are unique in the genome. The stringency of hybridization is determined by a number of factors during hybridization and during the washing procedure, including temperature, ionic strength, base composition, probe length, and concentration of formamide. These factors are outlined in, for example, Maniatis et al., 1982 and Sambrook et al., 1989. Under certain circumstances, the formation of higher order hybrids, such as triplexes, quadraplexes, etc., may be desired to provide the means of detecting target sequences.

Detection, if any, of the resulting hybrid is usually accomplished by the use of labeled probes. Alternatively, the probe may be unlabeled, but may be detectable by specific binding with a ligand which is labeled, either directly or indirectly. Suitable labels, and methods for labeling probes and ligands are known in the art, and include, for example, radioactive labels which may be incorporated by known methods (e.g., nick translation, random priming or kinasing), biotin, fluorescent groups, chemiluminescent groups (e.g., dioxetanes, particularly triggered dioxetanes), enzymes, antibodies and the like. Variations of this basic scheme are known in the art, and include those variations that facilitate separation of the hybrids to be detected from extraneous materials and/or that amplify the signal from the labeled moiety. A number of these variations are reviewed in, e.g., Matthews & Kricka, 1988; Landegren et al., 1988; Mittlin, 1989; U.S. Pat. No. 4,868,105, and in EPO Publication No. 225,807.

As noted above, non-PCR based screening assays are also contemplated in this invention. An exemplary non-PCR based procedure is provided in Example 16. This procedure hybridizes a nucleic acid probe (or an analog such as a methyl phosphonate backbone replacing the normal phosphodiester), to the low level DNA target. This probe may have an enzyme covalently linked to the probe, such that the covalent linkage does not interfere with the specificity of the hybridization. This enzyme-probe-conjugate-target nucleic acid complex can then be isolated away from the free probe enzyme conjugate and a substrate is added for enzyme detection. Enzymatic activity is observed as a change in color development or luminescent output resulting in a $10^3$–$10^6$ increase in sensitivity. For an example relating to the preparation of oligodeoxynucleotide-alkaline phosphatase conjugates and their use as hybridization probes see Jablonski et al., 1986.

Two-step label amplification methodologies are known in the art. These assays work on the principle that a small ligand (such as digoxigenin, biotin, or the like) is attached to a nucleic acid probe capable of specifically binding MTS. An exemplary probe for MTS1 is the nucleic acid probe corresponding to nucleotide positions 448 to 498 of SEQ ID NO:4. Allele specific probes are also contemplated within the scope of this example and exemplary allele specific probes include probes encompassing the predisposing mutations summarized in Table 4 and the somatic mutations in tumors summarized in Table 6.

In one example, the small ligand attached to the nucleic acid probe is specifically recognized by an antibody-enzyme conjugate. In one embodiment of this example, digoxigenin is attached to the nucleic acid probe. Hybridization is detected by an antibody-alkaline phosphatase conjugate which turns over a chemiluminescent substrate. For methods for labeling nucleic acid probes according to this embodiment see Martin et al., 1990. In a second example, the small ligand is recognized by a second ligand-enzyme conjugate that is capable of specifically complexing to the first ligand. A well known embodiment of this example is the biotin-avidin type of interactions. For methods for labeling nucleic acid probes and their use in biotin-avidin based assays see Rigby, et al., 1977 and Nguyen, et al. (1992).

It is also contemplated within the scope of this invention that the nucleic acid probe assays of this invention will employ a cocktail of nucleic acid probes capable of detecting MTS genes. Thus, in one example to detect the presence of MTS1 in a cell sample, more than one probe complementary to MTS1 is employed and in particular the number of different probes is alternatively 2, 3, or 5 different nucleic acid probe sequences. In another example, to detect the presence of mutations in the MTS1 gene sequence in a patient, more than one probe complementary to MTS1 is employed where the cocktail includes probes capable of binding to the allele-specific mutations identified in populations of patients with alterations in MTS1. In this embodiment, any number of probes can be used, and will preferably include probes corresponding to the major gene mutations identified as predisposing an individual to breast cancer. Some candidate probes contemplated within the scope of the invention include probes that include the allele-specific mutations identified in Tables 3 and 5.

Methods of Use: Peptide Diagnosis and Diagnostic Kits

The neoplastic condition of lesions can also be detected on the basis of the alteration of wild-type MTS polypeptide. Such alterations can be determined by sequence analysis in accordance with conventional techniques. More preferably, antibodies (polyclonal or monoclonal) are used to detect differences in, or the absence of MTS peptides. In a preferred embodiment of the invention, antibodies will immunoprecipitate MTS proteins from solution as well as react with MTS protein on Western or immunoblots of polyacrylamide gels. In another preferred embodiment, antibodies will detect MTS proteins in paraffin or frozen tissue sections, using immunocytochemical techniques. Techniques for raising and purifying antibodies are well known in the art, and any such techniques may be chosen to achieve the preparation of the invention.

Preferred embodiments relating to methods for detecting MTS or its mutations include enzyme linked immunosorbent assays (ELISA), radioimmunoassays (RIA), immunoradiometric assays (IRMA) and immunoenzymatic assays (IEMA), including sandwich assays using monoclonal and/or polyclonal antibodies. Exemplary sandwich assays are described by David et al., in U.S. Pat. Nos. 4,376,110 and 4,486,530, hereby incorporated by reference, and exemplified in Example 19.

Methods of Use: Drug Screening

The present invention is particularly useful for screening compounds by using the Cdk polypeptides or binding fragments thereof in any of a variety of drug screening techniques. Preferably, Cdk4 is utilized. The Cdk polypeptide or fragment employed in such a test may either be free in solution, affixed to a solid support, or borne on a cell surface.

One method of drug screening utilizes eukaryotic or prokaryotic host cells which are stably transformed with recombinant polynucleotides expressing the polypeptide or fragment, preferably in competitive binding assays. Such cells, either in viable or fixed form, can be used for standard binding assays. One may measure, for example, for the formation of complexes between a Cdk polypeptide or fragment and the agent being tested, or examine the degree to which the formation of a complex between a Cdk polypeptide or fragment and MTS polypeptide or fragment is interfered with by the agent being tested.

Thus, the present invention provides methods of screening for drugs comprising contacting such an agent with a Cdk polypeptide or fragment thereof and assaying: 1) for the presence of a complex between the agent and the Cdk polypeptide or fragment, or 2) for the presence of a complex between the Cdk polypeptide or fragment and a ligand, by methods well known in the art. The activity of Cdk is also measured to determine if the agent is capable of inhibiting Cdk, and hence capable of regulating the cell cycle. In such competitive binding assays the Cdk polypeptide or fragment is typically labeled. Free Cdk polypeptide or fragment is separated from that present in a protein:protein complex, and the amount of free (i.e., uncomplexed) label is a measure of the binding of the agent being tested to Cdk or its interference with Cdk:MTS polypeptide binding, respectively. Small peptides of MTS polypeptide (peptide mimetics) are analyzed in this manner to identify those which have Cdk inhibitory activity.

Another technique for drug screening provides high throughput screening for compounds having suitable binding affinity to the Cdk polypeptides and is described in detail in Geysen, PCT published application WO 84/03564, published Sep. 13, 1984. Briefly stated, large numbers of different small peptide test compounds are synthesized on a solid substrate, such as plastic pins or some other surface. The peptide test compounds are reacted with Cdk polypeptide and washed. Bound Cdk polypeptide is then detected by methods well known in the art.

Purified Cdk can be coated directly onto plates for use in the aforementioned drug screening techniques. However, non-neutralizing antibodies to the polypeptide can be used to capture antibodies to immobilize the Cdk polypeptide on the solid phase.

The present invention also contemplates the use of competitive drug screening assays, in which neutralizing antibodies capable of specifically binding the Cdk polypeptide compete with a test compound for binding to the Cdk polypeptide or fragments thereof. In this manner, the antibodies can be used to detect the presence of any peptide which shares one or more antigenic determinants of the Cdk polypeptide.

A further technique for drug screening involves the use of host eukaryotic cell lines or cells (such as described above) which have a nonfunctional MTS gene. These host cell lines or cells are defective in cell cycle control at the Cdk level. The host cell lines or cells are grown in the presence of drug compound. The rate of growth of the host cells is measured to determine if the compound is capable of regulating the cell cycle. One means of measuring the growth rate is by determining the biological activity of the Cdks, preferably Cdk4.

Methods of Use: Rational Drug Design

The goal of rational drug design is to produce structural analogs of biologically active polypeptides of interest or of small molecules with which they interact (e.g., agonists, antagonists, inhibitors) in order to fashion drugs which are, for example, more active or stable forms of the polypeptide, or which, e.g., enhance or interfere with the function of a polypeptide in vivo. See, e.g., Hodgson, 1991. In one approach, one first determines the three-dimensional structure of a protein of interest (e.g., p16 or Cdk4) or, for example, of the Cdk4-p16 complex, by x-ray crystallography, by computer modeling or most typically, by a combination of approaches. Less often, useful information regarding the structure of a polypeptide may be gained by modeling based on the structure of homologous proteins. An example of rational drug design is the development of HIV protease inhibitors (Erickson et al., 1990). In addition, peptides (e.g., p16 or Cdk4) are analyzed by an alanine scan (Wells, 1991). In this technique, an amino acid residue is replaced by Ala, and its effect on the peptide's activity is determined. Each of the amino acid residues of the peptide is analyzed in this manner to determine the important regions of the peptide.

It is also possible to isolate a target-specific antibody, selected by a functional assay, and then to solve its crystal structure. In principle, this approach yields a pharmacore upon which subsequent drug design can be based. It is possible to bypass protein crystallography altogether by generating anti-idiotypic antibodies (anti-ids) to a functional, pharmacologically active antibody. As a mirror image of a mirror image, the binding site of the anti-ids would be expected to be an analog of the original receptor. The anti-id could then be used to identify and isolate peptides from banks of chemically or biologically produced banks of peptides. Selected peptides would then act as the pharmacore.

Thus, one may design drugs which have, e.g., improved MTS activity or stability or which act as inhibitors, agonists, antagonists, etc. of MTS activity. By virtue of the availability of cloned MTS sequences, sufficient amounts of the MTS polypeptide may be made available to perform such analytical studies as x-ray crystallography. In addition, the knowledge of the MTS protein sequence provided herein will guide those employing computer modeling techniques in place of, or in addition to x-ray crystallography.

Methods of Use: Gene Therapy

According to the present invention, a method is also provided of supplying wild-type MTS function to a cell which carries mutant MTS alleles. Supplying such a function should suppress neoplastic growth of the recipient cells. The wild-type MTS gene or a part of the gene may be introduced into the cell in a vector such that the gene remains extrachromosomal. In such a situation, the gene will be expressed by the cell from the extrachromosomal location. If a gene portion is introduced and expressed in a cell carrying a mutant MTS allele, the gene portion should encode a part of the MTS protein which is required for non-neoplastic growth of the cell. More preferred is the situation where the wild-type MTS gene or a part thereof is introduced into the mutant cell in such a way that it recombines with the endogenous mutant MTS gene present in the cell. Such recombination requires a double recombination event which results in the correction of the MTS gene mutation. Vectors for introduction of genes both for recombination and for extrachromosomal maintenance are known in the art, and any suitable vector may be used. Methods for introducing DNA into cells such as electroporation, calcium phosphate co-precipitation and viral transduction are known in the art, and the choice of method is within the competence of the routineer. Cells transformed with the wild-type MTS gene can be used as model systems to study cancer remission and drug treatments which promote such remission.

As generally discussed above, the MTS gene or fragment, where applicable, may be employed in gene therapy methods in order to increase the amount of the expression products of such genes in cancer cells. Such gene therapy is particularly appropriate for use in both cancerous and pre-cancerous cells, in which the level of MTS polypeptide is absent or diminished compared to normal cells. It may also be useful to increase the level of expression of a given MTS gene even in those tumor cells in which the mutant gene is expressed at a "normal" level, but the gene product is not fully functional.

Gene therapy would be carried out according to generally accepted methods, for example, as described by Friedman in *Therapy for Genetic Disease,* T. Friedman, ed., Oxford University Press (1991), pp. 105–121. Cells from a patient's tumor would be first analyzed by the diagnostic methods described above, to ascertain the production of MTS polypeptide in the tumor cells. A virus or plasmid vector, containing a copy of the MTS gene linked to expression control elements and capable of replicating inside the tumor cells, is prepared. Suitable vectors are known, such as disclosed in U.S. Pat. No. 5,252,479 and PCT published application WO 93/07282. The vector is then injected into the patient, either locally at the site of the tumor or systemically (in order to reach any tumor cells that may have metastasized to other sites). If the transfected gene is not permanently incorporated into the genome of each of the targeted tumor cells, the treatment may have to be repeated periodically. Since MTS polypeptides are intimately involved in the control of the cell cycle, it is preferred that the MTS gene be introduced with its own regulatory elements, to avoid constitutive expression of MTS polypeptide by all cells which take up the gene.

Gene transfer systems known in the art may be useful in the practice of the gene therapy methods of the present invention. These include viral and nonviral transfer methods. A number of viruses have been used as gene transfer vectors, including papovaviruses (e.g., SV40, Madzak et al., 1992), adenovirus (Berkner, 1992; Berkner et al., 1988; Gorziglia and Kapikian, 1992; Quantin et al., 1992; Rosenfeld et al., 1992; Wilkinson et al., 1992; Stratford-Perricaudet et al., 1990), vaccinia virus (Moss, 1992), adeno-associated virus (Muzyczka, 1992; Ohi et al., 1990), herpesviruses including HSV and EBV (Margolskee, 1992; Johnson et al., 1992; Fink et al., 1992; Breakfield and Geller, 1987; Freese et al., 1990), and retroviruses of avian (Brandyopadhyay and Temin, 1984; Petropoulos et al., 1992), murine (Miller, 1992; Miller et al., 1985; Sorge et al., 1984; Mann and Baltimore, 1985; Miller et al., 1988), and human origin (Shimada et al., 1991; Helseth et al., 1990; Page et al., 1990; Buchschacher and Panganiban, 1992). Most human gene therapy protocols have been based on disabled murine retroviruses.

Nonviral gene transfer methods known in the art include chemical techniques such as calcium phosphate coprecipitation (Graham and van der Eb, 1973; Pellicer et al., 1980); mechanical techniques, for example microinjection (Anderson et al., 1980; Gordon et al., 1980; Brinster et al., 1981; Constantini and Lacy, 1981); membrane fusion-mediated transfer via liposomes (Felgner et al., 1987; Wang and Huang, 1989; Kaneda et al, 1989; Stewart et al., 1992; Nabel et al., 1990; Lim et al., 1992); and direct DNA uptake and receptor-mediated DNA transfer (Wolff et al., 1990; Wu et al., 1991; Zenke et al., 1990; Wu et al., 1989b; Wolff et al., 1991; Wagner et al., 1990; Wagner et al., 1991; Cotten et al., 1990; Curiel et al., 1991a; Curiel et al., 1991b). Viral-mediated gene transfer can be combined with direct in vivo gene transfer using liposome delivery, allowing one to direct the viral vectors to the tumor cells and not into the surrounding nondividing cells. Alternatively, the retroviral vector producer cell line can be injected into tumors (Culver et al., 1992). Injection of producer cells would then provide a continuous source of vector particles. This technique has been approved for use in humans with inoperable brain tumors.

In an approach which combines biological and physical gene transfer methods, plasmid DNA of any size is combined with a polylysine-conjugated antibody specific to the adenovirus hexon protein, and the resulting complex is bound to an adenovirus vector. The trimolecular complex is then used to infect cells. The adenovirus vector permits efficient binding, internalization, and degradation of the endosome before the coupled DNA is damaged.

Liposome/DNA complexes have been shown to be capable of mediating direct in vivo gene transfer. While in standard liposome preparations the gene transfer process is nonspecific, localized in vivo uptake and expression have been reported in tumor deposits, for example, following direct in situ administration (Nabel, 1992).

Methods of Use: Peptide Therapy

Peptides which have MTS activity can be supplied to cells which carry mutant or missing MTS alleles. The sequences of the MTS proteins are disclosed (SEQ ID NO:2, SEQ ID NO:14 and SEQ ID NO:16). Protein can be produced by expression of the cDNA sequence in bacteria, for example, using known expression vectors. Alternatively, MTS polypeptide can be extracted from MTS-producing mammalian cells. In addition, the techniques of synthetic chemistry can be employed to synthesize MTS protein. Any of such techniques can provide the preparation of the present invention which comprises the MTS protein. The preparation is substantially free of other human proteins. This is most readily accomplished by synthesis in a microorganism or in vitro.

Active MTS molecules can be introduced into cells by microinjection or by use of liposomes, for example. Alternatively, some active molecules may be taken up by cells, actively or by diffusion. Extracellular application of the MTS gene product may be sufficient to affect tumor growth. Supply of molecules with MTS activity should lead to partial reversal of the neoplastic state. Other molecules with MTS activity (for example, peptides, drugs or organic compounds) may also be used to effect such a reversal. Modified polypeptides having substantially similar function are also used for peptide therapy.

Methods of Use: Transformed Hosts

Similarly, cells and animals which carry a mutant MTS allele can be used as model systems to study and test for substances which have potential as therapeutic agents. The cells are typically cultured epithelial cells. These may be isolated from individuals with MTS mutations, either somatic or germline. Alternatively, the cell line can be engineered to carry the mutation in the MTS allele, as described above. After a test substance is applied to the cells, the neoplastically transformed phenotype of the cell is determined. Any trait of neoplastically transformed cells can be assessed, including anchorage-independent growth, tumorigenicity in nude mice, invasiveness of cells, and growth factor dependence. Assays for each of these traits are known in the art.

Animals for testing therapeutic agents can be selected after mutagenesis of whole animals or after treatment of germline cells or zygotes. Such treatments include insertion of mutant MTS alleles, usually from a second animal species, as well as insertion of disrupted homologous genes. Alternatively, the endogenous MTS gene(s) of the animals may be disrupted by insertion or deletion mutation or other genetic alterations using conventional techniques (Capecchi, 1989; Valancius and Smithies, 1991; Hasty et al., 1991; Shinkai et al., 1992; Mombaerts et al., 1992; Philpott et al., 1992; Snouwaert et al., 1992; Donehower et al., 1992). After test substances have been administered to the animals, the growth of tumors must be assessed. If the test substance prevents or suppresses the growth of tumors, then the test substance is a candidate therapeutic agent for the treatment of the cancers identified herein.

The present invention is described by reference to the following Examples, which are offered by way of illustration and are not intended to limit the invention in any manner. Standard techniques well known in the art or the techniques specifically described below were utilized.

EXAMPLE 1

Materials and Methods

A. MTS Pedigrees

FIGS. 1A–1D show Kindreds 3137, 3161, 3355 and 1771, respectively. The occurrence of cancer in these kindreds is shown in the Figures. All melanomas in kindred 3137 carry the susceptible haplotype, and other cancers carrying the susceptible haplotype are also shown for this kindred. All melanomas in kindreds 3161 and 3355 carry the susceptible haplotype. A mutation in MTS was identified for the cancers in kindred 1771.

B. Tumor Cell Lines

Seventy-six melanoma cell lines were obtained from the Ludwig Institute for Cancer Research, Memorial Sloan-Kettering Cancer Center, and 8 melanoma cell lines and five non-melanoma lines from the American Type Culture Collection (ATCC).

C. Preparation and analysis of tumor cell line DNA

DNA was isolated from cell lines by the addition of approximately $1\times10^7$ cells to 3 ml lysis buffer (0.1 M NaCl; 0.1 M TrisHCl pH8.0; 5 mM EDTA; 0.5% SDS), followed by vortexing and incubation at 65° C. for 30 minutes. 0.5 ml of 8M KOAc was added, and the reaction was mixed and incubated on ice for 30 minutes. After centrifugation (five minutes at 10,000×g), the supernatant was precipitated with an equal volume of 95% ethanol and centrifuged again (15 minutes at 10,000×g). The DNA was resuspended in 50–200 ml $H_2O$.

D. PCR Reactions 50 ng template was added to 30 pmol of each oligonucleotide primer in a 20 ml reaction mixture that contained 0.1 mM dNTPs, 10 mM Tris-HCl (pH 8.3), 50 mM KCl, 2 mM $MgCl_2$, 0.01% gelatin, and 1 unit Amplitaq polymerase (Perkin-Elmer). Samples were cycled in a Perkin-Elmer 9600 thermal cycler 35 times at 94° C. for 10 seconds, 55° C. for 10 seconds, and 72° C. for 10 seconds. The products were visualized after electrophoresis through either 1.5% agarose (SeaKem) or 3% NuSieve 3:1 agarose (FMC BioProducts) by ethidium bromide staining.

E. YACs

Yeast artificial chromosomes (YACs) containing markers in the MTS region were obtained by screening the CEPH YAC libraries with IFNA, D9S171, and D9S126 using PCR conditions described above. Yeast strains containing YACs were grown at 30° C. for three days with vigorous shaking in AHC medium (10 g/l casein hydrolysate-acid; 1.7 g/l yeast nitrogen base; 5 g/l ammonium sulfate; 20 mg/l adenine hemisulfate; 2% glucose; pH=5.8). Yeast DNA was prepared as described by Ausubel et al., 1992.

F. Phage Library Construction

Yeast genomic DNA containing YAC DNA was digested to completion with BamHI, inserted into BamHI-digested EMBL3 phage arms (Promega) using T4 DNA ligase (Boehringer-Mannheim), and packaged in vitro with Gigapack II extracts (Stratagene). Phage were grown on E. coli strain C600. Recombinant phage containing human DNA were identified by hybridization with $^{32}$P-labeled human $C_o$t-1 DNA (GIBCO-BRL). Phage including human sequences joined to YAC vector (end clones) were identified by screening with PCR fragments containing sequences from the YAC left or right arm. Hybridization and washing were carried out under standard conditions (Middleton et al., 1991). Positive plaques were picked and purified by replating three times. Phage DNA was prepared using Qiaex columns (Qiagen).

G. Cosmid Library Construction

Yeast genomic DNA containing YAC DNA was digested partially with Sau3A and fractionated by size on a linear (10–40%) sucrose gradient, as described in Maniatis et al., 1982. SuperCos 1 cosmid vector (Stratagene) was prepared according to manufacturer's directions, mixed with insert DNA at a mass ratio of 4:1 (insert:vector), treated with ligase, and packaged in vitro, as described above. Cosmids were introduced into DH5α host cells and plated at a density of 2000 colonies per 15 cm petri dish. Colony hybridization was carried out as described above and in Maniatis et al., 1982.

H. P1 clones

P1 clones spanning the MTS region were obtained from Genome Systems, Inc., St. Louis, Mo., by screening with STSs prepared as described herein. DNA from these clones was isolated by alkaline lysis (Birnboim and Doly, 1979), followed by cesium chloride gradient centrifugation (Maniatis et al., 1982).

I. Generation of STSs

STSs were generated by sequencing 1.0 mg of P1, cosmid, or template DNA with oligonucleotides complementary to sequences flanking the cloning site of the P1 vector (pSacBII), SuperCos 1 vector; or the EMBL3 vector. Sequencing was done on an ABI 373A DNA sequencing system with the PRISM Ready Reaction DyeDeoxy Terminator Cycle Sequencing Kit (ABI). STSs were designed to be as close as possible to 20 bp long and to have a Tm as close as possible to 60° C.

J. Germline mutations in MTS1 in melanoma-prone kindreds.

Genomic DNA from carrier individuals was prepared from blood using standard methods. Primers were designed at intron positions to amplify coding exons 1 or 2 from MTS1, or coding exon 2 from MTS2 using 20 ng DNA from each sample. PCR reactions used the standard buffer, except DMSO was added to a final concentration of 5%. Cycle sequencing reactions were carried out using α-$P^{32}$-dATP on the amplified products using primers positioned at different points in the sequence. The sequencing products were analyzed on 6% denaturing polyacrylamide gels by loading all the (A) reactions side by side, followed by the (C) reactions, etc. All polymorphisms were confirmed by sequence analysis of the opposite strand.

EXAMPLE 2

Localization of MTS Using Genetically Linked Markers

To analyze tumor cell lines for homozygous deletions in the 9p21 region, a set of markers known to be linked to MTS was utilized. These markers were used originally to demonstrate dramatic linkage (LOD score=12.7) of melanoma predisposition in 10 Utah kindreds and one Texas kindred (Cannon-Albright et al., 1992). The markers included a sequence from the α-interferon gene cluster (IFNA) (Kwiatkowski & Diaz, 1992) which was the most distal marker tested, a proximal marker (D9S104), and four additional markers in between (D9S171, D9S126, D9S161, and D9S169) (Cannon-Albright et al., 1992). From genetic studies, the linear sequence of the intervening markers was thought to be: D9S171, D9S126, D9S161, D9S169. The IFNA marker consisted of an oligonucleotide primer pair that amplified two fragments from wildtype genomic DNA: a roughly 138–150 bp polymorphic fragment (IFNA-1) that contains a poly(CA) stretch, and a roughly 120 bp invariant fragment (IFNA-s). The location of IFNA-s with respect to IFNA-1 was unknown.

Five non-melanoma tumor cell lines reported previously to contain deletions were analyzed using genetic markers. Each cell line revealed homozygous deletions of at least one of the markers tested (Table 1). No homozygous deletions were identified using D9S161, D9S169 or D9S104. The minimum region of overlap among these deletions was flanked by IFNA-1 and D9S171. This suggested that the region between these two markers contains a gene(s) that is involved in tumor suppression, possibly MTS. The genomic region between D9S171 and IFNA-1, particularly in the vicinity of IFNA-s, was then studied in further detail.

TABLE 1

Homozygous Deletions in Tumor Cell Lines Detected with Genetic Markers Linked to MTS

| Tumor Cell Lines | Markers | | | | | | |
|---|---|---|---|---|---|---|---|
| | IFNA-1 | IFNA-s | D9S171 | D9S126 | D9S161 | D9S169 | D9S104 |
| U-138 | − | − | − | − | + | + | + |
| U-118 | − | − | − | − | + | + | + |
| U-87 | − | − | + | + | + | + | + |
| A-172 | + | − | + | + | + | + | + |
| H4 | − | − | − | − | + | + | + |

NOTE: All cell lines are either gliomas or neuroblastomas available from the ATCC.

EXAMPLE 3

Genomic Clones in the MTS Region

Figure 2:
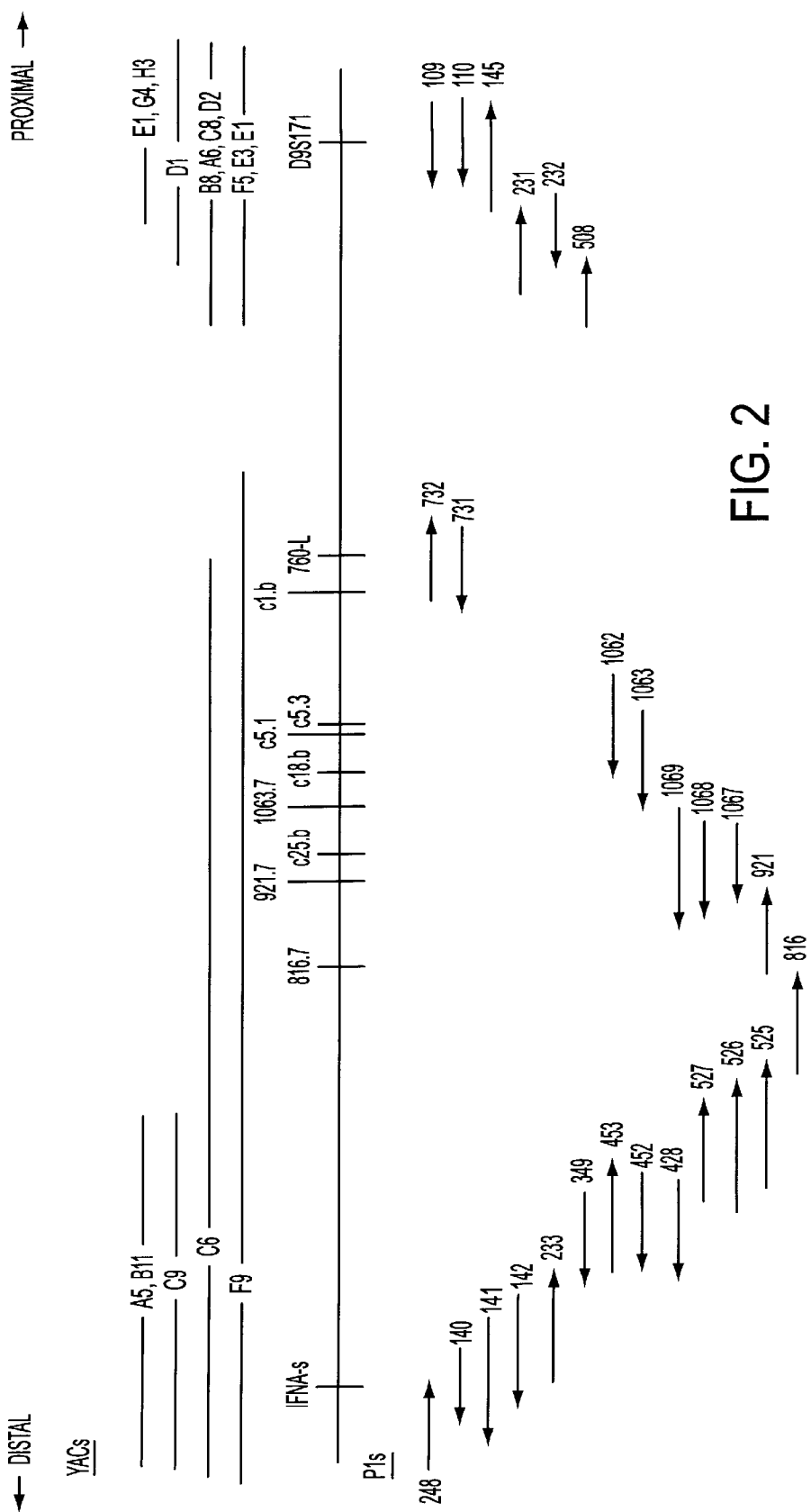
FIG. 2 shows YAC and P1 clones in the region bounded by IFNA-s and D9S171. The centromere is to the right. For P1 clones, the arrow points in the direction of the T7 promoter sequence in the vector. YACs that are grouped together represent clones that are similar based on mapping STSs in the region. These YACs are presumed not to be identical. YACs A5, B11, C6 and F9 contain INF-1 and IFN-s. YACs D1, F5 and E3 contain D9S126 and D9S171. Neither the proximal ends of YACs that include D9S171 nor the distal ends of YACs that include IFNA-s are shown. Distances are not necessarily drawn to scale. The markers internal to IFNA-s and D9S171 are depicted in FIG. 2. Markers that begin with "c" are derived from cosmid end sequences. The cosmids are not shown. The distances between c1.b and c5.3 and between 760-L and D9S171 are unknown.

To obtain genomic clones of the region surrounding IFNA-s, CEPH YAC libraries were screened (Cohen et al., 1993). Eleven YACs were identified which contained the D9S171 marker and 5 that contained IFNA-s. No YACs were isolated which included both D9S171 and IFNA-s (FIG. 2). Three of the YAC clones (C9, C6, F9) were subcloned into phage and one YAC (C6) was subcloned into a cosmid vector. These and cosmid clones provided a convenient way to produce STSs internal to known genetic markers and to expedite the chromosomal walk described below.

To provide an independent source of genomic DNA for construction of a contiguous genomic map of the region and to aid in production of STSs, a chromosomal walk was initiated in P1 clones from IFNA-s extending toward D9S171, from D9S171 extending back toward IFNA-s, and from the YAC C6 ends in both directions. A total of 27 P1 clones were isolated as part of this chromosomal walk (FIG. 2). The ordered P1s formed a contiguous assembly that stretched from IFNA-s to D9S171 with two gaps. P1 clones as well as several phage and cosmid clones were used to generate a fine structure map of the MTS region.

EXAMPLE 4

Fine Structure Analysis of MTS Region

To construct a more detailed molecular map of the MTS region, additional markers were required. DNA sequences obtained from the genomic clones were used to design PCR primers for STSs. These STSs served in turn to help order the P1 and YAC clones. A total of 54 STSs from the region between IFNA-s and D9S171 were the primary basis for developing a detailed physical map of the MTS region (FIG. 2). These STS primer sequences have been deposited in the Genome Database.

Figure 3:
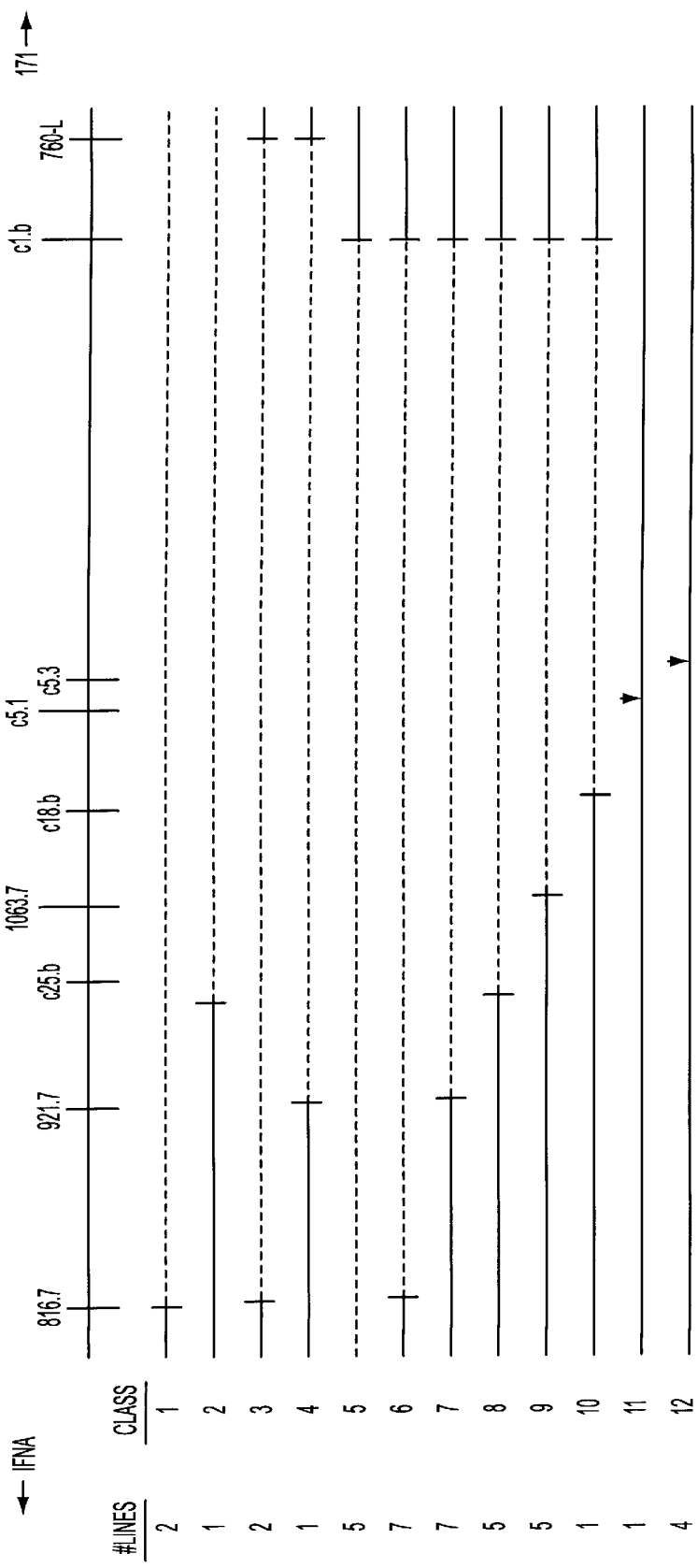
FIG. 3 shows a diagram of deletions observed in melanoma cell lines. The deletions fall into 12 classes, based on the set of markers which are deleted. Eleven cell lines lacked all markers depicted in the figure. This class is not shown. The number of representatives of each of the 12 other classes is shown in the column labeled "# lines." Locations of the deletion breakpoints for classes 1–10 are portrayed as falling at the marker adjacent to the deleted DNA; that is, the last positive marker in the series leading up to the deletion. For classes 11 and 12, the sites of deletions are shown by filled triangles.

The set of new markers stretching from IFNA-s to D9S171 was used to test 84 melanoma cell lines for homozygous deletions in the MTS region. A total of 52 lines revealed regions of homozygous deletion (FIG. 3). Several of the deletions were extensive; for example, 13 lines were missing a region that included both 816.7 and 760-L.

For the purpose of localizing MTS, the most informative tumor lines fell into two groups (FIG. 3): i) those that contained deletions of c5.1 alone (class 11); and, ii) those that contained deletions of c5.3 alone (class 12). A total of 5 melanoma lines fell into these categories. In all cases where deletions were detected, the deletion appeared to be simple; that is, there was no evidence of multiple deletion events in the region between IFNA-s and D9S171. Together the lines harboring deletions delineated a region of deletion overlap centered around markers c5.1 and c5.3, making the development of a complete physical map of the region from IFNA-s to D9S171 unnecessary.

EXAMPLE 5

Identification of Cosmid c5 and P1 Colonies P1062 and P1063 as Containing MTS

A. Placement of genetic markers

Analysis of YAC clones and of deletions in tumor lines yielded results consistent with the genetic placement of markers: IFNA, D9S171, D9S126. Three YACs contained both D9S171 and D9S126, while four YACs contained IFNA-1 and IFNA-s (FIG. 2). None contained both D9S171 and IFNA. This suggested that: i) IFNA-1 and IFNA-s are closely linked, and ii) D9S126 and D9S171 are linked. These results were confirmed by cell line deletions. Most cell lines that were missing D9S171 also lacked D9S126. Conversely, line U-87, although testing positive for D9S171 and D9S126, lacked IFNA-s and IFNA-1 (Table 1). One melanoma cell line, SK-MEL-5, lacked IFNA-s, D9S171 and D9S126, but not IFNA-1. Thus, IFNA-1 must be distal to IFNA-s. Another melanoma line, SK-Mel-Zan, contained a deletion that included IFNA-1, IFNA-s and D9S171 but not D9S126, placing D9S171 between IFNA-s and D9S126. Collectively, these findings support the marker order given in Table 1.

The human α-interferon gene family consists of over 23 genes and pseudogenes located on chromosome 9p. This gene cluster has been cloned and sorted into 10 linkage groups (Henco et al., 1985). The linkage groups have been partially ordered by analysis of deletion losses of different α-interferon sequences in glioma cell lines (Olopade et al., 1992). Glioma line H4 lacks both IFNA-1 and IFNA-s. It also lacks sequences from linkage group IV (e.g., α13, α6 and α20). Glioma line A172 contains both IFNA-1 and linkage group IV, but lacks sequences from linkage groups I (e.g., α1, α19), III (e.g., α8) and IX (e.g., α2) and IFNA-s. This analysis places IFNA-1 distal to linkage groups I, III, and IX as well as IFNA-s. The distal boundary of the A172 deletion was mapped within one P1 length distal of IFNA-s. Thus, linkage groups I, III, and IX must lie proximal to a point located less than 85 kb distal to IFNA-s.

B. Physical distance between genetic markers

The results did not permit a precise estimate of the distance between IFNA-s and D9S171, since it was not possible to isolate YACs that contained both markers. Furthermore, based on mapping with STSs, none of five YACs that extended distal from IFNA-s overlapped any of the 11 YACs that extended proximal from D9S171. Given that CEPH YAC inserts average under 500 kb in length, the distance between IFNA-s and D9S171 is likely to be at least this large.

The region between IFNA-s and c5.1 was covered by nine walking steps in a P1 library. Assuming that each step is on average the length of half a P1 insert, the distance between c5.1 and IFNA-s is roughly 400 kb. Thus, the tumor suppressor gene tightly linked to c5.1 which is deleted frequently in melanoma lines must lie about 400 kb proximal to IFNA-s.

C. Deletions in tumor lines

Homozygous deletions of the 9p21 region were found in 57% of the melanoma tumors tested. Fourteen tumor lines contained deletions that extended on the proximal side through 760-L, and 16 lines contained deletions that stretched beyond 816.7 on the distal side. Assuming the deletions are causal, that is, deletions of gene(s) in this region contribute to the tumor phenotype, the tumor suppressor gene(s) must also lie between 760-L and 816.7. The smallest deletions involved markers c5.1 and c5.3. Of all of the markers tested, c5.3 was deleted from the largest number of lines, 51. Therefore, the most probable position of the tumor suppressor gene(s) is very close to c5.3 because it is the most frequently deleted marker. Four lines contained deletions of c5.3 alone (class 12) and one line lacked c5.1 alone (class 11). Both of these markers were present on the same cosmid, c5. Thus, it is likely that the tumor suppressor gene(s) includes sequences from cosmid c5. P1 clones P1062 and P1063 include sequences found in c5 and surrounding cosmids. Thus, as shown further below, P1062 and P1063 contain the entire MTS region.

The results presented in the above Examples are consistent with previous genetic studies of MTS, which found the region between IFNA-1 and D9S126 to be the most probable location for MTS (Cannon-Albright et al., 1992). Recent genetic studies have confined the location of MTS further using a polymorphic (CA) repeat that lies between IFNA-s and C5.3 on P1-452 (FIG. 2). Analysis of a recombinant chromosome using this marker places MTS proximal to P1-453. Thus, MTS maps within the region where homozygous deletions in melanoma cell lines cluster.

These results support the view that there is a tumor suppressor locus, MTS, positioned somewhere near c5.3. All the lines that contained deletions shared a common area of deleted DNA, with the exception of the set whose deletions were restricted to c5.1 or c5.3 (classes 11 and 12). There was no indication of non-overlapping deletions in this panel of cell lines other than those within cosmid c5. Therefore, there is no basis to invoke a more complex scheme involving, for example, a second tumor suppressor locus in 9p21 distant from c5.1 and c5.3.

The observation that homozygous deletions of 9p21 occur in multiple tumor types suggests that the tumor suppressor gene(s) located there may be expressed in a wide variety of tissues. Thus, the tumor suppressor gene(s) may be similar to the p53 gene in that it may participate in the development of multiple types of cancer (see further data below). Other types of cancer have been reported in melanoma-prone families (Nancarrow et al., 1993; Bergman et al., 1990). A thorough deletion analysis of a wide variety of tumor types using c5.1 and c5.3 (shown below) clarifies the importance of this tumor suppressor gene in tumors other than melanoma.

Some of the homozygous deletions observed remove many genetic markers. Fountain et al. reported that homozygous deletions of chromosome 9p21 in two different melanoma lines extended 2–3 Mb (Bergman et al., 1990). In this study, at least one line, SK-MEL-5, contained deletions extending from the most distal marker tested, IFNA-1, past D9S126, a region apparently too large to be contained on a single YAC. The preponderance of large deletions suggests that the region surrounding MTS is devoid of genes that are essential to cellular viability.

EXAMPLE 6

Isolation of MTS Candidate Genes

In the previous Examples, the results of a YAC and P1 chromosomal walk in the neighborhood of MTS were described. Fine structure-mapping experiments with STSs derived from c5 sequences showed the presence of small, non-overlapping deletions of c5 sequences in five different melanoma cell lines. Based on this result, it was probable that a tumor suppressor gene, possibly MTS, lay at least partly within c5.

A further indication that c5 contained at least one gene came from analysis of (CpG) dinucleotide frequencies in c5 and neighboring cosmids. In mammals, virtually all housekeeping genes and nearly half of all tissue-specific genes are associated with regions unusually rich in (CpG) dinucleotides (Bird, 1989; Larsen et al., 1992). Thus, the presence of such "CpG islands" is indicative of genes. Cosmids c5, c12, c57, and c59 were digested with the restriction endonucleases EagI, BssHI, and SacII, enzymes whose recognition sequences include two (CpG) pairs. Only cosmids c5 and c12 contained sites for these enzymes. Cosmid c5 contained one EagI site, at least 10 BssHI sites, and at least 12 SacII sites. The presence of the CpG islands in c5 and the overlapping cosmid c12 suggested that c5 indeed contained at least one candidate gene for MTS.

Figure 4A:
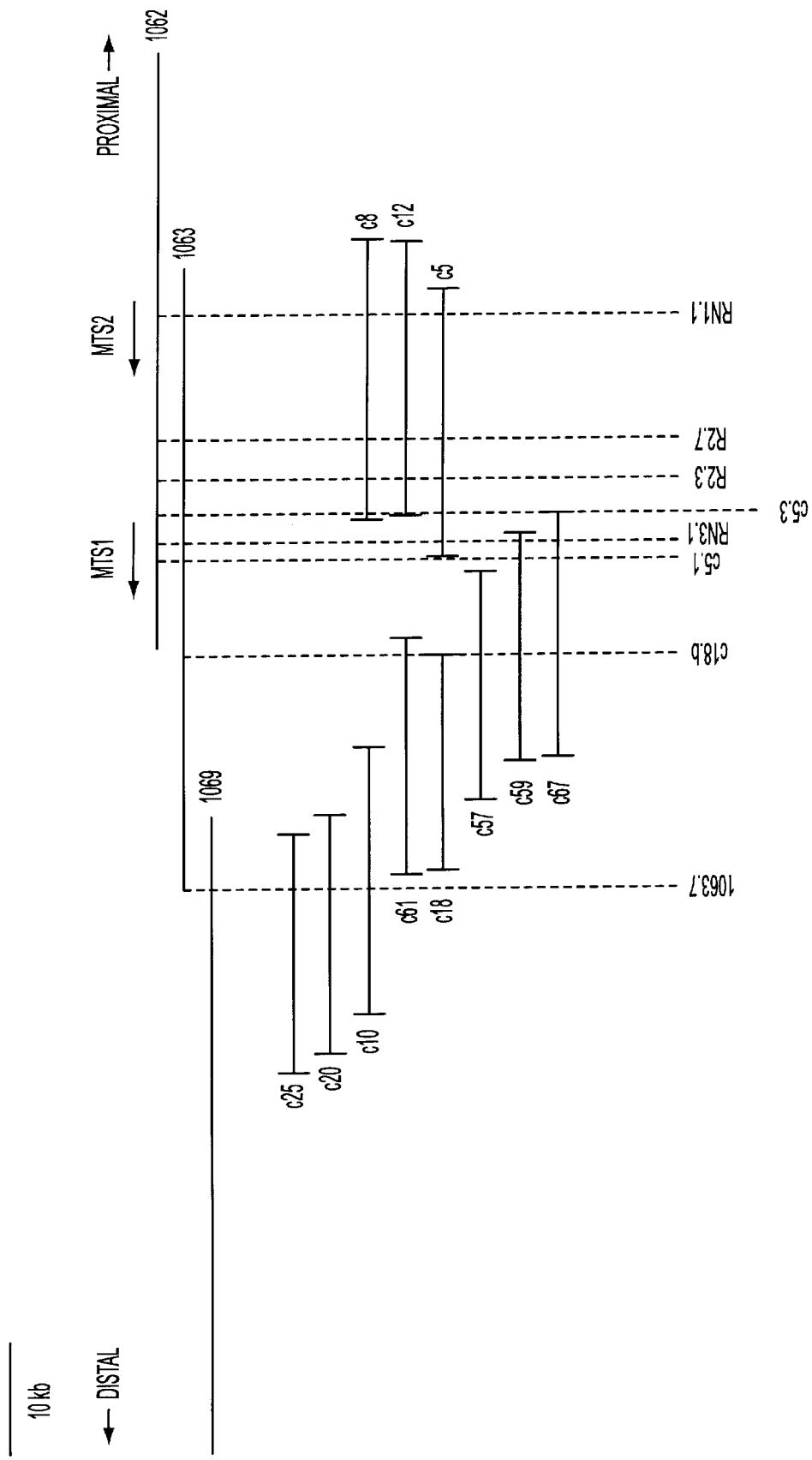
FIG. 4A shows a map of cosmid c5. Relevant STSs used for the deletion analysis are shown, as are cosmids and P1s. The c1.b marker lies proximal to P1-1062 and is not shown. The transcriptional orientations of MTS1 and MTS2 are shown by arrows.

To search for MTS, the DNA sequences of EcoRI fragments from cosmid c5 were determined. When these sequences were compared against sequences from GenBank, two distinct regions of c5 were identified that were similar to a region of a previously identified gene encoding human cyclin-dependent kinase 4 (Cdk4) inhibitor, or p16 (Serrano et al., 1993). These two genes were candidates for MTS, and were named MTS1 and MTS2. MTS1 was located near the end of cosmid c5 closest to the chromosome 9p telomere, while MTS2 was located near the centromeric end of c5. See FIG. 4B. A cosmid map showing the position of MTS1 and MTS2, as well as P1s 1062, 1063 and 1069 is shown in FIG. 4A.

A detailed comparison of genomic sequence of MTS1 from c5 with the p16 mRNA sequence revealed that MTS1 contained a stretch of 307 bp that was identical to a portion of the p16 coding sequence. This stretch of nucleotides in MTS1 was flanked by recognizable splice junction sequences. Further characterization of MTS1 showed that it included the entire coding sequence of p16 plus two introns (FIGS. 5A and 5B and FIGS. 6A and 6B). Intron 1 was located 126 bp downstream from the translational start site; intron 2 was located 11 bp upstream from the translational stop site. The two introns divided the coding sequence of MTS1 into three regions, a 5' region of 126 bp (coding exon 1), a middle region of 307 bp (coding exon 2), and a 3' region of 11 bp (coding exon 3). SEQ ID NO:3 sets forth nucleotide sequence for the 5' region, exon 1 and part of intron 1 for MTS1. SEQ ID NO:4 sets forth the nucleotide sequence for part of intron 1, exon 2 and part of intron 2 for MTS1.

MTS2 contained a region of DNA sequence nearly identical to p16 that extended from the 5' end of coding exon 2 roughly 211 bp toward intron 2 (FIG. 7A). However, the sequence similarity decreased until a point 51 bp upstream of intron 2 in MTS1 which corresponds to the location of the final codon of MTS2 (FIG. 8). Comparison of sequences from MTS1 and MTS2 (FIG. 8) showed that the sequence similarity between these two genes also extended nearly 40 nucleotides upstream from the 3' splice junction of intron 1. Thus, portions of noncoding DNA were more conserved than some areas of presumptive coding DNA. To exclude the possibility that the sequence divergence in coding DNA might be a cloning artifact, PCR primers were designed to amplify specifically across the sequence divergence point of MTS2. These primers amplified a fragment of the predicted size from cosmid, P1 and genomic DNA. Therefore, the divergent sequence located near the 3' end of exon 2 in MTS2 is a bona fide genomic sequence. SEQ ID NO:5 sets forth the nucleotide sequence for part of intron 1, "exon 2" and "intron 2" for MTS2. SEQ ID NO:15 sets forth the cDNA sequence for MTS2.

The occurrence of two closely related genes on cosmid c5 suggested that other related genes might exist in this region. To test this possibility, Southern blots were prepared from restriction enzyme digests of cosmids c5, c12, c59, P1s 1063 and 1060, and human genomic DNA. These blots were probed with a fragment containing most of exon 2 from MTS1, including the region shared with MTS2. Two EcoRI fragments were detected with the probe in both cloned DNA and genomic DNA. This result was consistent with the presence of two p16-like genes in the genome, MTS1 and MTS2. It is also consistent with the now known presence of MTS1E1β which is an alternate form of MTS1—containing Exons 2 and 3 but not Exon 1 of MTS 1.

EXAMPLE 7

Isolation of Mouse MTS1 and MTS2

Two degenerate PCR primers were designed, one based on the human MTS1 peptide sequence from amino acids 61–67, this degenerate probe having the sequence 5'-CCCGGGAATTCGA(GA)CC(GATC)AA(CT)GC (GATC)GA(CT)CC-3' (SEQ ID NO:37) and the second based on the human MTS1 peptide from amino acids 97–103, this degenerate probe having the sequence 5'-CTGCAGGATCCCCA(GATC)GC(GA)TC(GATC)C (TG)(GATC)AC (GA)TC-3' (SEQ ID NO:38). Each set of parentheses for the preceding sequences surrounds a single degenerate nucleotide, the possible bases at the site being shown within the parentheses. These two primers were used at low stringency, annealing at 42° C., in a PCR reaction with genomic mouse DNA as the template. This resulted in production of a 128 base pair fragment which was cloned and sequenced by conventional methods. The cloned fragment was used to produce a radio-labeled antisense RNA which was subsequently used to probe a mouse genomic SV129 library (Stratagene). A total of 9 clones were obtained from the screening of the mouse genomic library. One of these clones contained sequence from the MTS1 gene and eight of the clones contained sequence from the mouse MTS2 gene as determined by homology with the human genes. Repeated efforts using low stringency hybridization screens of genomic libraries or PCR with degenerate oligonucleotide primers failed to uncover additional sequence homologs in the mouse (Kamb et al., 1989).

Mouse cDNA clones corresponding to MTS1 and MTS2 were isolated by a hybrid capture RACE technique (see copending U.S. Application of S. V. Tavtigian et al., filed Jul. 7, 1995, Ser. No. 08/499,787). This technique involves performing PCR with specific primers and a cDNA template, gel purification of the amplified fragment, solution hybrid capture of the gel purified DNA using MTS specific oligomers, and reamplification of the captured DNA using nested primers. Specifically, mouse RNA from breast and thymus was made into cDNA such that it was anchored at its 5' end with a unique sequence oligomer RP.2 (5'-TGAGTAGAATTCTAACGGCCGTCATTGTTC-3' SEQ ID NO:28). The cDNA was amplified with a reverse oligomer common to both MTS2 exon 2 and MTS1 exon 2, this being 5'-AGCGTGTCCAGGAAGCCTTC-3' (SEQ ID NO:29) and a nested version of RP.2 called RP.B, this sequence being 5'-TGAGTAGAATTCTAACGGCCGTCATTG-3' (SEQ ID NO:30). The resulting amplified products were gel purified and then captured by solution hybridization with the MTS1-specific biotinylated oligomer 5'-ACTGCGAGGACCCCACTACCTTCTCC-3' (SEQ ID NO:31) or with the MTS2-specific biotinylated oligomer 5'-AACTGCGCCGACCCTGCCACCCTTACC-3' (SEQ ID NO:39). After capture the products were amplified with a MTS1-specific reverse oligomer 5'-GAACGTTGCCCATCATCATC-3' (SEQ ID NO:32) or with a MTS2-specific reverse oligomer 5'-TGGGCGCTGCCCATCATCAT-3' (SEQ ID NO:40). The products were cloned and then sequenced on an ABI 373A using the PRISM Ready Dye-Deoxy Terminator Cycle Sequencing Kit (Applied Biosystems).

cDNA clones containing exon 3 of MTS1 were isolated by conventional 3' RACE techniques (Sambrook et al., 1989). The cDNA was synthesized such that it contained a unique sequence oligomer incorporated at its 3' end called XPCR (5'-GTAGTGCAAGGCTCGAGAAC-3', SEQ ID NO:41). The cDNA was amplified with the MTS1-specific forward oligomer mM1.1 (5'-GGGCTCGGCTGGATGTCC-3', SEQ ID NO:42) and a reverse oligomer complementary to the XPCR sequence. The products were diluted 100 fold and then amplified with the nested primer mM1.2 (5'-CAAGAGCGGGGACATCAA-3', SEQ ID NO:43) which is derived from sequence 33 base pairs 3' of mM1.1. The products were cloned and sequenced. The mouse MTS1 (mouse p16) and MTS2 (mouse p15) cDNA sequences are shown in FIGS. 18A and 18B and as SEQ ID NOs: 44 and 45 respectively. The mouse MTS1E1β sequence is shown in FIG. 14 and as SEQ ID NO:25. FIG. 19 shows the amino acid sequences of mouse MTS1 (p16) and mouse MTS2 (p15). Table 2A shows a pairwise comparison of homology between mouse and human exon 1s. Table 2B shows a comparison between the mouse and human exon 2s.

with biotin and made to be single-stranded. Hybrids between c5 and the cDNA were allowed to form and then the biotinylated cosmid was captured using streptavidin-coated magnetic particles. The selected cDNA was eluted from the cosmid, amplified by PCR, cloned and sequenced. The cDNA clones were similar to those isolated by library screening in that they contained E1β, E2 and E3. None of the clones contained the previously described exon 1 (see SEQ ID NO:3). The sequence for MTS1E1β cDNA is set forth in SEQ ID NO:13.

Structure of MTS1E1β

MTS1 and MTS1E1β are two forms of a single gene: the two forms both utilize exons 2 and 3 but have different first exons. MTS1 contains the α form (E1α) which encodes the first 43 amino acids of the p16 protein encoded by MTS1. MTS1E1β contains the β form (E1β) of exon 1. The exon structure of the p16 gene was determined by comparing the

TABLE 2A

| Human | | | Mouse | | | | |
|---|---|---|---|---|---|---|---|
| MTS1E1α | MTS1E1β | MTS2E1 | MTS1E1α | MTS1E1β | MTS2E1 | | |
| 1 | — | 0.59 | 0.72 | — | 0.60 | MTS1E1α | |
| | 1 | — | — | 0.61** | — | MTS1E1β | Human |
| | | 1 | 0.62* | — | 0.80 | MTS2E1 | |
| | | | 1 | — | 0.60 | MTS1E1α | |
| | | | | 1 | — | MTS1E1β | Mouse |
| | | | | | 1 | MTS2E1 | |

*alignment includes one 2 base pair gap 15 base pairs from mouse translational start.
**alignment includes four one base pair gaps.

TABLE 2B

| Human | | Mouse | | | |
|---|---|---|---|---|---|
| MTS2 E2 | MTS1 E2 | MTS2 E2 | MTS1 E2 | | |
| 1 | 0.92 | 0.84 | 0.73 | MTS2 E2 | Human |
| | 1 | 0.82 | 0.66 | MTS1 E2 | |
| | | 1 | 0.74 | MTS2 E2 | Mouse |
| | | | 1 | MTS1 E2 | |

The introns between exon 1 (E1) and exon 2 (E2) in the mouse genes were located at the same positions as in the human MTS1 and MTS2 genes. The E1–E2 intron sizes were determined to be 5.5 kilobases and 3.5 kilobases for mouse MTS1 and MTS2, respectively. By comparison, E1/E1α-E2 intron sizes are 3.0 kilobases for human MTS1 and 2.4 kilobases for human MTS2 (Stone et al., 1995a; Stone et al., 1995b).

EXAMPLE 8

Isolation and Structure of MTS1E1β

Isolation of MTS1E1β

Figure 13:
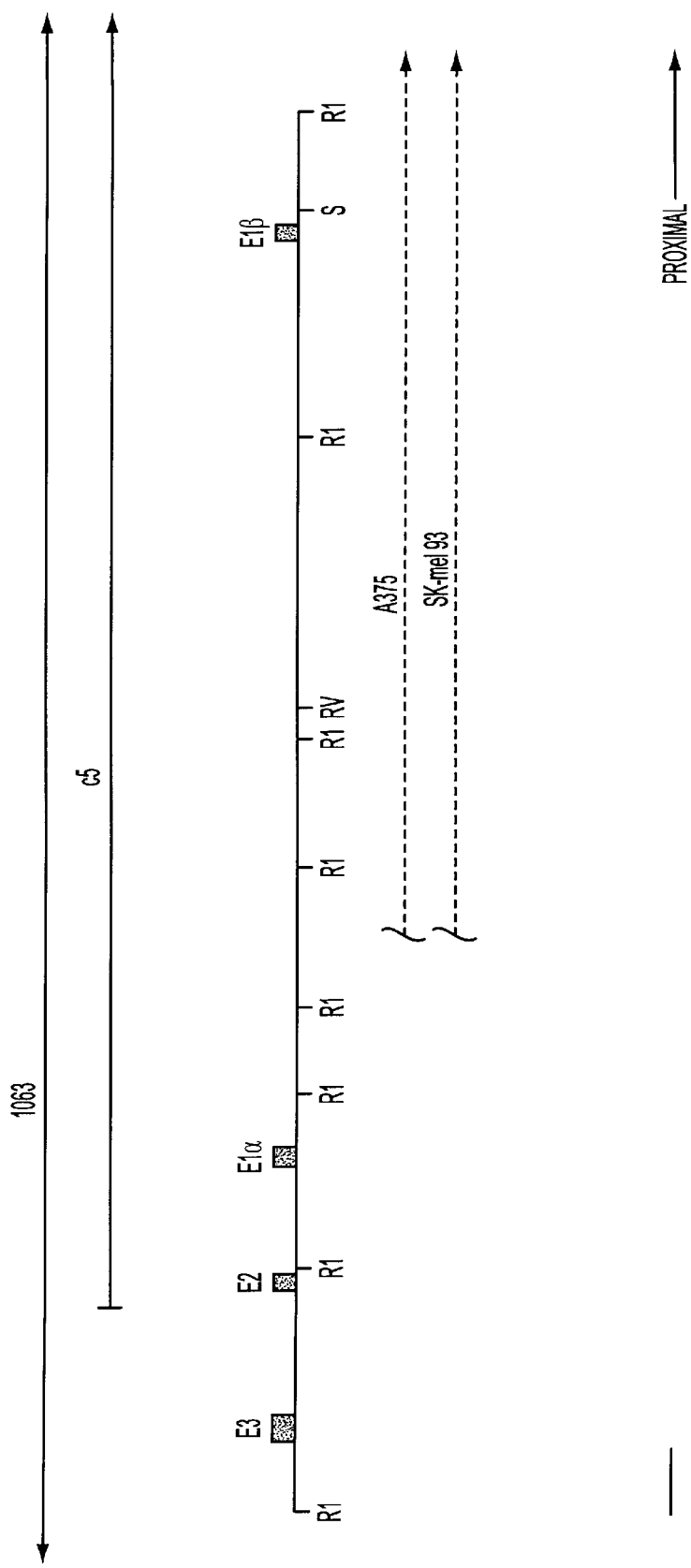
FIG. 13 is a physical map of the human P16 region. The positions of exon 1α (E1α), exon 1β (E1β), exon 2 (E2) and exon 3 (E3) are indicated by the filled boxes. The positions of restriction sites Eco R1 (R1), Eco RV (RV), and Sal I (S) are indicated. Above the restriction map are genomic clones cosmid c5 and P1 1063. Below the map are the deletions in cell lines A375 and SK-mel 93. The dashed line represents deleted DNA. The exact location of the distal breakpoint is not known in either A375 or SK-mel 93. However, these have been mapped to the interval between E1α and the STS c5.3 (Kamb et al., 1994b; Stone et al., unpublished).

Human clones that contained MTS1E1β were isolated by hybrid selection using the complete MTS1 cDNA as a probe and by conventional cDNA library screening. Conventional cDNA library screening was performed using a probe derived from exon 2 of MTS1. One million clones were screened from each of fetal brain, normal breast and lymphocyte-derived libraries. A hybridizing cDNA clone was isolated from the lymphocyte library. The clone was sequenced and shown to contain E1β. It also contained exon 2 (E2) and exon 3 (E3) of MTS1. Hybrid selection-derived cDNA clones were isolated by incubating cDNA derived from ovarian tissue with cosmid c5. The cosmid was labeled sequence of the composite cDNA clones to the genomic regions from which they were derived (FIG. 13). A combination of genomic Southerns, sequence analysis of the genomic region containing P16, and long PCR were used to map the positions of the P16 exons (FIG. 13). The p16 gene spans approximately 30 kb of genomic DNA. E1β is the most 5' of the exons, the order being E1β, E1α, E2 and E3.

Translation of E1β in the p16 reading frame (extrapolated from the reading frame used in p16 coding exons 2 and 3) revealed an in-frame stop codon positioned only 10 codons upstream of the splice junction between E1β and E2. The position of the stop codon was confirmed by genomic and cDNA sequence analysis. The first potential initiation codon, downstream of this stop was in the p16 reading frame, immediately 3' of the E1/E2 splice junction. This potential start codon is flanked by sequences that do not closely resemble the consensus Kozak sequence (Kozak, 1987). If translated in the p16 reading frame, the E1β transcript of the p16 gene would encode a protein of 105 amino acids.

Additional analysis of the β cDNA revealed that it possessed a large ORF in a different frame than the one used to encode p16. The ORF (referred to as ORF2) extended through E1β and continued for 67 amino acids into E2. The entire ORF could encode a protein of 180 amino acids. However, the reading frame remained open at the 5' end of E1β, and therefore, may be incomplete. Statistical analysis suggested that an ORF of this size was unlikely to occur by chance in DNA composed of random sequence (P=0.003). However, given the base composition of the β transcript, the probability was higher (P=0.16). The predicted polypeptide was not similar to any previously described protein.

Identifying the evolutionarily conserved portions of E1β might provide clues as to what sequences are important for its function. Mouse p16 cDNAs were isolated by a modified RACE technique called Hybrid Capture RACE (HCR) (see Examples 7 and 13) and compared to the human p16 cDNAs. One type of mouse P16 cDNA (the β type) possessed an exon equivalent to human E1β and an E2 equivalent. A second type (the α type) contained an E1α equivalent joined to E2. The E1α and E2 mouse exons were 70% identical to their human counterparts. The nucleotide sequence of the mouse and human E1β exons were 51% identical (FIG. 14) and the mouse E1β exon also contained stop codons in the reading frame used to encode p16. The human and mouse polypeptides, deduced from the nucleotide sequence 5' of the stop codon, were completely divergent. Therefore, it is unlikely that the stop codons in the p16 reading frame were sequencing artifacts.

Given the uncertainty regarding the role of E1β, we analyzed the similarity between the mouse and human β transcripts in all three reading frames. The mouse and human β transcripts contained a large ORF (ORF 2) in a different reading frame than the one used to encode p16 (ORF 1). The deduced polypeptides encoded by ORF 2 were 40% identical. However, they were only 28% identical if we restricted the comparison of the ORF 2 peptides to the portion encoded by E1β. In contrast, the mouse and human p16 sequences were 67% identical. In addition, the polypeptides deduced from ORF 2 contained in E2 were as similar (42%) as the polypeptides deduced from the third reading frame in E2 (ORF 3). These results suggest that ORF 2 has not been selectively maintained and probably does not encode a protein. The secondary structure of the human and mouse β RNAs were also compared. No striking similarities were identified. Collectively, these results suggest that the β transcript is required for P16 function by virtue of its presence in both mouse and man; and that if it is translated, the encoded protein probably initiates at the first methionine in exon 2.

EXAMPLE 9

Germline Mutations in MTS1

To test whether or not MTS1 or MTS2 corresponded to the genetic susceptibility locus MTS, genomic DNA was analyzed from eight individuals presumed to carry MTS predisposing alleles (Cannon-Albright et al., 1992). DNA sequences from the exons were amplified from each sample using oligonucleotide primers (Table 3) derived from intron sequences specific for either MTS1 or MTS2.

TABLE 3

Primers for Screening Exons in MTS1

| Primers | SEQ ID NO: | Exon | Gene |
|---------|------------|------|------|
| 1F      | 6          | 1    | MTS1 |
| 1108R   | 7          | 1    | MTS1 |
| 42F     | 8          | 2    | MTS1 |
| 551R    | 9          | 2    | MTS1 |
| 21F     | 10         | 2    | MTS2 |
| 50R     | 11         | 2    | MTS2 |
| 89F     | 12         | 2    | MTS2 |

Exon 1 of MTS1 was amplified using primers 1F and 1108R and then sequenced using primer 1108R. Exon 2 of MTS1 was amplified using primers 42F and 551R and then sequenced using primers 42F and 551R. Exon 2 of MTS2 was amplified using primers 21F and 50R, reamplified using primers 89F and 50R and then sequenced using primers 89F and 50R.

The DNA sequences of these genomic fragments revealed polymorphisms in two of the eight individuals. The polymorphisms were not present in any of the other samples, suggesting that they were not common in the population. To demonstrate that the polymorphisms were linked to the MTS chromosome and not to the other homolog, genomic DNA from other individuals who carry the predisposing allele from each kindred were analyzed. In each case, the polymorphisms segregated with the MTS predisposing allele. The mutation at codon 93 (gly→trp) was found in an individual (12821) in kindred 3012. It was also found in affected carrier sib (13183) and in unaffected carrier cousin (14917), but not in unaffected non-carrier sib (13184). The mutation at codon 118 (val→asp) was found in an individual (15635) in kindred 1771. It was also found in affected carrier first cousin once removed (10205), affected carrier first cousin (11414) and in affected carrier first cousin of 10205 (10146), but not in unaffected non-carrier uncle of 10205 (10120).

The polymorphisms were single nucleotide substitutions that caused amino acid changes (Table 4). The substitutions involved either the substitution of a large hydrophobic residue for small hydrophilic residue, or the substitution of a charged amino acid for a neutral amino acid.

TABLE 4

Predisposing Germline MTS Mutation

| Mutation | Coding Effect | Location* |
|----------|---------------|-----------|
| G→T      | gly→trp       | 277       |
| T→A      | val→asp       | 353       |

*Location of mutation in DNA sequence of SEQ ID NO: 1.

Exon 2 from MTS2 showed no polymorphisms in the eight samples tested. This suggests that, at least in this set of kindreds, MTS2 does not predispose to melanoma. It is possible that MTS2 is involved in other types of cancer based on its similarity to MTS1. It is also possible that MTS2 is a nonfunctional gene.

The finding of germline mutations in MTS1 and not in MTS2 in individuals predisposed to melanoma is consistent with the analysis of melanoma homozygous deletions.

EXAMPLE 10

Analysis of the Presence of MTS in Tumor Lines

Figure 4B:
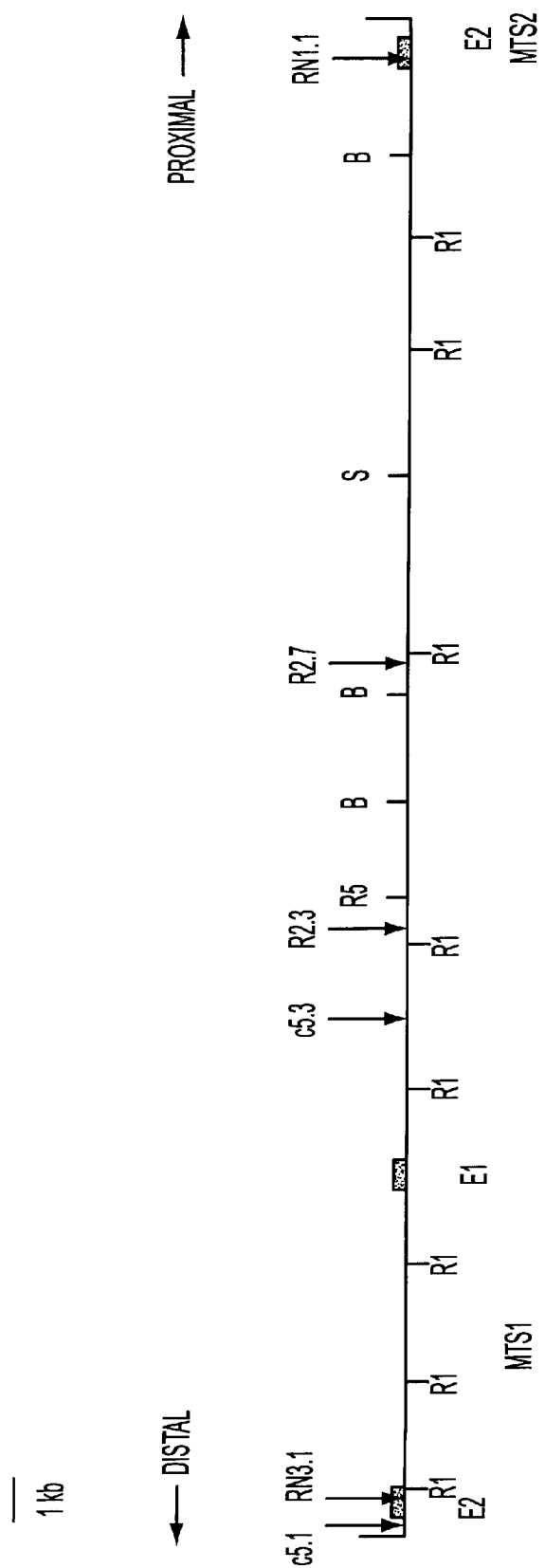
FIG. 4B shows a restriction map and STS map of cosmid c5. Positions of coding exons for MTS1 and MTS2 are shown as thick bars. "E1" and "E2" mean "coding exon 1" and "coding exon 2," respectively. "B" is BamHI, "S" is SalI, "R1" is EcoRI and "R5" is EcoRV.

Because of the high frequency of deletions at 9p21 in multiple tumor types, cell lines derived from 12 different types of tumor were analyzed for the presence or absence of MTS1. A set of sequence-tagged sites (STSs) spaced across the gene was used to test genomic DNA from tumor cell lines for the presence or absence of the expected fragment (FIGS. 4A, 4B and 9). The results of this study suggested that MTS1 was deleted from a large percentage of tumor lines (Table 5). Homozygous deletions occurred in all tumor types tested other than colon and neuroblastoma cell lines, the percentage of deletions varied from a low of 25% in lung cancer and leukemia to 94% in astrocytomas. In total, homozygous deletions were detected in 135 of 290 cell lines tested. This number yields a minimum estimate of the percentage of tumor lines that harbor deletions because the STSs used for the analysis did not cover the entire gene. Thus, certain small deletions could have escaped detection. In addition, lesions such as insertions or deletions of a few nucleotides, and nucleotide substitutions, would be missed by this approach.

TABLE 5

Homozygous Deletions in Tumor By Tumor Type

| Tumor Type | No. Lines | No. Deletions | % Deletions |
|---|---|---|---|
| melanoma | 99 | 57 | 58 |
| leukemia | 4 | 1 | 25 |
| lung | 59 | 15 | 25 |
| neuroblastoma | 10 | 0 | 0 |
| bladder | 15 | 5 | 33 |
| renal | 9 | 5 | 56 |
| astrocytoma | 17 | 16 | 94 |
| colon | 20 | 0 | 0 |
| breast | 10 | 6 | 60 |
| ovary | 7 | 2 | 29 |
| glioma | 35 | 25 | 71 |
| osteosarcoma | 5 | 3 | 60 |
| TOTAL | 290 | 135 | 47% |

To improve the estimate of the total number of cell lines containing MTS1 mutations, 34 of the cell lines that did not suffer obvious homozygous deletions of MTS1 sequence were examined more closely for lesions in MTS1. Sequences comprising nearly 97% of the MTS1 coding sequence were amplified and screened for polymorphisms. Eighteen somatic mutations in exon 2 or exon 1 of MTS1, distributed in 14 out of 34 melanomas, were observed (Table 6). Three of these mutations were frameshifts, 7 were nonsense mutations, 4 were missense mutations and 4 were silent. Three of the 4 lines that contained silent mutations also contained additional mutations and 16 of 18 mutations were located in coding exon 2. All but one line contained exclusively hemi- or homozygous polymorphisms, suggesting that the other homologous chromosomes had incurred deletions. The single line that was heterozygous contained two different nonsilent mutations, a finding consistent with the view that each homolog had undergone independent mutational events. Based on this DNA sequence and deletion analysis of MTS1, a minimum of 75% of melanoma lines contained mutant MTS1 or had lost the gene from both homologs.

TABLE 6

Somatic MTS Mutations in Tumors

| Cell Line | Mutation | Coding Effect | Location* |
|---|---|---|---|
| SK-M-ste | G→A | none | 240 |
|  | G→A | gly→ser | 241 |
| SK-M-swi | C→T | arg→stop | 148 |
| SK-M-ris | G→A | ala→thr | 418 |
| SK-M-beh | 5 base deletion | frameshift | 266–270 |
| SK-M-178 | C→T | arg→stop | 214 |
| SK-M-sta | G→A | trp→stop | 306 |
| SK-M-uti | C→T | arg→stop | 214 |
| SK-M-EML131 | 8 base deletion | frameshift | 148–155 |
|  | C→A | none | 147 |
| SK-M-koz (het.**) | C→T | pro→leu | 317 |
|  | C→T | none | 213 |
|  | C→T | arg→stop | 214 |
| SK-M-kra | C→T | pro→leu | 317 |
| SK-M-kuu | C→T | none | 354 |
| SK-M-mar | G→A | trp→stop | 305 |
| SK-M-whi | C→T | gln→stop | 124 |
| SK-M-adl (het.) | 2 base deletion | frameshift | 104–105 |

*Location of mutation in DNA sequence of SEQ ID NO: 1.
**Het. stands for "heterozygote" and refers to the presence in the sample of both wildtype and mutant sequences.

The preponderance of lesions in MTS1 (deletions and nucleotide substitutions) indicates that MTS1 or a closely linked locus contributes to the tumor phenotype. Cells that suffer these lesions enjoy a selective advantage over cells that do not. The alternative explanation, that the lesions are random events that have nothing to do with cell growth, is unlikely for several reasons. First, the high correlation between tumor phenotype and mutation at MTS1 implies a causal relation between MTS1 mutations and tumor formation. Second, MTS1 influences susceptibility to melanoma, and thus is implicated independently as a tumor suppressor gene. Third, the biochemical function of p16 as a potent inhibitor of a Cdk neatly fits a model where p16 acts in vivo as a general inhibitor of the onset of DNA replication.

It is possible that mutation or loss of MTS1 is a product of cell growth in culture. However, a high percentage of primary leukemia cells also contain homozygous deletions of the α-interferon gene cluster, a gene family located less than 500 kb from MTS1 (Diaz et al., 1990). Previous deletion studies suggest that deletions of cc-interferon genes invariably involve markers that extend beyond MTS1 toward the centromere (Weaver-Feldhaus et al., 1994). Because homozygous deletions of the MTS1 region occur in primary tumor cells as well as cultured cell lines, the deletions observed in tumor cell lines are unlikely to be purely an artifact of cell growth in culture. Nevertheless, the question of when MTS1 mutations occur during the progression of tumors will be answered best by analysis of primary tumor samples.

The role of MTS1 in vivo

In all eukaryotic cells, cell division requires passage through two critical decision points: the G1 to S transition, where DNA synthesis commences, and the G2 to M transition, where mitosis begins. In mammals, the machinery that controls cell division has multiple components, many of which are related (for review see Sherr, 1993). The Cdks may be at the heart of the control apparatus, in that they regulate by phosphorylation a number of key substrates that in turn trigger the transition from G1 to S and from G2 to M. The G1 to S transition is perhaps the more critical decision point, as it occurs first in the cell cycle. So far, four types of Cdk have been defined (Cdk2–5) that may participate in G1 to S control, as well as a set of positive regulators of these Cdks (cyclins C, D1–3, E). Recently several negative regulators have also been identified, including p16, p15, p18, p20, p21, and p27 (Xiong et al., 1993; Serrano et al., 1993; Gu et al., 1993; El-Diery et al., 1993; Harper et al., 1993; Hannon and Beach, 1994; Polyak et al., 1994b; Toyoshima and Hunter, 1994; Guan et al., 1995). These negative regulators appear to act by inhibiting the kinase activity of the Cdks. Some of the cell cycle regulators are involved in human cancers (for review, see Hunter and Pines, 1994). p20 inhibits Cdk2 and possibly other Cdks while p16 (also called MTS1, CDKN2, or INK4a) inhibits Cdk4 but apparently does not inhibit Cdk2 in an in vitro assay (Serrano et al., 1993). Based on in vitro studies and on its interaction with p53, p21 has been proposed as a general inhibitor of all Cdks (Xiong et al., 1993). Thus, in vitro, p16 appears more specific than p21. Each of these inhibitors is expected to antagonize entry into S phase. Also, cyclin D1 or Cdk4 is overexpressed in some breast carcinomas and the p16 gene is mutated or deleted in a large number of cell lines and primary tumors (Buckley et al., 1993; Caldas et al., 1994; Kamb et al., 1994b; Mori et al., 1994; Tam et al., 1994a). These results suggest that certain cyclins and Cdks are protooncogenes and that P16 (MTS1) is a tumor suppressor gene. The biochemical behavior of p15, p18, p21 and p27 indicate that they too may be tumor suppressors, but detailed mutational analysis of their genes in tumors or cell lines has not been reported. The results presented here provide evidence that MTS1 functions in vivo as an inhibitor of cell division.

The p16 gene (MTS1), located in the 9p21 segment of human chromosome 9, is especially interesting because it is mutated or homozygously deleted in a high percentage of some types of tumors and tumor-derived cell lines (Caldas et al., 1994; Kamb et al., 1994b; Mori et al., 1994; Nobori et al., 1994). In addition, MTS1 mutations segregate with predisposition to melanoma in several kindreds known to carry 9p21 linked melanoma susceptibility (Hussussian et al., 1994; Kamb et al., 1994a). However, there are unresolved questions regarding the role of MTS1 in hereditary and sporadic cancer. Several melanoma-prone kindreds with high LOD scores for 9p21 markers do not reveal mutations in MTS1 coding sequences. Also, the preponderance of MTS1 homozygous deletions in tumors and cell lines is atypical for tumor suppressor gene inactivation and may imply the presence of another gene(s) near MTS1 which also participates in cancer formation.

Recent reports suggest that some mitogenic and antimitogenic signals affect cell cycle progression, at least in part by regulating the activity of CDK inhibitors (Firpo et al., 1994; Hannon and Beach, 1994; Kato et al., 1994; Polyak et al., 1994a; Slingerland et al., 1994). For example, TGFβ-induced cell cycle arrest may be mediated by activation of p15 and p27. Conversely, p27 may be negatively regulated during IL-2-induced mitogenic activation of quiescent T lymphocytes. Comparatively little is known about the regulation of MTS1. Many recent reports provide evidence that MTS1 levels may be regulated in part by Rb protein (Serrano et al., 1993; Li et al., 1994a; Tam et al., 1994b; Parry et al., 1995). These and other findings (Serrano et al., 1995) have contributed to a model for MTS1 action in which MTS1 inhibits CDK4/6 and thereby prevents phosphorylation of Rb. Rb in turn participates in a feedback loop to limit the levels of MTS1.

These results provide genetic evidence for a pre-eminent role of MTS1 in control of the cell cycle. Moreover, the results suggest that the target of MTS1 in vivo is a major factor in tumorigenesis. If MTS1 inhibits Cdk4 in vivo and not Cdk2, Cdk4 may be a strong candidate for an oncogene. The prevalence of mutations in the MTS1 gene implies that Cdk4 may serve as a general activator of cell division in most, if not all, cells. Further biochemical studies of the effects of MTS1 on different Cdks may help clarify the hierarchy of Cdk activity in both normal cells and transformed cells. By analogy with p16, if p21 acts as a general inhibitor of Cdks, its gene may also be lost or mutated in a large percentage of tumors.

If MTS1 is a general tumor suppressor active in most normal cells, germline mutations in MTS1 might be expected to predispose to cancers other than melanoma For example, germline mutations in the p53 gene such as those found in Li-Fraumeni syndrome increase the likelihood of many tumor types including childhood sarcomas, breast cancer (Malkin et al., 1990). Previous studies have found an unusually high incidence of pancreatic cancer in some families that are prone to melanoma (Bergman et al., 1990; Nancarrow et al., 1993). This observation accords with the finding that homozygous deletions of MTS1 occur in pancreatic tumor lines. It is possible that the genetics of MTS1 predisposition may be different from the somatic cell genetics of MTS1. For instance, large deletions that remove many kilobases of DNA from the region surrounding MTS1 may be lost from the human gene pool, due to a selective disadvantage. However, such deletions may be favored in transformed somatic cells, perhaps because they remove multiple genes. This possibility is consistent with the existence of a second gene with striking similarity to MTS1, called MTS2. MTS2 is located roughly 12 kb upstream of exon 1 of MTS1, the first exon of MTS2 being roughly 2.5 kb upstream of the second exon of MTS2. MTS2 may function in a fashion similar to MTS1. Deletions that remove both MTS1 and MTS2 might confer a greater growth advantage to cells than mutations that inactivate either gene alone. Alternatively, the two different genes may function in a non-overlapping or partly overlapping set of cell types. These possibilities remain to be thoroughly explored.

EXAMPLE 11

Mutational Analysis of MTS1E1β

Both the preponderance of homozygous deletions which inactivate P16 in tumor derived cell lines, and the 9p21-linked melanoma-prone kindreds that do not reveal mutations in P16 have led others to propose the presence of another gene(s) near P16 which is also involved in cancer formation (Cairns et al., 1994; Spruck et al., 1994). If E1β encoded a protein which was involved in regulating cell growth, then these sequences could contain mutations in either sporadic and/or familial cancer that would have been missed in earlier studies. Therefore, E1β was screened for mutations in cell lines derived from various tumors and in some melanoma prone kindreds.

Genetic characterization of the melanoma-prone pedigrees has been previously reported (Cannon-Albright et al., 1992). Isolation of genomic DNA from melanoma prone kindreds (Kamb et al., 1994a) and from cell lines (Liu et al., 1995) has been previously described. PCR amplification for E1β was performed using the forward primer (5'-AGTCTGCAGTTAAGG-3' SEQ ID NO:33) and the reverse primer (5'-GGCTAGAGGCGAATTATCTGT-3' SEQ ID NO:34) for 30 cycles using the following conditions: 97° C. for 3 seconds, 65° C. for 10 seconds, 75° C. for 20 seconds. The amplification reactions were diluted 100 fold and amplified again under the same reaction conditions with the same forward primer and the reverse primer (5'-CACCAAACAAAACAAGTGCCG-3' SEQ ID NO:35). PCR products were run on a 1% agarose gel and were extracted using Qiagen beads (Qiagen, Inc.). The products were sequenced using the Cyclist Sequencing kit (Stratagene) with the forward primer mentioned above (SEQ ID NO:33).

No sequence variants of E1β were detected in a set of 24 cell lines derived from 4 tumor types (Table 7) or in 6 melanoma kindreds with significant haplotype sharing among affected family members (Cannon-Albright et al., 1992), but which did not reveal P16 mutations in a previous study (Kamb et al., 1994a). These experiments suggest that mutations in E1β are not a common event during tumor progression, nor are they responsible for 9p21 linked melanoma susceptibility in these kindreds.

TABLE 7

Cell Lines Screened for E1β Mutations

| Type | Number |
|---|---|
| lung | 3 |
| bladder | 7 |
| glioma | 9 |
| melanoma | 5 |
| total[1] | 24 |

[1]These cell lines were previously shown not to contain homozygous deletions in the P16 region or harbor P16 coding sequence mutations (Liu et al., 1995). Based on previous results (Liu et al., 1995), a similar number and type of cell lines would have contained 4 point mutations in the p16 coding sequence, confined to the bladder and melanoma groups.

EXAMPLE 12

Mutation Screening of MTS2

MTS2 mutation screening in cell lines

The preponderance of homozygous deletions that remove MTS1 in tumor derived cell lines may suggest the presence of another gene or genes near MTS1 which are also involved in cancer formation. If the MTS2 gene were involved in sporadic cancer, it might contain mutations in cell lines of tumor origin. Therefore, MTS2 coding sequences were screened for mutations in a set of tumor cell lines.

PCR amplification for exons 1 and 2 of MTS2 were performed as described in Kamb et al. (1994a). The primer pair 2E1.F1 (5'-AGGGAAGAGTGTCGTTAAG-3' SEQ ID NO:19) and 2E1.R2 (5'-AGACTCCTGTACAAATCTAC-3' SEQ ID NO:20) was used to obtain exon 1. Primer pair 89F (SEQ ID NO:12) and 50R (SEQ ID NO:11) was used to obtain exon 2. After amplification, the DNA products were run on a 1% agarose gel and were extracted using Qiagen beads (Qiagen, Inc.). The products were sequenced using the Cyclist Sequencing kit (Stratagene) with primer 2E1.F1 for exon 1 and 89F and 5OR for exon 2.

MTS2 coding sequences were screened for mutations in a set of cell lines derived from bladder, glioma, astrocytoma, lung, renal, and melanoma tumors. All these cell line types contain homozygous deletions of MTS2 and MTS1 at high frequencies (Kamb et al., 1994b). Cell lines derived from melanoma, lung, renal, and bladder carcinoma have been shown to contain point or frameshift mutations in MTS1 (Liu et al., 1995). Glioma and astrocytoma cell lines, however, have not been shown to contain such MTS2 mutations. The particular cell lines used in these screening experiments were selected from a group shown previously not to harbor homozygous deletions of MTS2 and MTS1 sequences (Kamb et al., 1994b).

No MTS2 mutations were found in MTS2 coding sequences in any of the 58 cell lines that were screened (see Table 8). Based on previous studies of MTS1 in these cell line types, the set would be expected to contain about 8 MTS1 mutations confined to the bladder, melanoma, lung, and renal group (Liu et al., 1995). Thus, no evidence for somatic mutations in MTS2 was obtained from this set of tumor cell lines.

TABLE 8

Mutation Screening of MTS2 in Cell Lines

| | | | Polymorphisms[1] | |
|---|---|---|---|---|
| Cell Line Type | # Screened | # of Changes | Types of Change | Coding Effect |
| Astrocytoma | 2 | 0 | | |
| Bladder | 4 | 1 | G → A; C → A | None |
| Glioma | 6 | 0 | | |
| Melanoma | 17 | 2 | G → A: C → A | None |
| Renal | 4 | 1 | G → A; C → A | None |
| Lung | 10 | 1 | G → A; C → A | None |
| Small Cell Lung | 7 | 2 | G → A; C → A | None |
| Non-small Cell Lung | 8 | 0 | | |
| Total | 58 | 7 | | |

[1]These common polymorphisms (Kamb et al., 1994a) are located in intron 1 near the 3' acceptor site at nucleotide positions −27 (C to A) and −103 (G to A).

MTS2 mutation screening in kindreds

The possibility that the MTS2 gene accounts for the melanoma susceptibility in the 9p21-linked, melanoma-prone kindreds that do not have MTS1 coding sequence mutations is attractive. Genetic characterization of the melanoma-prone pedigrees has been previously reported (Cannon-Albright et al., 1992). Genomic DNA from family members was isolated from lymphocytes which had been separated from whole blood using standard procedures (Kamb et al., 1994a). Screening was performed as described above for mutations in MTS2 coding sequences in 6 kindreds with high LOD scores for 9p2-linked predisposition to melanoma but which did not reveal MTS1 mutations in a previous study (see Table 9) (Kamb et al., 1994a). No mutations in MTS2 were detected. These experiments thus provide no evidence that MTS2 lesions contribute to hereditary melanoma although such a possibility cannot be ruled out simply based on these limited experiments.

TABLE 9

Melanoma-prone Kindreds Screened for MTS2 germline Mutations

| Kindred | LOD Score | Total Cases | Cases with Haplotype |
|---|---|---|---|
| 3346 | 5.97 | 21 | 21 |
| 3137 | 1.9 | 17 | 21 |
| 1764 | 1.04 | 4 | 4 |
| 3006 | 0.19 | 6 | 3 |
| 3161 | −0.01 | 10 | 8 |
| 3343 | −0.53 | 10 | 8 |

EXAMPLE 13

Expression of MTS1 and MTS1E1β RNAs

Two P16 promoters

The two different forms of the P16 mRNA could be generated in two possible ways. Transcription could initiate from different promoters, or the mRNA could be derived from a single promoter and then alternatively spliced to generate the different forms of the transcript.

Figure 15:
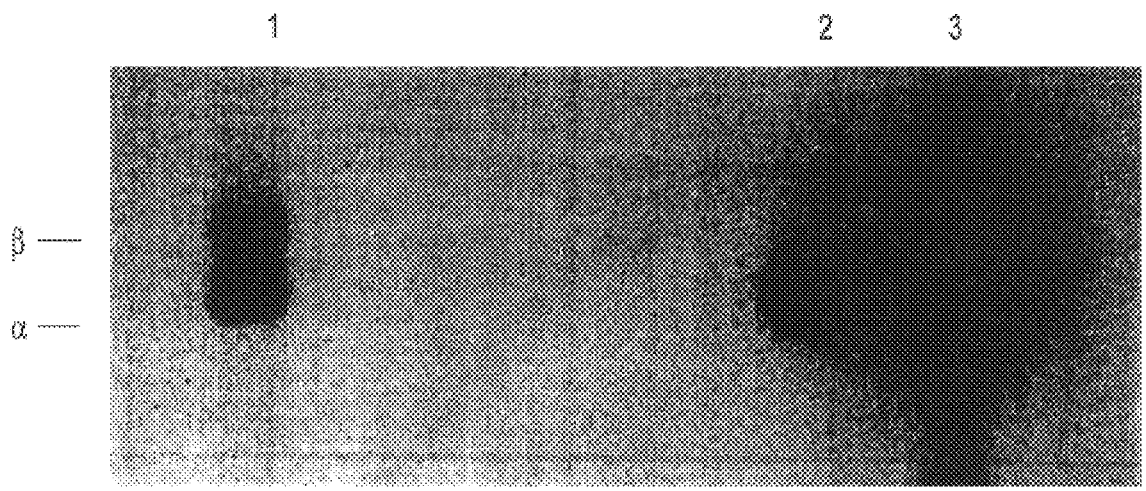
FIG. 15 shows the expression of the α transcript in cell lines that contain deletions of E1β. cDNA was derived from total RNA isolated from the indicated samples. A radio-labeled primer was included in the reactions to amplify the P16 transcripts. Equal volumes of the α and β amplifications were mixed, and the products were resolved on a denaturing 5% polyacrylamide gel: lane 1—quiescent T cells; lane 2—cell line SK-mel 93; lane 3—cell line A375.

Evidence for separate α transcript and β transcript promoters was obtained by demonstrating that the α form was transcribed in cell lines even when the upstream E1β sequences were deleted. Cell lines A375 and SK-mel 93 contain a deletion with one breakpoint between E1α and E1β (FIG. 13). The proximal breakpoint has not been precisely mapped in either cell line, but was at least 85 kb upstream of the 5' end of E1β. Using RT-PCR with α-specific primers, both of these cell lines were shown to express the α transcript (FIG. 15). The procedure for the RT-PCR is as follows: cDNA was synthesized from total RNA (Sambrook et al., 1989) isolated from T cells, cell lines, or human tissues (Clontech). The cDNA reactions employed random 9 mers to prime DNA synthesis and Superscript II reverse transcriptase (Bethesda Research Laboratories). cDNA yields were calculated by including $\alpha^{32}$P-dATP (Amersham) in the synthesis reaction (0.1 Ci/mmole) and determining the amount of radioactive nucleotide incorporated into the final product. P16α and P16β transcript levels were analyzed by PCR using α or β specific forward primers and heminested reverse primers from E2 in two successive rounds of amplification. In the initial amplification, 2 ng of cDNA was amplified with the α-specific primer AS.1 (5'-CAACGCACCGAATAGTTACG-3' SEQ ID NO:26) or the β-specific primer BS.1 (5'-TACTGAGGAGCCAGCGTCTA-3' SEQ ID NO:27) and X2.R140' (5'-AGCACCACCAGCGTGTC-3' SEQ ID NO:22). The reactions were done on a Perkin-Elmer 9600 thermal cycler for 20 cycles under the following conditions: 97° C. for 3 seconds; 65° C. for 10 seconds; 75° C. for 20 seconds. These reactions were diluted 100 fold and reamplified with AS.1 or BS.1 and X2B (5'-CGTGTCCAGGAAGCCC-3' SEQ ID NO:23). The X2B oligo was radiolabeled at its 5' end (Sambrook et al., 1989) with $\gamma^{32}$P-dATP (DuPont). PCR conditions were as above, but for only 15 cycles. To eliminate problems due to genomic DNA contamination, the PCR products spanned the E1α or E1β/E2 splice junction. The products were resolved by electrophoresis through a denaturing 5% polyacrylamide gel. Dried gels were exposed to X-OMAT (Kodak) film overnight.

The results suggest that the α transcript initiates from a promoter that is independent of sequences 5' of E1β. An alternative explanation is that the deletions fused ectopic promoter sequences to E1α. However, this seems unlikely given that A375 and SK-mel 93 are independently isolated cell lines. The exact location of the α promoter is not clear, but RNase protection analysis indicated that it initiated at least 440 bp upstream of the p16 initiation codon. Thus, the human p16 gene is complex, with two partially overlapping transcripts with distinct coding potential, produced from separate promoters, $P_\alpha$ and $P_\beta$.

Expression pattern of P16

Clues to the function of genes may emerge from analysis of their expression pattern in different tissues. To determine the expression pattern of P16, a set of cDNA samples prepared from eleven tissues were screened by PCR with α and β specific primers (FIGS. 16A–D). Both forms of P16 transcript were detected in all tissues examined, though there were some differences. For example, in spleen the ratio between the α and β forms was skewed toward β. In contrast, the ratio in breast favored α. These expression data are consistent with studies which found deletions and point mutations of P16 in cell lines derived from many different tissue types (Kamb et al., 1994b; Liu et al., 1995) in that they suggest roles for p16 in multiple tissues.

Given the biochemical function of p16, demonstrated in vitro to be an inhibitor of CDK4 and CDK6 (Serrano et al., 1993; Li et al., 1994a; Parry et al., 1995), the expression of P16 was analyzed as cells traversed the cell cycle. Human peripheral blood lymphocytes (PBLs) were stimulated by phytohemaglutinin (PHA) plus interleukin-2 (IL-2), and cells were harvested at different times after stimulation. These cells were analyzed by flow cytometry to determine their cell cycle stage, by RT-PCR to determine the relative levels of P16 gene expression, and by Western blot to determine the levels of p16 protein. The peripheral blood lymphocytes were isolated from blood drawn from normal adult donors and partially purified by floatation on Ficoll-Hypaque gradients (Boyum, 1968). The lymphocytes were further purified by counter current elutration as peviously described (Elstad et al., 1988). These authors estimated that a cell population, prepared in this manner, was 98% pure B and T cells. The purified cells were grown in RPMI (Gibco) supplemented with 10% fetal bovine serum. Quiescent cells were induced by 10 µg/ml PHA (Sigma) and 10 U/ml IL-2 (Sigma). Cell cycle progression was monitored by flow cytometry. RNA was isolated from primary T cells using RNazol B (CINNA/BIOTECX Laboratories, Inc.) as described by the manufacturer. The quantitative behavior of the RT-PCR was confirmed by creating serial dilutions from the T cell cDNA isolated after induction. The amount of target cDNA present in the undiluted sample was quantified by determining the dilution value at which the target was no longer amplifiable. Although the results from the different PCR experiments were in agreement, the dilution experiments suggested that we could only detect changes in RNA levels if they were greater than 4 fold. The cDNA samples from the Rb⁺ and Rb⁻ cell lines were also analyzed in this manner. Human actin was easily detected and present in similar amounts from each cDNA sample (whether from tissues, cell lines, or T cells).

Figure 16A:
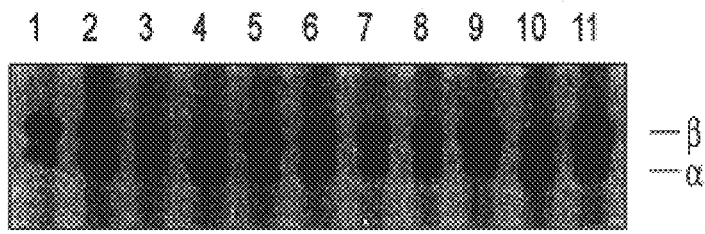
FIGS. 16A–D show the expression of human P16 transcripts. A radio-labeled primer was included in the reactions to amplify the P16 transcripts and the products were resolved on a denaturing 5% polyacrylamide gel.
Figure 16B:
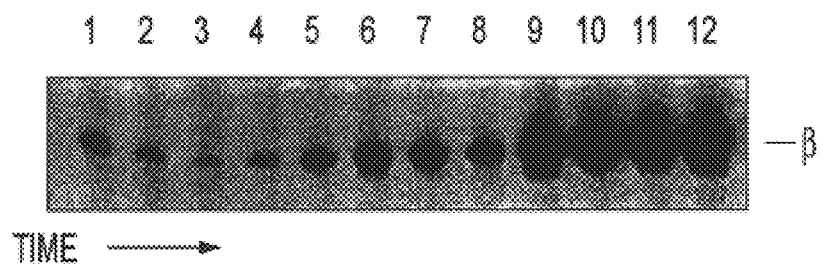
Figure 16C:
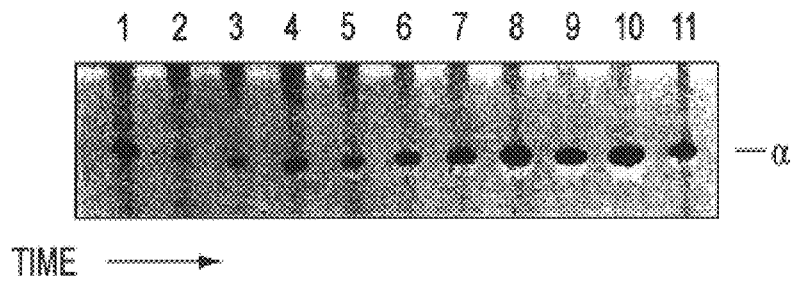
Figure 16D:
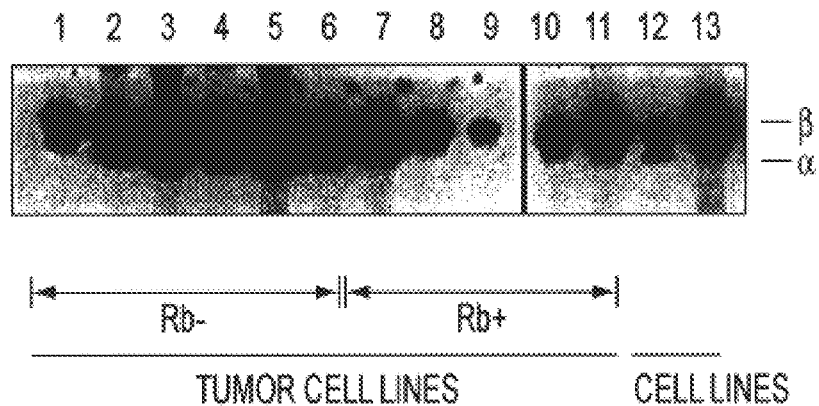

The ratio of the two forms of P16 transcript changed dramatically through the cell cycle (FIGS. 16B–C). Initially, the β form was low, but by 30 to 40 hours after stimulation, the level began to rise. During this time, the expression level of the α form remained relatively constant, perhaps increasing slightly. By flow cytometry, the ratio change was correlated with cells exiting $G_o$ and entering S phase. The quantitative behavior of the RT-PCR was examined by template dilution experiments. Based on those experiments, RT-PCR was sensitive to four fold or greater changes in transcript level. The β induction was estimated to be at least ten fold. Therefore, as T-cells entered the cell cycle they altered the relative amounts of the two forms of the P16 transcript so that the ratio changed in the favor of β.

We also examined the level of p16 protein expression as the T-cells traversed the cell cycle. Protein was isolated from the cells at various times after mitogenic induction, and the isolated protein was subjected to Western analysis. The levels of p16 protein were determined using a p16 antibody raised against the 20 C-terminal amino- acids of the complete polypeptide. As the cells exited Go, the level of p16 protein remained relatively constant Thus, both the p16-encoding RNA (the α transcript) and p16 protein remained relatively constant during the cell cycle. Others have reported a moderate increase in p16 levels during S phase (Tam et al., 1994b). We did not see an accumulation of p16, which might reflect differences in p16 regulation in different cell types, or reflect problems in detecting a two to three fold increase in protein (or cDNA) levels.

Expression of P16 in tumor cell lines

Previous studies have suggested that Rb influences the expression of p16 (Serrano et al., 1993; Li et al., 1994a; Parry et al., 1995). We tested the effect of the Rb status of cells on the expression of the β mRNA (FIG. 16D). cDNA was prepared from a set of cell lines, five of which contained wild type Rb protein, and six of which contained non-functional Rb protein (Parry et al., 1995). As expected, α transcript was only detected in Rb-negative lines. However, the β transcript was present in both Rb-positive and Rb-negative cell lines. Therefore, in contrast to α, expression of the β RNA is independent of the mutation state of Rb in tumor-derived cell lines.

There is evidence that p16 is a member of a multigene family (Guan et al., 1995). By analogy with other multigene families, the members of this family might carry out redundant functions, different functions, or function in different temporal or tissue-specific patterns. Therefore, given the low level of p16 protein and apparent lack of P16 regulation by Rb, it is possible that P16 does not regulate the cell cycle in T lymphocytes. However, because the β transcript was dramatically induced upon T cell induction, and because P16 is deleted in a high percentage of T cell-derived tumors (Hebert et al., 1994), it seems likely that p16 carries out an important function in human T cells. A dramatic effect of Rb on p16 has only been observed in virally transformed or tumor-derived cell lines. Perhaps P16 is regulated in some other manner in wild type tissue.

E1β is a conserved and regulated part of p16

Although the role of the β transcript is unclear, the results suggest that it is important for the function of the p16 locus because: (i) E1β is conserved in mice; (ii) the relative amount of the β transcript is regulated in both a tissue-specific and cell-cycle dependent manner; and (iii) two cell lines harbor homozygous deletions that remove E1β, but not E1α. These results suggest that E1β is required for wild-type P16 function.

The mouse β cDNA was isolated and compared to MTS1E1β of humans. Mouse cDNA clones were isolated by a modified hybrid selection procedure called hybrid capture RACE (HCR). Mouse polyA+-enriched RNA was isolated from breast and thymus tissues. First strand cDNA synthesis reactions (Sambrook et al., 1989) employed random 12 mers and Superscript II reverse transcriptase (Bethesda Research Laboratories). After second strand synthesis, the cDNAs were "anchored" by ligation of a specific double stranded oligo (dsRP.2) (5'-TGAGTAGAATTCTAACGGCCGTCATTGTTC-3' SEQ ID NO:28) to their 5' ends. The 5' end of the second cDNA stand was the only phosphorylated DNA end in the ligation reaction. After the ligation the anchored cDNA was purified by fractionation on Sepharose CL-4B columns. The anchored cDNA was amplified with a P16 specific reverse primer (5' AGCGTGTCCAGGAAGCCTTC-3' SEQ ID NO: 29) and a nested version of RP.2 (RP.B) (5'-TGAGTAGAATTCTAACGGCCGTCATTG-3' SEQ ID NO:30) followed by capture with a biotinylated gene-specific oligonucleotide (5'-ACTGCGAGGACCCCACTACCTTCTCC-3' SEQ ID NO:31) upstream of the reverse primer used in the first amplification. The captured cDNAs were amplified again, using RP.B and a gene-specific reverse primer (5'-GAACGTTGCCCATCATCATC-3' SEQ ID NO:32) upstream of the capture oligo. The resultant products were gel purified, cloned, and sequenced. The sequence for the mouse P16 oligonucleotides was determined by cloning and sequencing a mouse genomic clone that contained sequences hybridizing to a human E2 probe at low stringency.

Comparison of the mouse β transcript to the human suggests that E1β does not encode a protein. Only the sequence comprising the p16 reading frame in E2 was rigorously conserved. Therefore, if the β transcript were translated, it seems likely that the protein would initiate in E2 and be translated in the same frame used to encode p16. The deduced polypeptide would have a calculated molecular weight of 10 kDa and retain 2¾ of the 4 ankyrin repeats present in p16. However, p15 contains only 3½ ankyrin repeats (Hannon and Beach, 1994), and other proteins fold and function with only one or two repeats. Whether a p10 molecule exists in vivo and whether it inhibits CDK4/6 remain to be tested.

Function of the β RNA

If the role of the β transcript were to inhibit cell growth, we might find mutations which disrupt E1β in tumor-derived cell lines. Consistent with this view are two melanoma cell lines with deletions that remove E1β yet continue to express the α transcript The p16 coding sequence is wild type in these cell lines. Nevertheless, no small genetic lesions in E1β (e.g. base substitutions) were found in a set of 25 tumor cell lines. Therefore, it is difficult to conclude that E1β was the target of the homozygous deletions. If the E1β exon does not encode a protein, small genetic lesions may be insufficient to disrupt its function. Alternatively, the target of the deletions mentioned above might have been some other gene. For example, it is possible that the p15 gene (MTS2) was the relevant target of the deletions in these melanoma cell lines. In that view, E1β was deleted simply because it is closer to P15 than is E1α. However, since we were unable to detect P15 point mutations in a variety of cell lines, and because there were no cell lines that contained deletions which specifically removed P15 (Kamb et al., 1994b), this explanation seems unlikely.

The genetic evidence suggests that p16 and Rb are members of a growth regulatory pathway that is often inactivated during tumor progression. If the role of the β transcript is to negatively regulate cell growth, perhaps it is part of another pathway which must be mutated independently from p16 and Rb. This would explain why deletions which specifically disrupt E1β have only been seen in Rb cell lines. Based on its expression pattern, it seems likely that E1β plays a role in actively cycling cells. A definitive conclusion on the role of E1β awaits analysis of its expression in vivo.

EXAMPLE 14

Expression of MTS2 mRNA

RNA was isolated from cell lines or from primary T cells using RNazol B (CINNA/BIOTECX Laboratories, Inc.) as described by the manufacturer. cDNA was synthesized from total RNA (Sambrook et al., 1989) using a random 9 mer to prime DNA synthesis. cDNA yields were calculated by including $\alpha^{32}$P-dATP (Amersham) in the synthesis reaction (0.1 Ci/mmole) and determining the amount of radioactive nucleotide incorporated into the final product. MTS2 expression was analyzed by PCR using heminested reverse primers in two successive rounds of amplification. In the initial amplification, 2 ng of cDNA was amplified with E1F (5'-TGAGGGTCTGGCCAGC-3' SEQ ID NO:21) and X2.R140' (5'-AGCACCACCAGCGTGTC-3' SEQ ID NO:22). The reactions were done on a Perkin Elmer 9600 thermal cycler for 20 cycles under the following conditions: 97° C., 3 seconds; 65° C., 10 seconds; 75° C., 20 seconds. These reactions were diluted 100 fold and reamplified with E1F and X2B (5'-CGTGTCCAGGAAGCCC-3' SEQ ID NO:23). The X2B oligo was radiolabeled at its 5' end (Sambrook et al., 1989) with $\gamma^{32}$P-dATP (DuPont). PCR conditions were as above, but for only 15 cycles. The resultant products were resolved by electrophoresis through a denaturing 5% polyacrylamide gel. Dried gels were exposed to X-OMAT (Kodak) film overnight.

MTS2 expression in different tissues

Figure 10A:
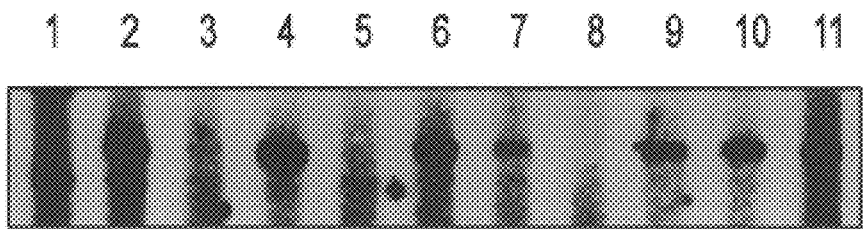
FIGS. 10A–C show expression of human MTS2 mRNA.

MTS2 was found to be expressed in many tissue types, including those that give rise to tumors in which MTS2 is homozygously deleted (see FIG. 10A). However, there were some differences among the tissues. For example, while the MTS2 transcript was easily detected in lung tissue, it was undetectable in prostrate and brain tissue. In contrast expression of the closely related MTS1 gene was detected in all of the tissues examined. It is unknown if the tissue specific differences in MTS2 RNA levels reflects a tissue specific requirement for the MTS2 protein.

MTS2 expression throughout the cell cycle

Figure 10B:
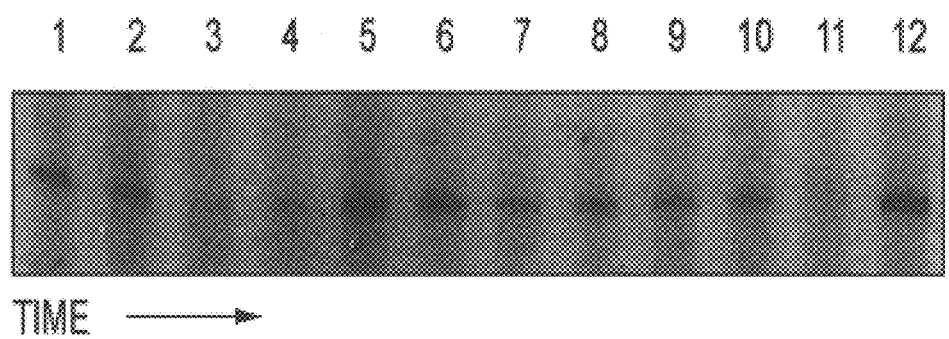

If MTS2 regulates important transitions in the cell cycle, its expression might vary through the cell cycle. For instance, in normal dividing cells the abundance of p21 mRNA varies as a function of cell cycle phase (Li et al., 1994b). To test whether or not MTS2 transcription was regulated through the cell cycle, quiescent human T cells were stimulated with PHA and IL2 and monitored at various stages after stimulation (see FIG. 10B). No obvious trend in MTS2 expression level was detected as the cells exited $G_o$ and passed through the cell cycle phases. In contrast, the expression of a control gene, CDK4, did change as expected (Matsushime et al., 1992). Thus, no evidence was found for the differential expression of MTS2 mRNA through the cycle of normally dividing cells.

Figure 10C:
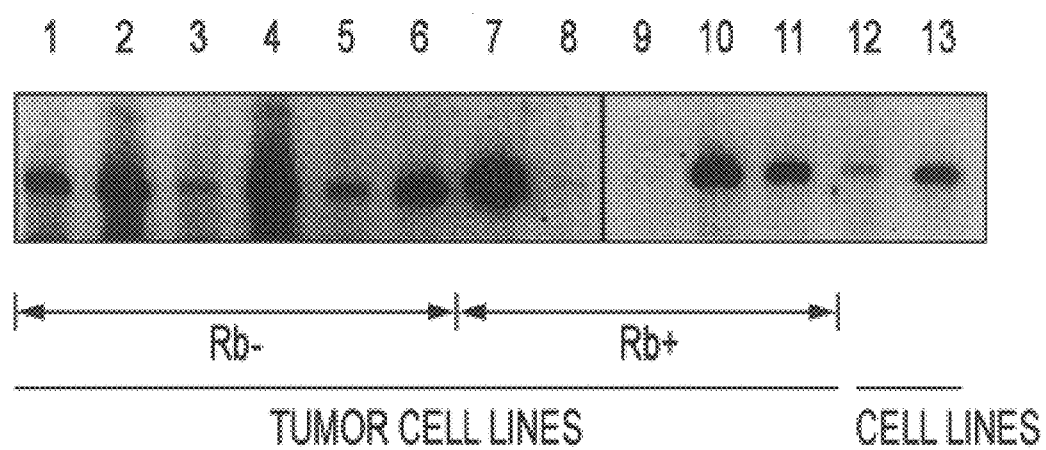

The MTS1 protein has been proposed to participate in a growth regulatory pathway involving the retinoblastoma protein Rb (Serrano et al., 1993; Guan et al., 1995; Serrano et al., 1995). Recent work has provided strong circumstantial evidence for the view that expression of MTS1 is controlled, at least in part, by Rb (Li et al., 1994a; Parry et al., 1995). The biochemical similarities between MTS1 and MTS2 suggest that MTS2 might also be regulated by Rb. This possibility was tested by comparing levels of MTS2 mRNA in Rb positive cell lines and Rb negative cell lines. No correlation between Rb status and MTS2 RNA levels was detected (see FIG. 10C). This suggests that the Rb status of the cell line does not dramatically affect the abundance of MTS2 transcript. Thus, in contrast to MTS1, MTS2 expression may be independent of Rb.

EXAMPLE 15

Ectopic Expression of MTS1 and MTS2

A 483 bp fragment of MTS1 was generated by a polymerase chain reaction using primers MTS1.F (5' AAA GGA TCC ATT GCC ACC ATG GAG CCG GCG GCG GGG AGC AGC ATG GAG CCT TCG GCT 3') (SEQ ID NO:17) and E3.R (5' TTT GAA TTC AAT CGG GGA TGT CTG 3') (SEQ ID NO:18). Primer MTS1.F was designed to include restriction enzyme sites near the 5' end for future cloning and a Kozak consensus sequence (Kozak, 1987). Template DNA for this reaction was cDNA from breast tissue. This generated fragment was inserted into the expression vector pcDNA3 (In Vitrogen) which had been digested with EcoRI and BamHI. pcDNA3 contains a cytomegalovirus (CMV) promoter and codes for resistance to ampicillin and neomycin. The resulting recombinant vector, pcDNAp16, was then inserted by electroporation into cell line HS294T. HS294T is derived from a melanoma and contains a homozygous deletion of both MTS1 and MTS2. HS294T was grown in DMEM (Gibco) supplemented with 10% fetal bovine serum, non-essential amino acids, sodium pyruvate, and L-glutamate. The cells were grown at 37° C. in 5% $CO_2$. HS294T was cotransformed with a 1:4 ratio of pSS (Stratagene), which confers hygromycin resistance to transformed cells, and either pcDNA3 (Invitrogen) expression vector containing the MTS1 coding sequence inserted downstream of the CMV promoter, or the pcDNA3 vector without an insert.

The coding portion of MTS2 was similarly cloned into pcDNA3, again forming a Kozak sequence, to yield pcDNAp15 and was inserted into HS294T. For this, MTS2 cDNA as prepared in Example 12 above was used.

Plasmid pSS (Stratagene) which contains the selectable marker for hygromycin resistance was simultaneously cotransferred with the pcDNAp16 or pcDNAp15, the pSS being present in the electroporation at 20 μg per cuvette. The conditions for electroporation were 800 μL of cells per cuvette at $1.5\times10^6$ cells/ml and 500 μF capacitance, 400 volts. Control experiments were performed using pcDNA3 plus pSS. The electroporated cells (about 400 μL) were placed in petri dishes with 300 μg/mL hygromycin. The number of colonies (foci) were counted after 14 days. The results are shown in Table 1 0.

TABLE 10

| Plasmids | pcDNAp15 Colonies/plate | pcDNAp16 Colonies/plate |
| --- | --- | --- |
| pcDNA3 + pSS | 26.6 ± 4.8 | 17.2 ± 0.15 |
| pcDNAp15 + pSS | 3.8 ± 0.8 | — |
| pcDNAp16 + pSS | — | 1.1 ± 0.5 |

When a construct containing the entire MTS2 coding sequence fused to the CMV promoter was transformed into HS294T, it inhibited colony formation by a factor of seven when compared to controls, comparable to the effect of ectopic expression of MTS1. This result indicates that ectopic expression of MTS2 is sufficient to inhibit cell growth. It is not clear whether the transformed cells are arrested in G1, as seems to result from ectopic expression of MTS1, or growth is arrested in some other manner. It can be concluded from the data of Table 10 that overexpression of p15 or p16 in a cell line which otherwise would lack p15 or p16 expression (here because of a homozygous deletion) inhibits growth of the cells. The precise mechanism is unclear but possibilities are that the p15 or p16 overexpression stops cell division or kills the cell. These results suggest that p15 and p16 function in vivo as bona fide tumor suppressor proteins and therefore p15 and p16 possibly have therapeutic uses.

For many reasons MTS2 is an attractive candidate for a tumor suppressor gene. It possesses extensive sequence similarity to MTS1, it binds to and inhibits CDK function in vitro, and ectopic expression of MTS2 inhibits cell growth in vivo. The above results raise the possibility that despite the biochemical similarity between MTS2 and MTS1, the two proteins have significantly different functions in vivo. Two features of MTS2 suggest that this may be so: i) MTS2, not MTS1, is induced by TGFβ (Hannon and Beach, 1994) and ii) unlike MTS1, MTS2 transcription appears to be independent of Rb. It is possible that MTS2 is not involved in tumorigenesis at all. Alternatively, MTS2 may participate in a pathway of tumor suppression distinct from the pathway involving MTS1. The elements of this pathway are not known, but it is conceivable that some of these elements may mutate at much higher frequencies than MTS2 in somatic tissue. In this view, the lack of somatic mutation of MTS2 in no way precludes an important role in tumor suppression. As noted above, ectopic expression of MTS2 inhibits cell growth, a role consistent with MTS2 being a tumor suppressor. The constant level of MTS2 expression during the cell cycle, and its induction by TGFβ, suggest a role for MTS2 in G1 arrest and not necessarily in regulating the timing of events in the cell cycle itself. In contrast, the regulation of MTS1 expression by Rb indicates that MTS1 may have a role in a cell cycle oscillator. It will be important to test the function of MTS2 as a growth control molecule in vivo, and to dissect the pathway(s) within which MTS2 functions.

EXAMPLE 16

Two Step Assay to Detect the Presence of MTS in a Sample

Patient sample is processed according to the method disclosed by Antonarakis, et al. (1985), separated through a 1% agarose gel and transferred to nylon membrane for Southern blot analysis. Membranes are UV cross linked at 150 mJ using a GS Gene Linker (Bio-Rad). MTS probe corresponding to nucleotide positions 448–498 of SEQ ID NO:4 is subcloned into pTZ18U. The phagemids are transformed into E. coli MV1190 infected with M13KO7 helper phage (Bio-Rad, Richmond, Calif.). Single stranded DNA is isolated according to standard procedures (see Sambrook, et al., 1989).

Blots are prehybridized for 15–30 min. at 65° C. in 7% sodium dodecyl sulfate (SDS) in 0.5 M $NaPO_4$. The methods follow those described by Nguyen, et al., 1992. The blots are hybridized overnight at 65° C. in 7% SDS, 0.5M $NaPO_4$ with 25–50 ng/ml single stranded probe DNA. Post-hybridization washes consist of two 30 min washes in 5% SDS, 40 mM $NaPO_4$ at 65° C., followed by two 30-min washes in 1% SDS, 40 mM $NaPO_4$ at 65° C.

Next the blots are rinsed with phosphate buffered saline (pH 6.8) for 5 min at room temperature and incubated with 0.2% casein in PBS for 30–60 min. at room temperature and rinsed in PBS for 5 min. The blots are then preincubated for 5–10 minutes in a shaking water bath at 45° C. with hybridization buffer consisting of 6M urea, 0.3 M NaCl, and 5× Denhardt's solution (see Sambrook, et al., 1989). The buffer is removed and replaced with 50–75 $\mu l/cm^2$ fresh hybridization buffer plus 2.5 nM of the covalently cross-linked oligonucleotide-alkaline phosphatase conjugate with the nucleotide sequence complementary to the universal primer site (UP-AP, Bio-Rad). The blots are hybridized for 20–30 min at 45° C. and post hybridization washes are incubated at 45° C. as two 10 min washes in 6M urea, 1× standard saline citrate (SSC), 0.1% SDS and one 10 min wash in 1× SSC, 0.1% Triton® X-100. The blots are rinsed for 10 min. at room temp. with 1× SSC.

Blots are incubated for 10 min at room temperature with shaking in the substrate buffer consisting of 0.1 M diethanolamine, 1 mM $MgCl_2$, 0.02% sodium azide, pH 10.0. Individual blots are placed in heat sealable bags with substrate buffer and 0.2 mM AMPPD (3-(2'-spiroadamantane)-4-methoxy-4-(3'-phosphoryloxy)phenyl-1,2-dioxetane, disodium salt, Bio-Rad). After a 20 min. incubation at room temperature with shaking, the excess AMPPD solution is removed. The blot is exposed to X-ray film overnight. Positive bands indicate the presence of MTS.

EXAMPLE 17

Generation of Polyclonal Antibody against MTS

Segments of MTS coding sequence were expressed as fusion protein in E. coli. The overexpressed protein was purified by gel elution and used to immunize rabbits and mice using a procedure similar to the one described by Harlow and Lane, 1988. This procedure has been shown to generate Abs against various other proteins (for example, see Kraemer, et al., 1993).

Briefly, a stretch of MTS coding sequence was cloned as a fusion protein in plasmid PET5A (Novagen, Inc., Madison, Wis.). The MTS incorporated sequence includes the amino acids corresponding to 448–498 of SEQ ID NO:4. After induction with IPTG, the overexpression of a fusion protein with the expected molecular weight was verified by SDS/PAGE. Fusion protein was purified from the gel by electroelution. The identification of the protein as the MTS fusion product was verified by protein sequencing at the N-terminus. Next, the purified protein was used as immunogen in rabbits. Rabbits were immunized with 100 $\mu$g of the protein in complete Freund's adjuvant and boosted twice in 3 week intervals, first with 100 $\mu$g of immunogen in incomplete Freund's adjuvant followed by 100 $\mu$g of immunogen in PBS. Antibody containing serum is collected two weeks thereafter.

This procedure is repeated to generate antibodies against the mutant forms of the MTS gene. These antibodies, in conjunction with antibodies to wild type MTS, are used to detect the presence and the relative level of the mutant forms in various tissues and biological fluids.

EXAMPLE 18

Generation of Monoclonal Antibodies Specific for MTS

Monoclonal antibodies are generated according to the following protocol. Mice are immunized with immunogen comprising intact MTS or MTS peptides (wild type or mutant) conjugated to keyhole limpet hemocyanin using glutaraldehyde or EDC as is well known.

The immunogen is mixed with an adjuvant. Each mouse receives four injections of 10 to 100 $\mu$g of immunogen and after the fourth injection blood samples are taken from the mice to determine if the serum contains antibody to the immunogen. Serum titer is determined by ELISA or RIA. Mice with sera indicating the presence of antibody to the immunogen are selected for hybridoma production.

Spleens are removed from immune mice and a single cell suspension is prepared (see Harlow and Lane, 1988). Cell fusions are performed essentially as described by Kohler and Milstein, 1975. Briefly, P3.65.3 myeloma cells (American Type Culture Collection, Rockville, Md.) are fused with immune spleen cells using polyethylene glycol as described by Harlow and Lane, 1988. Cells are plated at a density of $2\times10^5$ cells/well in 96 well tissue culture plates. Individual wells are examined for growth and the supernatants of wells with growth are tested for the presence of MTS specific antibodies by ELISA or RIA using wild type or mutant MTS target protein. Cells in positive wells are expanded and subcloned to establish and confirm monoclonality.

Clones with the desired specificities are expanded and grown as ascites in mice or in a hollow fiber system to produce sufficient quantities of antibody for characterization and assay development.

EXAMPLE 19

Sandwich Assay for MTS

Monoclonal antibody is attached to a solid surface such as a plate, tube, bead, or particle. Preferably, the antibody is attached to the well surface of a 96-well ELISA plate. 100 $\mu$l sample (e.g., serum, urine, tissue cytosol) containing the MTS peptide/protein (wild-type or mutants) is added to the solid phase antibody. The sample is incubated for 2 hrs at room temperature. Next the sample fluid is decanted, and the solid phase is washed with buffer to remove unbound material. 100 µl of a second monoclonal antibody (to a different determinant on the MTS peptide/protein) is added to the solid phase. This antibody is labeled with a detector molecule (e.g., 125-I, enzyme, fluorophore, or a chromophore) and the solid phase with the second antibody is incubated for two hrs at room temperature. The second antibody is decanted and the solid phase is washed with buffer to remove unbound material.

The amount of bound label, which is proportional to the amount of MTS peptide/protein present in the sample, is quantitated. Separate assays are performed using monoclonal antibodies which are specific for the wild-type MTS as well as monoclonal antibodies specific for each of the mutations identified in MTS.

It will be appreciated that the methods and compositions of the instant invention can be incorporated in the form of a variety of embodiments, only a few of which are disclosed herein. It will be apparent to the artisan that other embodiments exist and do not depart from the spirit of the invention. Thus, the described embodiments are illustrative and should not be construed as restrictive.

LIST OF REFERENCES

American Cancer Society (1992). In *Cancer Facts and Figures*—1992.
Anand, R. (1992). *Techniques for the Analysis of Complex Genomes*, (Academic Press).
Anderson, et al. (1980). *Proc. Natl. Acad. Sci. USA* 77:5399–5403.
Anderson, J. A., et al. (1992). *J. Otolaryngology* 21:321.
Antonarakis, S. E., et al. (1985). *New Engl. J. Med.* 313:842–848.
Ausubel, F. M., et al. (1992). *Current Protocols in Molecular Biology*, (John Wiley and Sons, New York, N.Y.).
Beaucage & Carruthers (1981). *Tetra. Letts.* 22:1859–1862.
Bergman, W., et al. (1990). *Br. J. Cancer* 61, 932–936.
Berkner (1992). *Curr. Top. Microbiol. Immunol.* 158:39–61.
Berkner, et al. (1988). *BioTechniques* 6:616–629.
Bird, A. P. (1989). *Nucleic Acids Res.* 17:9485.
Birnboim, H. C. & Doly, J. (1979). *Nuc. Acids Res.* 7:1513–1523.
Boyum, A. (1968). *Scand. J. Clin. Lab. Invest.* 21(suppl. 97):77–89.
Brandyopadhyay and Temin (1984), *Mol. Cell. Biol.* 4:749–754.
Breakfield and Geller (1987). *Mol. Neurobiol.* 1:337–371.
Brinster, et al. (1981). *Cell* 27:223–231.
Buchschacher and Panganiban (1992). *J. Virol.* 66:2731 –2739.
Buckley, M. F., Sweeney, K. J., Hamilton, J. A., Sini, R. L., Manning, D. L., Nicholson, R. I., deFazio, A., Watts, C. K., Musgrove, E. A. and Sutherland, R. L. (1993). *Oncogene* 8:2127–2133.
Cairns, P., Mao, L., Merlo, A., Lee, D. J., Schwab, D., Eby, Y., Tokino, K, van der Riet, P., Blaugrund, J. E. and Sidransky, D. (1994). *Science* 265:415–416.
Caldas, C., Hahn, S. A., da Costa, L., Redston, M. S., Schutte, M., Seymour, A. B., Weinsten, C. L., Hruban, R. H., Yeo, C. J. and Kern, S. E. (1994). *Nature Genetics* 8:27–32.
Cannon-Albright, L. A., Goldgar, D. E., Meyer, L. J., Lewis, C. M., Anderson, D. E., Fountain, J. W., Hegi, M. E., Wiseman, R. W., Petty, E. M., Bale, A. E., Olopade, O. I., Diaz, M. O., Kwiatkowski, D. J., Piepkorn, M. W., Zone, J. J. and Skolnick, M. H. (1992). *Science* 258:1148–1152.
Capecchi, M. R. (1989). *Science* 244:1288.
Cariello (1988). *Human Genetics* 42:726.
Cheng, J. Q., et al. (1993). *Cancer Res.* 53:4761.
Cohen, D., et al. (1993). *Nature* 366, 698–701.
Conner, B. J., et al. (1983). *Proc. Nat. Acad Sci. USA.* 80:278–282.
Constantini and Lacy (1981). *Nature* 294:92–94.
Cotten, et al. (1990). *Proc. Natl. Acad. Sci. USA* 87:4033–4037.
Cotton, et al. (1988). *Proc. Nat. Acad Sci. USA* 85:4397.
Culver, et al. (1992). *Science* 256:1550–1552.
Curiel, et al. (1991a). *Proc. Natl. Acad. Sci. USA* 88:8850–8854.
Curiel, et al. (1991b). *Hum. Gene Ther.* 3:147–154.
Deutscher, M. (1990). *Meth. Enzymology* 182:83–89 (Academic Press, San Diego).
Diaz, M. O., et al. (1988). *Proc. Natl. Acad. Sci USA* 85: 5259–5263.
Diaz, M. O., et al. (1990). *New Engl. J. Med.* 322:77.
Donehower, L. A., et al. (1992). *Nature* 356:215.
El-Diery, W. S., Tokino, T., Velculescu, V. E., Levy, D. B., Parsons, R., Trent, J. M., Lin, D., Mercer, W. E., Kinszler, K. W. and Vogelstein, B. (1993). *Cell* 75:817–825.
Elstad, M. R. et al. (1988). *J. Immunol.* 140:1618–1624.
*Enhancers and Eukaryotic Gene Expression,* Cold Spring Harbor Press, Cold Spring Harbor, N.Y. (1983).
Erickson, J. et al. (1990). *Science* 249:527–533.
Ewen, M. E., et al. (1993). *Cell* 73:47.
Felgner, et al. (1987). *Proc. Natl. Acad. Sci. USA* 84:7413–7417.
Fiers, et al. (1978). *Nature* 273:113.
Fink, et al. (1992). *Hum. Gene Ther.* 3:11–19.
Finkelstein, J., et al. (1990). *Genomics* 7:167–172.
Firpo, E. J., Koff, A., Solomon, M. J. and Roberts, J. M. (1994). *Mol. Cell. Biol.* 14:4889–4901.
Fountain, J. W., et al. (1992). *Proc. Natl. Acad Sci. USA* 89:10557–10561.
Freese, et al. (1990). *Biochem. Pharmacol.* 40:2189–2199.
Friedman, T. (1991). In *Therapy for Genetic Diseases,* T. Friedman, ed., Oxford University Press, pp. 105–121.
Geng, Y. and Weinberg, R. A. (1993). *Proc. Natl. Acad Sci. USA* 90:10315–10319.
Glover, D. (1985). *DNA Cloning,* I and II (Oxford Press).
Goding (1986). *Monoclonal Antibodies: Principles and Practice,* 2d ed. (Academic Press, New York).
Godowski, et al. (1988). *Science* 241:812–816.
Goldstein, A. M., et al. (1994). *Am. J. Hum. Genet.* 54:489.
Gordon, et al. (1980). *Proc. Natl. Acad. Sci. USA* 77:7380–7384.
Gorziglia and Kapikian (1992). *J. Virol.* 66:4407–4412.
Graham and van der Eb (1973). *Virology* 52:456–467.
Gruis, N. A., et al. (1993). *Melanoma Res.* 3:271.
Gu, Y., et al. (1993). *Nature* 366:707.
Guan, K.-L., Jenkins, C. W., Li, Y., Nichols, M. A., Wu, X., O'Keefe, C. L., Matera, A. G. and Xong, Y. (1995). *Genes Dev.* 8, 6078–6082.
Guthrie, G. & Fink, G. R. (1991). *Guide to Yeast Genetics and Molecular Biology,* (Academic Press).
Hannon, G. J. and Beach, D. (1994). *Nature* 371:257–261.
Harlow & Lane (1988). *Antibodies: A Laboratory Manual,* (Cold Spring Harbor Laboratory, Cold Spring Harbor, N.Y.).
Harper, J. W., Adami, G. R., Wei, N., Keyomarsi, K and Elledge, S. J. (1993). *Cell* 75:805–816.
Hasty, P. K., et al. (1991). *Nature* 350:243.
Hebert, J., Cayuela, J. M., Berkeley, J. and Sigaux, F. (1994). *Blood* 84:4038–4044.
Helseth, et al. (1990). *J. Virol.* 64:2416–2420.

Henco, K., et al. (1985). *J. Mol. Biol.* 185:227–260.
Hodgson, J. (1991). *Bio/Technology* 9:19–21.
Hori, et al. (1987). *Blood* 70:1069–1071.
Hunter, T. and Pines, J. (1994). *Cell* 79:573–582.
Huse, et al. (1989). *Science* 246:1275–1281.
Hussussian, C. J., Struewing, J. P., Goldstein, A. M., Higgins, P. A. T., Ally, D. S., Sheahan, M. D., Clark, W. H. Jr., Tucker, M. A. and Dracopoli, N. C. (1994). *Nature Genetics* 8:15–21.
Innis et al. (1990). *PCR Protocols: A Guide to Methods and Applications,* (Academic Press, San Diego).
Jablonski, E., et al. (1986). *Nucl. Acids Res.* 14:6115–6128.
Jakoby, W. B. and Pastan, I. H. (eds.) (1979). Cell Culture. Methods in Enzymology, volume 58 (Academic Press, Inc., Harcourt Brace Jovanovich (New York)).
James, C. D., et al. (1993). *Cancer Res.,* 53:3674.
Johnson, et al. (1992). *J. Virol.* 66:2952–2965.
Kamb, A., Weir, M., Rudy, B., Varmus, H. and Kenyon, C. (1989). *Proc. Natl. Acad Sci. U.S.A.* 86:4372–4376.
Kamb, A. et al. (1994a). *Nature Genetics* 8:22–26.
Kamb, A. et al. (1994b). *Science* 264:436–440.
Kaneda, et al. (1989). *J. Biol. Chem.* 264:12126–12129.
Kanehisa (1984). *Nuc. Acids Res.* 12:203–213.
Kato, J.-Y., Matsuoka, M., Massague, J. and Sherr, C. J. (1994). *Cell* 79:487–496.
Kinszler, K. W., et al. (1991). *Science* 251:1366–1370.
Knudson, A. G. (1971). *Proc. Natl. Acad Sci. USA* 68:820.
Knudson, A. G. (1993). *Nature Genet.* 5:103.
Kohler, G. and Milstein, C. (1975). *Nature* 256:495–497.
Kozak, M. (1986). *Cell* 44:283–292.
Kozak, M. (1987). *Nucl. Acids Res.* 15:8125–8148.
Kraemer, F. B., et al. (1993). *J. Lipid Res.* 34: 663–672.
Kubo, T., et al. (1988). *FEBS Lett.* 241:119.
Kwiatkowski, D. J. & Diaz, M. O. (1992). *Hum. Mol. Genet* 1:658.
Lammie, G. A., et al. (1991). *Oncogene,* 6:439.
Landegren, et al. (1988). *Science* 242:229.
Larsen, F., et al. (1992). *Genomics* 13:1095.
Li, Y. et al. (1994a). *Cancer Research* 54:6078–6082.
Li, Y., Jenkins, C. W., Nichols, M. A., and Xiong, Y. (1994b). *Oncogene* 9:2261–2268.
Lim, et al. (1992). *Circulation* 83:2007–2011.
Liu, Q., Neuhausen, S., McClure, M., Frye, C., Weaver-Feldhaus, J. Gruis, N. A., Eddington, K. Allalunis-Turner, M. J., Skolnick, M. H., Fujimura, F. K., Kamb, A. (1995). *Oncogene* In press.
Lukeis, R., et al. (1990). *Genes, Chromo. Cancer* 2:116–124.
Madzak, et al. (1992). *J. Gen. Virol.* 73:1533–1536.
Malkin, D., et al. (1990). *Science* 250:1233.
Maniatis. T., et al. (1982). *Molecular cloning: A laboratory manual* (Cold Spring Harbor Laboratory, Cold Spring Harbor, N.Y.).
Mann and Baltimore (1985). *J. Virol.* 54:401–407.
Margolskee (1992). *Curr. Top. Microbiol. Immunol.* 158:67–90.
Martin, R., et al. (1990). *BioTechniques* 9:762–768.
Marx, J. (1994). *Science* 263:319–321.
Matsushime, H., Ewen, M. E., Strom, D. K., Kato, J.-Y., Hanks, S. K., Roussel, M. F. and Sherr, C. J. (1992). *Cell* 71:323–334.
Matteucci, et al. (1981). *J. Am. Chem. Soc.* 103:3185.
Matthews & Kricka (1988). *Anal. Biochem* 169:1.
Merrifield (1963). *J. Am. Chem. Soc.* 85:2149–2156.
Metzger, et al. (1988). *Nature* 334:31–36.
Middleton, P. G., et al. (1991). *Leukemia* 5:680–682.
Miller (1992). *Curr. Top. Microbiol. Immunol.* 158:1–24.
Miller, et al. (1985). *Mol. Cell. Biol.* 5:431–437.
Miller, et al. (1988). *J. Virol.* 62:4337–4345.
Mittlin (1989). *Clinical Chem.* 35:1819.
Modrich, P. (1991). *Ann. Rev. Genet.* 25:229–253.
Mombaerts, P., et al. (1992). Cell 68:869.
Mori, T., Miura, K., Aoki, T., Nishihira, T., Mori, S. and Nakamura, Y. (1994). *Cancer Res.* 54:3396–3397.
Moss (1992). *Curr. Top. Microbiol. Immunol.* 158:25–38.
Motokura, T., et al. (1991). *Nature* 350:512.
Muzyczka (1992). *Curr. Top. Microbiol. Immunol.* 158:97–123.
Nabel, et al. (1990). *Science* 249:1285–1288.
Nabel (1992). *Hum. Gene Ther.* 3:399–410.
Nancarrow, D. J., et al. (1993). *Am. J. Hum. Genet.* 53:936.
Nasmyth, K. & Hunt, T. (1993). *Nature* 366:634–635.
Newton, C. R., Graham, A., Heptinstall, L. E., Powell, S. J., Summers, C., Kalsheker, N., Smith, J. C., and Markham, A. F. (1989). *Nucl. Acids Res.* 17: 2503–2516.
Nguyen, Q., et al. (1992). *BioTechniques* 13:116–123.
Nobori, T., Miura, K., Wu, D. J., Lois, A., Takabayashi, K. and Carson, D. (1994). *Nature* 368:753–756.
Novack, et al. (1986). *Proc. Nat. Acad. Sci. USA* 83:586.
Ohi, et al. (1990). *Gene* 89:279–282.
Olopade, O. I., et al. (1992). *Cancer Res.* 52:2523–2529.
Olopade, O. I., et al. (1993). *Cancer Res.* 53:2410–2415.
Orita, et al. (1989). *Proc. Nat. Acad. Sci. USA* 86:2776–2770.
Page, et al. (1990). *J. Virol.* 64:5370–5276.
Parry, D., Bates, S., Mann, D. J. and Peters, G. (1995). *EMBO J.* 14, 503–511.
Pellicer, et al. (1980). *Science* 209:1414–1422.
Petropoulos, et al. (1992). *J. Virol.* 66:3391–3397.
Philpott, K. L., et al. (1992). *Science* 256:1448.
Polyak, K., Kato, J., Solomon, M. J., Sherr, M. J., Massague, J., Roberts, J. M. and Koff, A. (1994a). *Genes Dev.* 8:9–22.
Polyak, K. and Lee, M. H. (1994b). *Cell* 78:59–66.
Quantin, et al. (1992). *Proc. Natl. Acad Sci. USA* 89:2581–2584.
Rano & Kidd (1989). *Nucl. Acids Res.* 17:8392.
Rigby, P. W. J., et al. (1977). *J. Mol. Biol.* 113:237–251.
Rosenberg, C. L., et al. (1991). *Proc. Natl. Acad. Sci. USA* 88:9638.
Rosenfeld, et al. (1992). *Cell* 68:143–155.
Russell, L. and Forsdyke, D. R. (1991). *DNA Cell Bio.* 10:581–591.
Sambrook, J., et al. (1989). *Molecular cloning. A laboratory manual,* 2nd Ed. (Cold Spring Harbor Laboratory, Cold Spring Harbor, N.Y.).
Scharf (1986). *Science* 233:1076.
Scopes, R. (1982). *Protein Purification: Principles and Practice,* (Springer-Verlag, New York).
Serrano, M., et al. (1993). *Nature* 366:704.
Serrano, M. et al. (1995). *Science* 267:249–252.
Sheffield, V. C., et al. (1989). *Proc. Nat. Acad Sci USA* 86: 232–236.
Shenk, et al. (1975). *Proc. Nat. Acad. Sci. USA* 72:989.
Sherr, C. J. (1993). *Cell* 73:1059.
Shimada, et al. (1991). *J. Clin. Invest.* 88:1043–1047.
Shinkai, Y., et al. (1992). *Cell* 68:855.
Slingerland, J. M., Hengst, L., Pan, C.-H., Alexander, D., Stampher, M. R. and Reed, S. I. (1994). *Mol. Cell. Biol.* 14:3683–3694.
Snouwaert, J. N., et al. (1992). *Science* 257:1083.
Sorge, et al. (1984). *Mol. Cell. Biol.* 4:1730–1737.
Spruck III, C. H., Gonzalez-Zulueta, M., Shibata, A., Simoneau, R. R., Lin, M.-F., Gonzales, F., Tsai, Y. C. and Jones, P. (1994). *Nature* 370:183–184.

Stewart, et al. (1992). *Hum. Gene Ther.* 3:267–275.
Stone, S., Dayananth, P., Jiang, P., Weaver-Feldhaus, M. M., Tavtigian, S. V., Skolnick, M. H., and Kamb, A. (1995a). *Oncogene,* in press.
Stone, S., Jiang, P., Dayananth, P., Tavtigian, S. V., Katcher, H., Parry, D., Peters, G., Kamb, A. (1995b). *Cancer Res.* 55: in press.
Stratford-Perricaudet, et al. (1990). *Hum. Gene Ther.* 1:241–256.
Tam, S. W., Theodoras, A. M., Shay, J. W., Draetta, G. F. and Pagano, M. (1994a). *Oncogene* 9:2663–2674.
Tam, S. W., Shay, J. W. and Pagano, M. (1994b). *Cancer Res.* 54:5816–5820.
Toyoshima, H. and Hunter, T. (1994). *Cell* 78:67–74.
Valancius, V. & Smithies, O. (1991). *Mol. Cell Biol.* 11:1402.
Wagner, et al. (1990). *Proc. Natl. Acad. Sci. USA* 87:3410–3414.
Wagner, et al. (1991). *Proc. Natl. Acad. Sci. USA* 88:4255–4259.
Wang and Huang (1989). *Biochemistry* 28:9508–9514.
Wartell, R. M., et al. (1990). *Nucl. Acids Res.* 18:2699–2705.
Weaver-Feldhaus, et al. (1994). *Proc. Nat. Acad Sci USA* 91:7563–7567.
Wells, J. A. (1991). *Methods Enzymol.* 202:390–411.
Wetmur & Davidson (1968). *J. Mol. Biol.* 31:349–370.
White & Lalouel (1988). *Ann. Rev. Genet.* 22:259–279.
Wilkinson, et al. (1992). *Nucleic Acids Res.* 20:2233–2239.
Withers, D. A., et al. (1991). *Mol. Cell. Biol.* 11:4846.
Wolff, et al. (1990). *Science* 247:1465–1468.
Wolff, et al. (1991). *BioTechniques* 11:474–485.
Wu, et al. (1989a). *Genomics* 4:560–569.
Wu, et al. (1989b). *J. Biol. Chem.* 264:16985–16987.
Wu, et al. (1991). *J. Biol. Chem.* 266:14338–14342.
Xiong, Y. et al. (1993). *Nature* 366:701.
Zenke, et al. (1990). *Proc. Natl. Acad. Sci. USA* 87:3655–3659.

LIST OF PATENTS AND PATENT APPLICATIONS

U.S. Pat. No. 3,817,837
U.S. Pat. No. 3,850,572
U.S. Pat. No. 3,939,350
U.S. Pat. No. 3,996,345
U.S. Pat. No. 4,275,149
U.S. Pat. No. 4,277,437
U.S. Pat. No. 4,366,241
U.S. Pat. No. 4,376,110
U.S. Pat. No. 4,486,530
U.S. Pat. No. 4,683,195
U.S. Pat. No. 4,683,202
U.S. Pat. No. 4,816,567
U.S. Pat. No. 4,868,105
U.S. Pat. No. 5,252,479
EPO Publication No. 225,807
European Patent Application Publication No. 0332435
Geysen, PCT published application WO 84/03564, published Sep. 13, 1984
Hitzeman et al., EP 73,675A
PCT published application WO 93/07282

What is claimed is:

1. An isolated nucleic acid comprising the sequence shown as SEQ ID NO:45.

2. A replicative cloning vector which comprises the isolated nucleic acid of claim 1.

3. An expression system which comprises the isolated DNA of claim 1 operably linked to suitable control sequences.

4. Recombinant host cells transformed with the replicative cloning vector of claim 2.

5. Recombinant host cells transformed with the expression system of claim 3.

* * * * *